(12) United States Patent
Mendell et al.

(10) Patent No.: US 8,729,041 B2
(45) Date of Patent: May 20, 2014

(54) COMPOSITIONS AND METHODS FOR TREATING HEPATIC NEOPLASIA

(75) Inventors: Joshua T. Mendell, Dallas, TX (US); Kathryn A. Mendell, Baltimore, MD (US); Raghu R. Chivukula, Baltimore, MD (US); Erik A. Wentzel, Leesburg, VA (US); Jerry R. Mendell, Columbus, OH (US); K. Reed Clark, Westerville, OH (US); Janaiah Kota, Columbus, OH (US)

(73) Assignees: The Johns Hopkins University, Baltimore, MD (US); Nationwide Children's Hospital, Inc., Columbus, OH (US)

( * ) Notice: Subject to any disclaimer, the term of this patent is extended or adjusted under 35 U.S.C. 154(b) by 0 days.

(21) Appl. No.: 13/132,783

(22) PCT Filed: Dec. 2, 2009

(86) PCT No.: PCT/US2009/066399
§ 371 (c)(1),
(2), (4) Date: Aug. 24, 2011

(87) PCT Pub. No.: WO2010/065630
PCT Pub. Date: Jun. 10, 2010

(65) Prior Publication Data
US 2011/0301226 A1    Dec. 8, 2011

Related U.S. Application Data

(60) Provisional application No. 61/119,494, filed on Dec. 3, 2008.

(51) Int. Cl.
*A61K 48/00*    (2006.01)
*A61P 1/16*    (2006.01)
*A61P 35/00*    (2006.01)
*C12N 15/86*    (2006.01)
*C12N 15/113*    (2010.01)

(52) U.S. Cl.
USPC ........ 514/44; 435/6.11; 435/6.13; 435/320.1; 435/325; 536/23.1; 536/24.1; 536/24.5

(58) Field of Classification Search
USPC ............... 435/6, 91.1, 91.31, 455, 6.11, 6.13, 435/320.1, 325, 375; 514/44; 536/23.1, 536/24.5, 24.1
See application file for complete search history.

(56) References Cited

U.S. PATENT DOCUMENTS

| | | | |
|---|---|---|---|
| 7,888,010 B2 * | 2/2011 | Brown et al. | 435/6.14 |
| 2006/0189557 A1 | 8/2006 | Slack et al. | |
| 2007/0259350 A1 | 11/2007 | Bentwich et al. | |
| 2009/0004668 A1 * | 1/2009 | Chen et al. | 435/6 |
| 2009/0131356 A1 * | 5/2009 | Bader et al. | 514/44 |

FOREIGN PATENT DOCUMENTS

WO    2008124777 A1    10/2008

OTHER PUBLICATIONS

Doench et al., Genes & Dev., vol. 18, No. 5, pp. 504-511 (2004).*
Opalinska et al., Nature Rev., vol. 1, pp. 503-514 (2002).*
Jiang et al., "Association of MicroRNA Expression in Hepatocellular Carcinomas with Hepatitis Infection, Cirrhosis, and Patient Survival", Clin. Cancer Research, vol. 14, No. 2, pp. 419-427 (2008).

* cited by examiner

*Primary Examiner* — Jane Zara
(74) *Attorney, Agent, or Firm* — Edwards Wildman Palmer LLP; Peter F. Corless; Richard B. Emmons

(57) ABSTRACT

The present invention provides compositions and methods featuring miR-26 microRNA polynucleotides for the diagnosis, treatment or prevention of hepatic neoplasia.

10 Claims, 17 Drawing Sheets

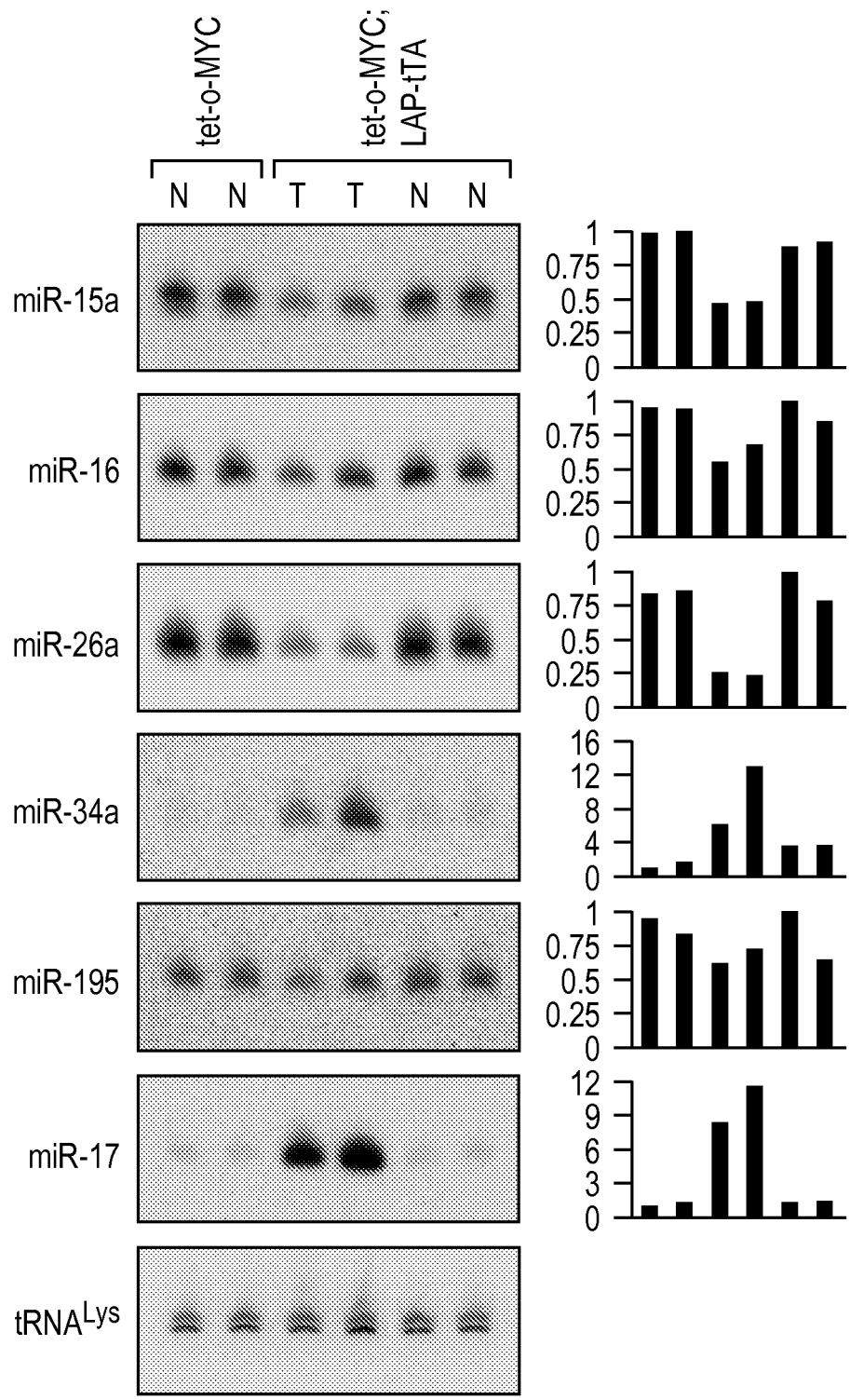

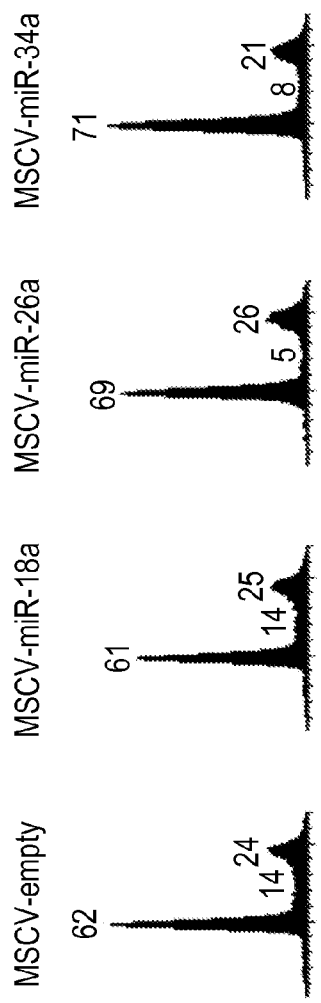
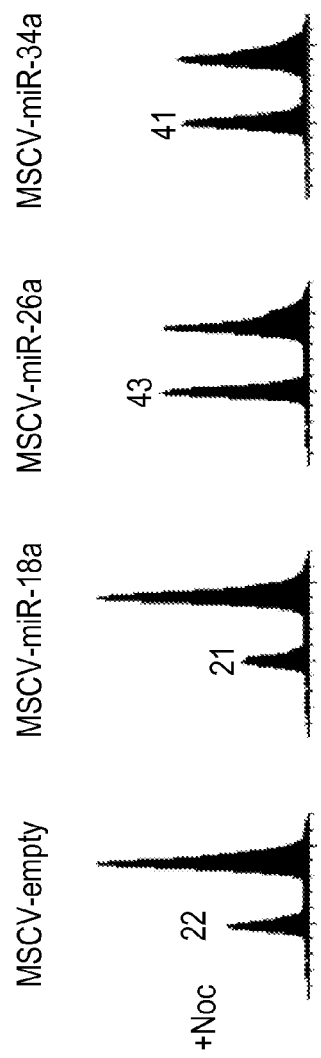
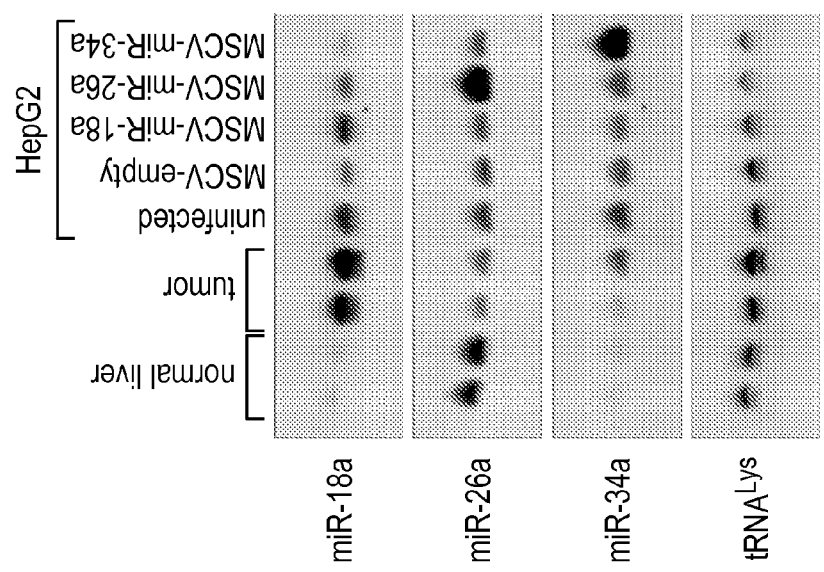

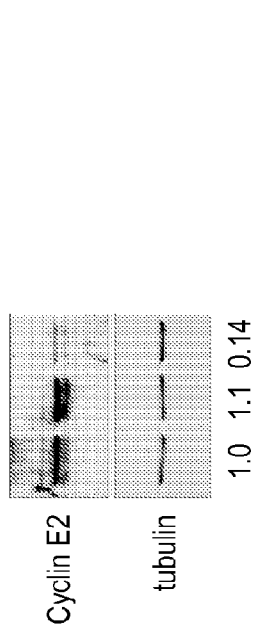
FIG. 3A
FIG. 3B
FIG. 3C
miR-26a
3'-CGGAUAGGACCUAAUGAACUU-5'
CAGCGUACUUGAAUUUU human
CAUUGUACUUGAAGAC- mouse
CAUUGUACUUGAAGA-- rat
CAGCGUACUUGAA-UUU dog
CAGUGUACUUGAAUUUA chicken
CAGCGAAGUAGUAUUUU mutant UTR
[CCND2]
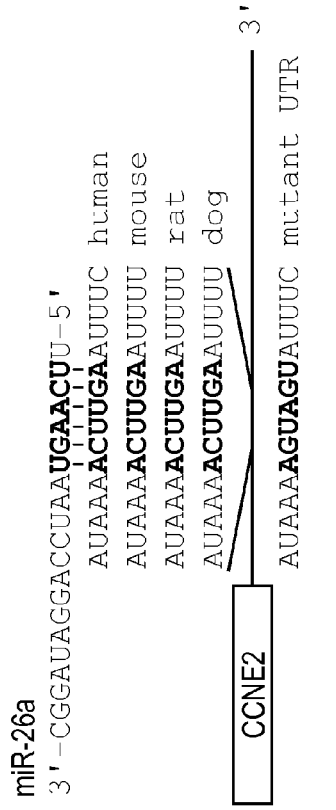
FIG. 3D
miR-26a
3'-CGGAUAGGACCUAAUGAACUU-5'
AUAAAACUUGAAUUUC human
AUAAAACUUGAAUUUU mouse
AUAAAACUUGAAUUUU rat
AUAAAACUUGAAUUUU dog
AUAAAAGUAGUAUUUC mutant UTR
[CCNE2]

FIG. 4F
scAAV8.eGFP
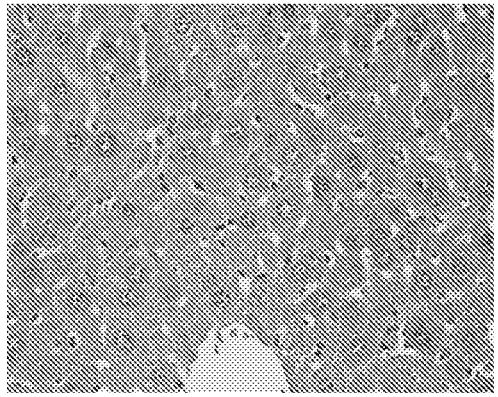
scAAV8.miR26a.eGFP
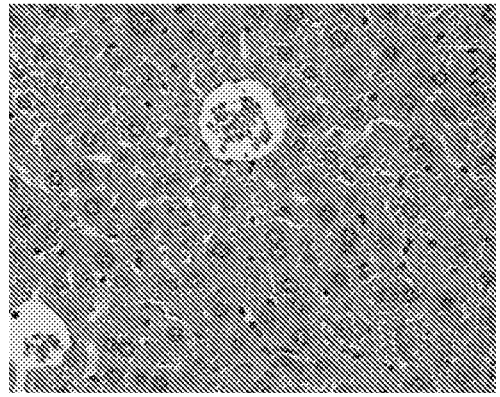

US 8,729,041 B2

COMPOSITIONS AND METHODS FOR TREATING HEPATIC NEOPLASIA

GOVERNMENT SUPPORT

This invention was made with government support under N.I.H. grant RO1CA120185. The U.S. Government has certain rights in the invention.

CROSS-REFERENCE TO RELATED APPLICATIONS

This application is a 35 U.S.C. §371 U.S. national entry of International Application PCT/US2009/066399 (WO 2010/065630) having an International filing date of Dec. 2, 2009 which claims the benefit of the following U.S. Provisional Application No. 61/119,494, filed on Dec. 3, 2008, the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy, created on Aug. 11, 2011, is named 85219716.txt and is 12,709 bytes in size.

BACKGROUND OF THE INVENTION

MicroRNAs (miRNAs) are a diverse class of highly conserved small RNA molecules that function as critical regulators of gene expression in multicellular eukaryotes and some unicellular eukaryotes. miRNAs are initially transcribed as long primary transcripts (pri-miRNAs) that undergo sequential processing by the RNase III endonucleases Drosha and Dicer to yield the mature ~20-23 nucleotide species. Mature miRNAs associate with the RNA-induced silencing complex (RISC) and interact with sites of imperfect complementarity in 3' untranslated regions (UTRs) of target mRNAs. Targeted transcripts subsequently undergo accelerated turnover and translational repression. Importantly, the ability of individual miRNAs to regulate hundreds of transcripts allows these RNAs to coordinate complex programs of gene expression and thereby induce global changes in cellular physiology. Indeed, a growing body of evidence has documented that miRNAs provide functions essential for normal development and cellular homeostasis and accordingly, dysfunction of these molecules has been linked to multiple human diseases.

Cancer causes one in every four US deaths and is the second leading cause of death among Americans. Hepatocellular carcinoma (HCC) is the third-leading cause of death from cancer and the fifth most common malignancy worldwide. HCC is often diagnosed at an advanced stage when it is no longer amenable to curative therapies. Highly active drug-metabolizing pathways and multi-drug resistance transporter proteins in tumor cells further diminish the efficacy of current therapeutic regimens for this cancer type.

SUMMARY OF THE INVENTION

As described below, the present invention features compositions and methods for the diagnosis, treatment or prevention of hepatic cancer, including established tumors.

The invention provides methods of reducing hepatic tumorigenesis in a subject by administering to the subject an agent that increases miR-26 expression relative to a reference, thereby reducing hepatic tumor formation.

The invention provides methods of treating or preventing a hepatic neoplasia in a subject by administering to the subject an agent that increases miR-26 expression relative to a reference, thereby treating or preventing the neoplasia.

The invention further provides methods of increasing miR-26 expression in a hepatic neoplastic cell by contacting the cell with an agent that increases miR-26 expression relative to a reference.

The invention provides methods of preventing or treating a hepatic neoplasia, the method comprising contacting a hepatic neoplastic cell with an agent that increases miR-26 expression relative to a reference, thereby treating or preventing the neoplasia.

The treatment and prevention methods of the invention can be carried out using an agent is an expression vector comprising a polynucleotide encoding miR-26 microRNA. In various embodiments, miR-26 microRNA is any miR-26 microRNA, that is any or all of miR-26a-1 microRNA, miR-26a-2 microRNA, and miR-26b microRNA.

The invention further provides expression vectors including a polynucleotide encoding miR-26 positioned for expression in a mammalian cell for use as a therapeutic agent for the treatment of hepatic neoplasia for use as an agent for the treatment of hepatic neoplasia. For example, the miR-26 is positioned adjacent to an appropriate promoter for expression in a liver cell, either a liver-specific promoter or a non-liver specific promoter, and the promoter and coding sequence are flanked by inverted terminal repeats. The sequence is then further inserted into a vector sequence, which in certain embodiments can replicate in a human cell. The polynucleotide can be an isolated polynucleotide.

In certain embodiments, the vector is a viral expression vector. In certain embodiments, the viral expression vector is an adenoviral vector, an adeno-associated viral (AAV) vector, or a lentiviral vector. Adenoviral vectors include viral vector is a self-complementary adeno-associated viral vector. In certain embodiments, the AAV vector is based on a single serotype of AAV, such as AAV1, AAV2, AAV3, AAV4, AAV5, AAV6, AAV7, AAV8, and AAV9. Modified AAV vectors based substantially on a single serotype are known in the art, for example serotype rh.74 which is AAV8-like and shares 93% amino acid identity with AAV8 can be used (see, e.g., Martin et al., *Am. J. Cell. Physiol.* 296:C476-C488, 2009, incorporated herein by reference). Alternatively, the adeno-associated viral vector is a chimeric adeno-associated viral vector based on multiple serotypes of AAV.

The expression vectors provided by the instant invention can include any sequence that encodes a functional miR-26 for use in any of the methods of the instant invention. In certain embodiments, the expression vector includes a nucleic acid sequence selected from the group selected from SEQ ID NO: 1-11. For example, the expression vectors of the instant invention can direct the expression of any miR-26 microRNA, that is any or all of miR-26a-1 microRNA, miR-26a-2 microRNA, and miR-26b microRNA.

The invention provides cells containing an isolated polynucleotide encoding miR-26 of the instant invention. The cell is a bacterial cell or a mammalian cell. The cell can be a cell to which the polynucleotide has been delivered as a therapeutic intervention. Alternatively, the cell can be a cell in vitro used for the preparation of a pharmaceutical composition for the prevention or treatment of hepatic neoplasia of the invention.

The invention provides pharmaceutical compositions and the use of agents of the invention for the preparation of medicaments and pharmaceutical compositions for the treatment of hepatic neoplasia. The pharmaceutical compositions include an effective amount of an isolated miR-26 polynucleotide in a pharmaceutically acceptable excipient. In certain embodiments, the polynucleotide is a microRNA. In certain embodiments, the polynucleotide comprises at least one chemical modification. In the pharmaceutical composition of the invention, miR-26 microRNA is any or all of miR-26a-1 microRNA, miR-26a-2 microRNA, and miR-26b microRNA.

The invention provides kits for the treatment of a hepatic neoplasia including an effective amount of an agent that increases miR-26 expression, and written instructions for using the kit. In the kits of the invention, miR-26 microRNA is any or all of miR-26a-1 microRNA, miR-26a-2 microRNA, and miR-26b microRNA.

The invention provides methods for identifying or characterizing a hepatic neoplasia in a subject by detecting miR-26 in a biological sample derived from the subject, thereby identifying or characterizing the hepatic neoplasia.

The invention further provides methods for diagnosing a subject as having or having a propensity to develop a hepatic neoplasia by measuring the level of miR-26 in a biological sample from the subject, and detecting an alteration in the level of the miR-26 in the sample relative to the level in a control sample, wherein detection of a decrease in the miR-26 level indicates the subject has or has a propensity to develop a hepatic neoplasia.

The invention also provides method for identifying the prognosis of a subject having a hepatic neoplasia by detecting the level of miR-26 in a subject, wherein an decrease in the level of miR-26a level identifies the subject as having a poor prognosis. The subject having a poor prognosis is identified as in need of aggressive therapy.

The invention provides methods for selecting a therapy for a subject having a hepatic neoplasia by detecting miR-26 in a biological sample derived from the subject, wherein a decrease the level of miR-26 relative to a reference is indicative of the need for aggressive therapy.

The invention also provides methods of identifying an agent that treats or prevents a hepatic neoplasm by contacting a hepatic cell that expresses a miR-26 with an agent, and comparing the level of miR-26 expression in the hepatic cell contacted by the agent with the level of expression in a control cell, wherein an agent that increases miR-26a expression treats or prevents a neoplasm. The increase in expression, for example, is by at least about 5%, 10%, 20%, 30%, 40%, 50%, 60%, 70%, 80%, 90%, 100%, or more. Detection methods include, but are not limited to real time (RT)-PCR, polynucleotide hybridization, Northern blot, quantitative PCR, or ribonuclease protection assay.

In all of the diagnostic and prognostic methods of the invention, miR-26 microRNA is any or all of miR-26a-1 microRNA, miR-26a-2 microRNA, and miR-26b microRNA.

The invention provides compositions and methods featuring microRNAs for the diagnosis, treatment or prevention of hepatic neoplasia. Other features and advantages of the invention will be apparent from the detailed description, and from the claims.

DEFINITIONS

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "agent" is meant a polypeptide, polynucleotide, or fragment, or analog thereof, small molecule, or other biologically active molecule. An agent can be a previously known or unknown compound. As used herein, an agent is typically a non-cell based compound, however, an agent can include a biological therapeutic agent, e.g., peptide or nucleic acid therapeutic, e.g., cytokine, antibody, etc.

By "alteration" is meant a change (increase or decrease) in the expression levels of a polynucleotide or polypeptide as detected by standard art known methods such as those described above. As used herein, an alteration includes a 5% or 10% change, a 25% change, a 40% change, a 50%, a 100% change, or greater change, or any change within the range of the values provided, or range of changes bracketed by the values provided in expression levels, levels of any analyte for detection, proliferation or apoptosis rates, etc.

The term "amelioration" refers to a reduction of at least one sign and/or symptom of a specific disease or condition. Treatment refers to reduction of at least one sign and/or symptom of a disease or condition to reduce or eliminate at least one sign and/or symptom of the disease or condition, or to prevent progression of the disease or condition. Amelioration and treatment need not be considered separate interventions, but instead can be considered a continuum of therapeutic interventions.

As used herein, "changed as compared to a control reference sample" is understood as having a level or activity of an analyte, or in a whole organism change of physical characteristics or signs or symptoms of a disease, to be detected at a level that is statistically different than a sample from a normal, untreated, or control sample. Methods to select and test control samples are within the ability of those in the art. Control samples typically include a cell or an animal of the same type that has not been contacted with an active agent or been subjected to a particular treatment, and has optionally been contacted with a carrier or subjected to a sham treatment. Control samples also include a cell or an animal not subjected to an agent or treatment to induce a specific disease or condition.

The phrase "in combination with" is intended to refer to all forms of administration that provide a first agent together with a second agent, such as a second inhibitory nucleic acid molecule or a chemotherapeutic agent, where the two are administered concurrently or sequentially in any order. For two or more agents to be administered in combination with each other, the agents need not be administered simultaneously or in the same formulation. Agents administered in combination with each other simultaneously present or have biological activity in the subject to which the agents are delivered. Determination of the presence of a agent in a subject can be readily determined by empirical monitoring or by calculations using known pharmacokinetic properties of the agents.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

By "complementary" is meant capable of pairing to form a double-stranded nucleic acid molecule or portion thereof. In one embodiment, an inhibitory nucleic acid molecule is in large part complementary to a target sequence. The complementarity need not be perfect, but may include mismatches at 1, 2, 3, or more nucleotides.

"Contacting a cell" is understood herein as providing an agent to a cell, in culture or in an animal, such that the agent can interact with the surface of the cell, potentially be taken up by the cell, and have an effect on the cell. The agent can be delivered to the cell directly (e.g., by addition of the agent to culture medium or by injection into the cell or tissue of interest), or by delivery to the organism by an enteral or parenteral route of administration for delivery to the cell by circulation, lymphatic, or other means.

By "control" is meant a standard or reference condition.

By "corresponds" is meant comprising at least a fragment of a double-stranded gene, such that a strand of the double-stranded inhibitory nucleic acid molecule is capable of binding to a complementary strand of the gene.

By "decreases" is meant a reduction by at least about 5% relative to a reference level. A decrease may be by 5%, 10%, 15%, 20%, 25% or 50%, or even by as much as 75%, 85%, 95% or more, or any change within the range of the values provided, or range of changes bracketed by the values provided in expression levels or levels of any analyte for detection.

"Detect" refers to identifying the presence, absence or amount of the object to be detected. The amount detected can be none or below the level of detection.

By "detectable label" is meant a composition that when linked to a molecule of interest renders the latter detectable, preferably in a quantitative manner, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

The terms "disease" or "condition" are commonly recognized in the art and designate the presence of at least one sign and/or symptom in a subject or patient that are generally recognized as abnormal. Diseases or conditions may be diagnosed and categorized based on pathological changes (e.g., hyperproliferation). Signs may include any objective evidence of a disease such as changes that are evident by physical examination of a patient or the results of diagnostic tests that may include, among others, laboratory tests. Symptoms are subjective evidence of disease or a patient condition, e.g., the patient's perception of an abnormal condition that differs from normal function, sensation, or appearance, which may include, without limitations, physical disabilities, morbidity, pain, and other changes from the normal condition experienced by a subject.

By "an effective amount" is meant the amount of an agent required to ameliorate the symptoms of a disease relative to an untreated patient. The effective amount of active agent(s) used to practice the present invention for therapeutic treatment of a neoplasia varies depending upon the manner of administration, the age, body weight, and general health of the subject. Ultimately, the attending physician or veterinarian will decide the appropriate amount and dosage regimen. Such amount is referred to as an "effective" amount.

Thus, in connection with the administration of an agent which is "effective against" a disease or condition indicates that administration in a clinically appropriate manner results in a beneficial effect for at least a statistically significant fraction of patients, such as an improvement of symptoms, a cure, a reduction in at least one disease sign or symptom, extension of life, improvement in quality of life, or other effect generally recognized as positive by medical doctors familiar with treating the particular type of disease or condition. An agent can be effective against a specific disease or condition without being effective against the disease or condition for all subjects. Methods of selection of patient populations for treatment with the agents of the invention is an aspect of the invention.

The term "effective amount" refers to a dosage or amount that is sufficient to reduce, halt, or slow tumor progression to result in alleviation, lessening or amelioration of symptoms in a patient or to achieve a desired biological outcome, e.g., slow or stop tumor growth or reduction or disappearance of a tumor.

"Essentially" as used herein is understood as not departing from the fundamental nature or critical element of the method or agent.

By "fragment" is meant a portion (e.g., at least 10, 25, 50, 100, 125, 150, 200, 250, 300, 350, 400, or 500 amino acids or nucleic acids, or any lengths provided by the specific values or range of lengths bracketed by any of the values provided) of a protein or nucleic acid molecule that is substantially identical to a reference protein or nucleic acid and retains the biological activity of the reference.

By "hairpin form" is meant a microRNA that includes a double stranded portion.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

A "host cell" is any prokaryotic or eukaryotic cell that contains either a cloning vector or an expression vector. This term also includes those prokaryotic or eukaryotic cells that have been genetically engineered to contain the cloned gene(s) in the chromosome or genome of the host cell.

By "increases" is meant an increase by at least about 5% relative to a reference level. An increase may be by 5%, 10%, 15%, 20%, 25% or 50%, or even by as much as 75%, 85%, 95% or more, or any increase within the range of values bracketed by any of the values provided.

An agent that "increases the level of miR-26a" in a cell is, for example, a nucleic acid having a sequence of miR-26a itself, provided to the cell as an isolated nucleic acid, preferably a chemically modified nucleic acid, or mir-26a provided in an expression vector or construct to the cell to allow for expression of miR-26a in the cell. An agent that increases the level of miR-26a in the context of the invention can also be an agent that increases the expression, stability, or activity of miR-26a present in the cell. An increase is considered relative to the level of miR-26a expressed by the cell, or population of cells, prior to the cell being contacted with the agent. It is understood that a neoplastic cell having an increased level of miR-26a may have a lower level of miR-26a than a normal, non-neoplastic cell.

By "inhibits a neoplasia" is meant decreases the propensity of a cell to develop into a neoplasia or slows, decreases, or stabilizes the growth, proliferation, or metastasis of a neoplasia, or increases apoptosis.

As used herein, "isolated" or "purified" when used in reference to a polypeptide means that a naturally polypeptide has been removed from its normal physiological environment (e.g., protein isolated from plasma or tissue) or is synthesized in a non-natural environment (e.g., artificially synthesized in a heterologous system). Thus, an "isolated" or "purified" polypeptide can be in a cell-free solution or placed in a different cellular environment (e.g., expressed in a heterologous cell type). The term "purified" does not imply that the polypeptide or cell is the only polypeptide or cell present, but that it is essentially free (about 80-90%, or about 90-95%, up to 99-100% pure) of cellular or organismal material naturally associated with it, and thus is distinguished from naturally occurring polypeptide. "Isolated" when used in reference to a cell means the cell is in culture (i.e., not in an animal), either cell culture or organ culture, of a primary cell or cell line. Cells can be isolated from a normal animal, a transgenic animal, an animal having spontaneously occurring genetic changes, and/or an animal having a genetic and/or induced disease or condition. Isolated cells can be further modified to include reporter constructs or be treated with various stimuli to modulate expression of a gene of interest.

By "marker" is meant any polypeptide or polynucleotide having an alteration in expression level or activity that is associated with a disease or disorder.

By "mature form" is meant a microRNA that has, at least in part, been processed into a biologically active form that can participate in the regulation of a target mRNA.

By "microRNA" is meant a nucleobase sequence having biological activity that is independent of any polypeptide encoding activity. MicroRNAs may be synthetic or naturally occurring, and may include one or more modifications described herein. MicroRNAs include pri-microRNAs, hairpin microRNAs, and mature microRNAs.

By a "miR-26 microRNA" is meant at least one of or any combination of a miR-26a-1 microRNA, miR-26a-2 microRNA, and miR-26b microRNA. In an embodiment, a miR-26 is a human miR-26.

By "miR-26a-1 microRNA" is meant a nucleic acid molecule comprising a nucleobase sequence that is substantially identical to the sequence of hsa-mir-26a-1, MirBase Accession No. MI0000083, MIMAT0000082, or a fragment thereof whose expression reduces the growth of a neoplasia. The sequence of three exemplary mir-26a-1 microRNAs follow: 1-GUGGCCUCGU UCAAGUAAUCCAGGAUAGGCU- GUGCAGGUCCCAAUGGGCCUAUUCUG- GUACUGCAC GGGGACGC-71 (full length, SEQ ID NO: 1); 10-UUCAAGUAAUCCAGGAUAGGCU-31 (mature, SEQ ID NO: 2); and GUGGCCUCGUUCAAGUAAUC- CAGGAUAGG CUGUGCAG GUCCCAAUGGGCCUA- UUCUUGGUUACUUGCACGGGGACGC (hairpin, SEQ ID NO: 3).

By "miR-26a-1 gene" is meant a polynucleotide encoding a mir-26a-1 microRNA or an analog thereof.

By "miR-26a-2 microRNA" is meant a nucleic acid molecule comprising a nucleobase sequence that is substantially identical to the sequence of hsa-mir-26a-2, MirBase Accession No. MI0000750, MIMAT0000082, or a fragment thereof whose expression reduces the growth of a neoplasia. The sequence of three exemplary miR-26a-2 microRNA follows: 1-GGCUGUGGCU GGAUUCAAGUAAUCCAGGAUAG- GCUGUUUCCAUCUG UGAGGCCUAUUCUUGA- UUACUUGUUUCUGGAGGCA GCU-84 (full length, SEQ ID NO: 4) 14-UUCAAGUAAUCCAGGAUAGGCU-35 (mature, SEQ ID NO: 5) or GGCUGUGGCUGGAUU- CAAGUAAUCCAGGAUAGGCUGUUUCCAUCUGU GAGGCCUAUUCUUGAUUACUUGUUUCUG- GAGGCAGCU (hairpin, SEQ ID NO: 6).

By "miR-26a-2 gene" is meant a polynucleotide encoding a miR-26a-2 microRNA or an analog thereof.

Unless otherwise specified herein, miR-26a is understood to mean either one or both of miR-26a-1 and miR-26a-2. In preferred embodiments, miR-26a is a human miR-26a.

By "miR-26b microRNA" is meant a nucleic acid molecule comprising a nucleobase sequence that is substantially identical to the sequence of hsa-mir-26b, MirBase Accession No. MI0000084, MIMAT0000083, or a fragment thereof whose expression reduces the growth of a neoplasia. The sequence of three exemplary mir-26b microRNAs follow: 1-CCGG- GACCCAG UUCAAGUAAUUCAGGAUAGGUUGU- GUGCUGUCCAGCCUGUUCUCCAUU ACUUGGCUC GGGGACCGG-77 (full length, SEQ ID NO: 7); 12-UU- CAAGUAAUUCAGGAUGGU-33 (mature, SEQ ID NO: 8); and UUCAAGUAAUUCAGGAUAGGUUGU- GUGCUGUCCAG CCUGUUCUCCAUUACUUGGCUC (hairpin, SEQ ID NO: 9).

An expression vector including a miR-26a gene includes a sufficient portion of the miR-26a native coding sequence, with or without flanking sequences present in the genomic context of miR-26a, to produce a mature miR-26a to regulate expression of at least one miR-26a target (e.g., PTEN (phosphatase and tensin homolog; L-type voltage gated calcium channel; SMAD-1; cysteine and histidine-rich domain (CHORD)-containing 1; polymerase (RNA) III (DNA directed) polypeptide G (32 kD) or any other targets provided at http://targetscan.org/cgi-bin/vert_50/ targetscan.cgi?mirg=hsa-miR-26a on the date of filing of the priority document of the instant application) or reduces the growth of hepatic neoplasia. For example, a sufficient portion can include 21, 22, 23, 24, 25, 26, 27, 28, 29, 30, 35, 40, 45, 50, 55, 60, 65, 70, 75, 80, or 84 nucleotides, or any range of a combination of two values provided. A sufficient portion contains at least the sequence of the mature miR. In certain embodiments, a sufficient portion includes at least the hairpin sequence of the miR. In certain embodiments, a sufficient portion includes the full length miR. A sufficient portion can be determined using methods routine in the art. It is understood that a sequence encoding a miR-26a will be complementary to the RNA sequences provided and include T's rather than U's when the complementary DNA strand.

By "modification" or "chemically modification" and the like is meant any biochemical or other synthetic alteration of a nucleotide, amino acid, or other agent relative to a naturally occurring reference agent.

As used herein, "monitoring" is understood as observing a subject periodically, either at regular or irregular intervals, for the presence of one or more signs or symptoms of the disease from which the subject is suffering and for which the patient is to be, is undergoing, or has undergone treatment.

By "neoplasia" is meant any disease that is caused by or results in inappropriately high levels of cell division, inappropriately low levels of apoptosis, or both. For example, cancer is a neoplasia. Neoplasia includes solid tumors, e.g., hepatic tumors, and non-solid tumors or blood tumors, e.g., leukemia. Examples of cancers include, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, pancreatic ductal adenocarcinoma, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma). Lymphoproliferative disorders are also considered to be proliferative diseases.

By "nucleic acid" is meant an oligomer or polymer of ribonucleic acid or deoxyribonucleic acid, or analog thereof. This term includes oligomers consisting of naturally occurring bases, sugars, and intersugar (backbone) linkages as well as oligomers having non-naturally occurring portions which function similarly. Such modified or substituted oligonucleotides are often preferred over native forms because of properties such as, for example, enhanced stability in the presence of nucleases.

By "obtaining" as in "obtaining the inhibitory nucleic acid molecule" is meant synthesizing, purchasing, or otherwise acquiring the inhibitory nucleic acid molecule.

By "oligonucleotide" is meant any molecule comprising a nucleobase sequence. An oligonucleotide may, for example, include one or more modified bases, linkages, sugar moieties, or other modifications.

By "operably linked" is meant that a first polynucleotide is positioned adjacent to a second polynucleotide that directs transcription of the first polynucleotide when appropriate molecules (e.g., transcriptional activator or repressor proteins) are bound to the second polynucleotide.

The term "pharmaceutically-acceptable excipient" as used herein means one or more compatible solid or liquid filler, diluents or encapsulating substances that are suitable for administration into a human.

By "positioned for expression" is meant that the polynucleotide of the invention (e.g., a DNA molecule) is positioned adjacent to a DNA sequence that directs transcription and translation of the sequence (i.e., facilitates the production of, for example, a recombinant microRNA molecule described herein).

As used herein, the terms "prevent," "preventing," "prevention," "prophylactic treatment" and the like refer to reducing the probability of developing a disorder or condition in a subject, who does not have, but is at risk of or susceptible to developing a disorder or condition. Prevention can include administration of more than one dose of an agent. Prevention also includes delaying onset of a specific disease or condition and should not be understood as eliminating the disease for the lifetime of the subject.

"Probe set" or "primer set" means a set of oligonucleotides that may be used in any biochemical assay or procedure. Exemplary uses for probes/primers include detection of a target nucleic acid or in PCR, including quantitative PCR methods including real time (RT)-PCR sometimes referred to as qPCR. RT-PCR follows the general principle of polymerase chain reaction; its key feature is that the amplified DNA is detected as the reaction progresses in real time, a distinct approach compared to standard PCR, where the product of the reaction is detected at its end. Two common methods for detection of products in real-time PCR are: (1) non-specific fluorescent dyes that intercalate with any double-stranded DNA, and (2) sequence-specific DNA probes consisting of oligonucleotides that are labelled with a fluorescent reporter which permits detection only after hybridization of the probe with its complementary DNA target. Such methods are well known to those of skill in the art.

"Providing," refers to obtaining, by for example, buying or making the, e.g., cells, polypeptide, drug, polynucleotide, probe, and the like. The material provided may be made by any known or later developed biochemical or other technique.

By "reduces the survival" is meant increases the probability of cell death in a cell or population of cells relative to a reference. For example, a reduction in survival is measured in a cell treated with a microRNA of the invention relative to an untreated control cell. Cell death may be by any means, including apoptotic or necrotic cell death.

By "reduces cell division" is meant interferes with the cell cycle or otherwise reduces the growth or proliferation of a cell, tissue, or organ relative to a reference. For example, a reduction in cell division is measured in a cell treated with a microRNA of the invention relative to an untreated control cell.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. Reference sequences can commonly be found in databases, for example BLAST, SwissProt, miRBASE, and GenBank databases.

By "reporter gene" is meant a gene encoding a polypeptide whose expression may be assayed; such polypeptides include, without limitation, green fluorescent protein (GFP), glucuronidase (GUS), luciferase, chloramphenicol transacetylase (CAT), and beta-galactosidase.

"Double stranded RNAs" or "dsRNAs" can be introduced to an individual cell or to a whole animal; for example, they may be introduced systemically via the bloodstream. Such dsRNAs are delivered to cells for therapeutic uses. It is understood that a dsRNA includes both hairpin RNAs which include at least one double stranded portion or two separate RNA strands that may or may not be covalently linked by a non-nucleic acid linker so long as the linker does not alter the activity of the dsRNA. It is understood that dsRNAs can include one or more base mismatches. In a preferred embodiment, a dsRNA includes at least 3, 4, 5, 6, 7, 8, 9, or 10 contiguous complementary bases. Double stranded RNAs can include chemically modified RNAs.

A "sample" as used herein refers to a biological material that is isolated from its environment (e.g., blood or tissue from an animal, cells, or conditioned media from tissue culture) and is suspected of containing, or known to contain an analyte or other desired material. A sample can also be a partially purified fraction of a tissue or bodily fluid, e.g., from a subject having a specific disease or condition. A reference sample can be a "normal" sample, from a donor not having the disease or condition. A reference sample can also be from an untreated donor or cell culture not treated with an active agent (e.g., no treatment or administration of vehicle only) or not subjected to conditions to induce a disease state. A reference sample can also be taken at a "zero time point" prior to contacting the cell with the agent to be tested.

As used herein, "small molecule" is understood to refer to a chemical compound having a molecular weight below 2,000 daltons, more preferably between 300 and 1,000 daltons, and still more preferably between 400 and 700 daltons. It is preferred that these small molecules are organic molecules. In certain embodiments, "small molecule" does not include peptide or nucleic acid molecules.

By "specifically binds" is meant a molecule that recognizes and binds another molecule, e.g., protein or nucleic acid molecule of the invention, but which does not substantially recognize and bind other molecules in a sample, for example, a biological sample, which naturally includes a protein of the invention. Preferably, a first molecule that specifically binds a second molecule binds the second molecule with at least 10-, 100-, 500-, 1000-, 5000-, or 10,000-fold preference over a non-specific binding partner (e.g., BSA for proteins, random nucleic acid sequence).

The term "subject" is intended to include vertebrates, preferably a mammal, including human and non-human mammals such as non-human primates. Human subjects can be referred to as patients.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 .mu.g/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

A subject "suffering from or suspected of suffering from" a specific disease, condition, or syndrome has at least one risk factor and/or presents with at least one sign or symptom of the disease, condition, or syndrome such that a competent individual would diagnose or suspect that the subject was suffering from the disease, condition, or syndrome. Methods for identification of subjects suffering from or suspected of suffering from a hepatic neoplasia is within the ability of those in the art. Methods of identifying specific genetic or lifestyle predispositions to hepatic neoplasia are well within the ability of those of skill in the art. Subjects suffering from, and suspected of suffering from, a specific disease, condition, or syndrome are not necessarily two distinct groups.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, "tumorigenesis" is understood as the production of a new tumor or tumors; or the process involved in the production of a new tumor or tumors. Tumorigenesis as used herein includes both the generation of tumors de novo from normal cells and the generation of metastatic tumors from an established tumor.

By "vector" is meant a nucleic acid molecule, for example, a plasmid, cosmid, or bacteriophage, that is capable of replication in a host cell. In one embodiment, a vector is an expression vector that is a nucleic acid construct, generated recombinantly or synthetically, bearing a series of specified nucleic acid elements that enable transcription of a nucleic acid molecule in a host cell. Typically, expression is placed under the control of certain regulatory elements, including constitutive or inducible promoters, tissue-preferred regulatory elements, inverted terminal repeats, and enhancers.

Ranges provided herein are understood to be shorthand for all of the values within the range. For example, a range of 1 to 50 is understood to include any number, combination of numbers, or sub-range from the group including 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

"At least" a particular value is understood to mean that value or more. For example, "at least 2" is understood to be the same as "2 or more" i.e., 2, 3, 4, 5, 6, 7, 8, 9, 10, 11, 12, 13, 14, 15, etc.

"Less than" or "up to" and the like is understood as the range from zero up to and including the value provided. For example, "less than 10" or "up to 10" is understood as 0, 1, 2, 3, 4, 5, 6, 7, 8, 9, or 10.

Unless specifically stated or obvious from context, as used herein, the term "or" is understood to be inclusive.

Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

All references, patents, patent applications, and Accession Numbers as of the filing date of the priority application referred to herein are specifically incorporated by reference.

BRIEF DESCRIPTION OF THE DRAWINGS

FIG. 2. miR-26a induces a G1 arrest in human hepatocellular carcinoma cells (A) Northern blots documenting miRNA expression levels in normal liver and tumors from tet-o-MYC; LAP-tTA mice and in uninfected or retrovirally-infected HepG2 cells. tRNALys served as a loading control. (B) Cell-cycle profiles of retrovirally-infected HepG2 cells as determined by propidium-iodide (PI) staining and flow cytometry. Numbers over each histogram indicate the percentage of cells in G1, S, and G2 cell-cycle phases. (C) Cell-cycle profiles of retrovirally-infected HepG2 cells following treatment with nocodazole (Noc). Numbers over each histogram indicate the percentage of cells remaining in G1.

FIG. 6. miR-26a delivery induces tumor-specific cell-cycle arrest and apoptosis (A) Representative DAPI and Ki67-stained sections from miR-26a-treated and control tet-o-MYC; LAP-tTA animals 5 days after AAV administration showing tumors (outlined with dotted line) and adjacent normal-appearing liver. (B) Quantification of Ki67 staining in tumors from miR-26a-treated and control animals. Olympus Slidebook 4.2 was used to quantify the Ki67 fluorescence intensity in tumors in 3-5 randomly chosen fields per animal (n=2-4 animals per treatment per timepoint). The mean Ki67 fluorescence intensity per condition is plotted with error bars representing standard deviations. (C) Representative DAPI and TUNEL-stained sections from miR-26a-treated and control animals 5 days after AAV administration. Tumors are outlined with dotted lines. (D) Quantification of TUNEL staining in tumors from miR-26a-treated and control animals. ImageJ was used to quantify the TUNEL positive area in tumors in 6 randomly chosen fields per animal (n=2-4 animals per treatment per time-point). The mean TUNEL positive area per condition is plotted with error bars representing standard deviations. (E) Representative DAPI, Ki67, and TUNEL-stained sections from miR-26a-treated and control tet-o-MYC; LAP-tTA animals showing tumors (outlined with dotted line) and adjacent normal-appearing liver show cellular proliferation and apoptosis in tumors 10 days after AAV administration. (F) Representative DAPI, Ki67, and TUNEL-stained sections from miR-26a-treated and control tet-o-MYC; LAP-tTA animals showing tumors (outlined with dotted line) and adjacent normal-appearing liver show cellular proliferation and apoptosis in tumors 21 days after AAV administration. (G) Tissues were collected 21 days after AAV administration and stained with H&E, DAPI, or TUNEL for analysis of apoptosis in various tissues following AAV8-mediated delivery of miR-26a.

DETAILED DESCRIPTION OF THE INVENTION

Figure 1B:
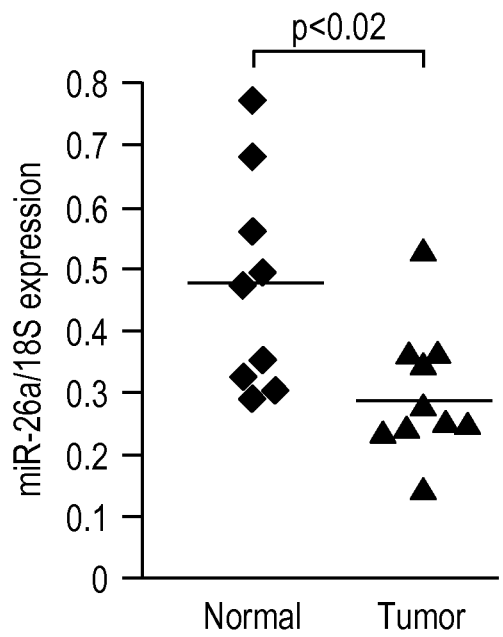
FIG. 1. (A) Dysregulated expression of miRNAs in liver tumors arising in tet-o-MYC; LAP-tTA mice Northern blot analysis of miRNA expression in normal liver (N) or tumor tissue (T) from mice of the indicated genotypes. Graphs depict relative quantification of miRNA levels normalized to tRNALys abundance. (B) qPCR analysis of miR26a expression in human HCC and normal liver biopsies. miRNA abundance was normalized to 18S rRNA expression. p value calculated by two-tailed t-test. (C) miR26a expression in individual HCC tumors relative to expression in paired normal liver samples.

The invention features compositions and methods that are useful for the diagnosis, treatment or prevention of a neoplasia.

Therapeutic strategies based on small RNA-guided gene regulatory pathways hold great promise for many diseases. The microRNA (miRNA) family of small RNAs is particularly attractive for these approaches due to the ability of these molecules to regulate complex gene expression networks and thereby profoundly influence cellular behavior. In this study, we investigated the efficacy of systemic miRNA administration for liver cancer therapy. We demonstrate that tumors in a mouse model of hepatocellular carcinoma (HCC) are characterized by reduced expression of miR-26a, a miRNA that is normally expressed at high levels in diverse tissues. Enforced expression of this miRNA in human HCC cells in vitro induces cell-cycle arrest associated with direct targeting of cyclins D2 and E2. Systemic delivery of this miRNA to tumor-bearing mice using adeno-associated virus (AAV) confers dramatic protection from disease progression without toxicity. These effects are associated with rapid and sustained inhibition of cancer cell proliferation and induction of tumor-specific apoptosis. These findings demonstrate the powerful anti-tumorigenic effects of miRNA administration and suggest that delivery of miRNAs that are highly expressed and therefore tolerated in normal tissues but lost in disease cells may provide a general strategy for highly-specific miRNA-based therapies.

Over the last five years, a particularly important role for miRNAs in cancer pathogenesis has emerged. Virtually all examined tumor types are characterized by globally abnormal miRNA expression patterns (Calin and Croce, 2006). Profiles of miRNA expression are highly informative for tumor classification, prognosis, and response to therapy. Moreover, recent results have documented a functional contribution of specific miRNAs to cellular transformation and tumorigenesis. For example, miRNAs are known targets of genomic lesions that frequently activate oncogenes and inactivate tumor suppressors in cancer cells such as amplification, deletion, and epigenetic silencing (Calin et al., 2004; Lujambio and Esteller, 2007; Zhang et al., 2006). Additionally, miRNAs provide critical functions downstream of classic oncogenic and tumor suppressor signaling pathways such as those controlled by Myc and p53 (Chang et al., 2008; He et al., 2007b; O'Donnell et al., 2005). Finally, functional studies have directly documented the potent pro- and anti-tumorigenic activity of specific miRNAs. The miR-17-92 cluster, a highly conserved group of six co-transcribed miRNAs, exemplifies a prototypical oncogenic miRNA locus (Mendell, 2008). Both amplification of the genomic interval that encodes these miRNAs as well as direct transactivation by the Myc oncogenic transcription factor contributes to widespread overexpression of these miRNAs in cancer (O'Donnell et al., 2005; Ota et al., 2004). Analysis of the miR-17-92 cluster in animal models reveals multiple pro-tumorigenic activities including induction of cellular proliferation and tumor angiogenesis and inhibition of apoptosis (Dews et al., 2006; He et al., 2005; Ventura et al., 2008; Xiao et al., 2008). In contrast, the miR-15a/16-1 cluster, located on human chromosome 13q14, represents one of the most highly characterized tumor suppressor miRNA loci. Deletion of these miRNAs occurs in multiple tumor types with especially high prevalence in chronic lymphocytic leukemia (CLL) (Calin et al., 2002). These miRNAs have been implicated as negative regulators of cell-cycle progression (Calin et al., 2008; Linsley et al., 2007), providing insight into the mechanisms through which their loss-of-function contributes to cancer cell proliferation.

As a consequence of the important functions provided by miRNAs in cancer cells, potential therapeutic approaches that target this pathway have recently attracted attention. Although significant focus in this area has been directed towards antisense-mediated inhibition of oncogenic miRNAs (Love et al., 2008; Stenvang et al., 2008), several lines of evidence suggest that miRNA replacement represents an equally viable if not more efficacious strategy. Although specific miRNAs are often overexpressed in cancer cells, most miRNAs are downregulated in tumors (Gaur et al., 2007; Lu et al., 2005). Global miRNA repression enhances cellular transformation and tumorigenesis in both in vitro and in vivo models (Kumar et al., 2007), underscoring the pro-tumorigenic effects of miRNA loss-of-function. Moreover, we have previously demonstrated that hyperactivity of Myc, a common occurrence in diverse tumor types, leads to widespread miRNA repression (Chang et al., 2008). Enforced expression of individual miRNAs in lymphoma cells transformed by Myc or other oncogenes dramatically suppresses tumorigenesis. These observations suggest that re-expression of even a single miRNA in tumor cells could provide significant therapeutic benefit. Supporting this notion, two recent reports demonstrated that viral delivery of let-7 miRNAs suppressed tumor growth in a mouse model of lung adenocarcinoma (Esquela-Kerscher et al., 2008; Kumar et al., 2008). Importantly, let-7 directly targets KRAS, the initiating oncogene in this tumor model (Johnson et al., 2005). Thus, the utility of miRNAs as more general anti-cancer therapeutics in situations where they do not target the initiating oncogene remains to be studied.

The liver is well-suited for delivery of nucleic acid therapeutics since it is easily targeted by both viral and non-viral gene and small-molecule delivery systems (Alexander et al., 2008; Pathak et al., 2008). In this regard, gene therapy vectors based on adeno-associated virus (AAV) are particularly promising. Recent advances in AAV vector technology include a self-complementary genome which enhances therapeutic gene expression and non-human primate AAV serotypes which facilitate efficient transduction following vascular delivery. Significantly, these improvements allow 90-100% transduction of hepatocytes and long-term gene expression without toxicity following a single systemic administration of recombinant virus (McCarty et al., 2003; Nakai et al., 2005; Rodino-Klapac et al., 2007; Wang et al., 2003). Due to their small size, regulatory RNAs are especially amenable to AAV-mediated delivery.

In this study, we tested the hypothesis that miRNAs can be used as general anti-cancer therapeutics through their effects on tumor cell proliferation and death even in situations where they do not target the initiating oncogene. We reasoned that the most therapeutically useful miRNAs would be expressed at low levels in tumors but would be highly expressed, and therefore tolerated, in normal tissues. Systemic delivery of such miRNAs might be expected to specifically affect cancer cell proliferation and survival. miR-26a fulfills these criteria, exhibiting high expression in normal adult liver but low expression in tumors in a mouse model of HCC. miR-26a directly downregulates cyclins D2 and E2 and induces a G1 arrest of human HCC cells in vitro. AAV-mediated miR-26a delivery potently suppresses cancer cell proliferation and activates tumor-specific apoptosis in vivo, resulting in dramatic suppression of tumor progression. These findings provide proof-of-concept support for systemic delivery of tumor-suppressing miRNAs as a powerful and highly specific anti-cancer therapeutic modality.

Since the initial discovery of a functional RNA interference (RNAi) system in mammals, significant effort has been devoted to the development of therapeutics that utilize this pathway (de Fougerolles et al., 2007). While progress has been made towards the design and delivery of short interfering (si) and short hairpin (sh) RNAs for therapeutic gene silencing, accumulating evidence indicates that delivery of miRNAs also represents an attractive strategy. miRNAs provide critical functions in development and normal physiology and are dysregulated in disease states (Ambros, 2004; Chang and Mendell, 2007). The modulation of miRNA activity therefore represents a potent method to broadly influence cellular behavior. Furthermore, as miRNAs often regulate extensive gene expression networks involving hundreds of transcripts (Baek et al., 2008; Selbach et al., 2008), therapeutic delivery of a single miRNA may affect many pathways simultaneously to achieve clinical benefit. In this study, we have investigated the potential efficacy of miRNA delivery for liver cancer therapy. We show that miR-26a directly regulates the G1-S cell-cycle transition and has potent anti-proliferative effects in human HCC cells in vitro. Direct downregulation of cyclins D2 and E2 by this miRNA likely contributes to its anti-proliferative properties. Furthermore, systemic viral delivery of miR-26a dramatically suppresses tumorigenesis in a mouse model of HCC by inhibiting cancer cell proliferation and inducing tumor-specific apoptosis. The potency of these effects in suppressing even a severe, multifocal model of carcinogenesis in the absence of overt toxicity provides proof-of-principle that the systemic administration of miRNAs may be a clinically viable anti-cancer therapeutic strategy.

Thus far, most translational in vivo studies targeting miRNAs have aimed to inhibit miRNA function through the use of antisense reagents such as antagomirs, locked nucleic acid (LNA) oligomers, and other modified oligonucleotides (Elmen et al., 2008; Esau et al., 2006; Krutzfeldt et al., 2005). One of these strategies has been validated in a non-human primate model, where administration of the inhibitor led to long-lasting but reversible inhibition of miRNA function (Elmen et al., 2008). While the in vivo use of synthetic oligonucleotide inhibitors is promising and will no doubt remain a fruitful area of investigation, the therapeutic delivery of miRNAs has certain advantages, especially in cancer. It has been demonstrated that most tumors are characterized by globally diminished miRNA expression (Gaur et al., 2007; Lu et al., 2005) and that experimental impairment of miRNA processing enhances cellular transformation and tumorigenesis (Kumar et al., 2007). Additionally, common oncogenic lesions can result in widespread miRNA repression (Chang et al., 2008). Thus, miRNA delivery might allow the therapeutic restitution of physiological programs of regulation lost in cancer and other disease states.

Therapeutic miRNA delivery may also have unique technical advantages. First, the risk of off-target gene silencing is likely to be lower than that associated with artificial RNAi triggers since physiologic gene expression networks have evolved to accommodate the regulatory effects of endogenous miRNAs. Second, as compared to siRNAs or shRNAs that target a single transcript, the regulation of hundreds of targets in multiple pathways by miRNAs may reduce the emergence of resistant clones in diseases such as cancer since many simultaneous mutations would be required to subvert the effects of miRNA expression. At the same time, however, miRNA-based therapies will require thorough pre-clinical validation as these broad effects may in some cases have toxic consequences. Nevertheless, carefully selected exogenously delivered miRNAs might be better tolerated than some artificial RNAi triggers. It has been previously shown that the miRNA biogenesis pathway can be competitively inhibited by the expression of certain shRNAs, resulting in toxic effects following delivery of these transcripts (Grimm et al., 2006). This may be due to inefficient processing and/or nuclear-cytoplasmic transport of shRNA sequences which are not evolutionarily adapted for precise handling by this pathway. Supporting this notion, shRNA-associated toxicity can be mitigated by placing a shRNA into a miRNA-like context (McBride et al., 2008). Indeed, in this study we demonstrated high expression of an exogenously supplied natural miRNA without effects on endogenous miRNA biogenesis or other overt signs of toxicity.

In this study, we elected to use an AAV-based vector system, an especially attractive platform for regulatory RNA delivery (Franich et al., 2008; Giering et al., 2008; Grimm and Kay, 2007; McCarty, 2008). When delivered in viral vectors, miRNAs are continually transcribed, allowing sustained high level expression in target tissues without the need for repeated dosing. Additionally, the use of tissue-specific promoters could restrict this expression to particular cell types of interest even with systemic delivery of the virus. Compared to retroviral delivery systems, DNA viruses such as AAV carry substantially diminished risk of insertional mutagenesis since viral genomes persist primarily as episomes (Schnepp et al., 2003). Further, the availability of multiple AAV serotypes allows efficient targeting of many tissues of interest (Gao et al., 2002; McCarty, 2008). Finally, the general safety of AAV has been well documented, with clinical trials using this platform already underway (Carter, 2005; Maguire et al., 2008; Park et al., 2008).

Two groups recently demonstrated the potential of miRNA delivery for cancer therapy in vivo using a KRAS-driven mouse model of lung adenocarcinoma and the let-7 family of miRNAs (Esquela-Kerscher et al., 2008; Kumar et al., 2008). These studies built upon the observation that this miRNA family regulates KRAS by demonstrating reduced tumor burden following lentiviral or adenoviral administration of let-7. We have extended these findings in several important and novel ways. Our results demonstrate for the first time that therapeutic delivery of a miRNA can result in tumor suppression even in a setting where the initiating oncogene is not targeted. This establishes the principle that miRNAs may be useful as anti-cancer agents through their ability to broadly regulate cancer cell proliferation and survival. Furthermore, in the earlier work, tumor initiation and miRNA administration occurred simultaneously. Here we treated existing tumors with a miRNA, a setting more closely related to the clinical scenarios in which such therapies would be employed. Finally, we demonstrate highly specific effects of miRNA delivery on tumor cells without affecting surrounding normal tissue. Although the molecular basis of this specificity requires further investigation, it is likely that the high physiologic expression of miR-26a in normal hepatocytes confers tolerance to exogenous administration of this miRNA. In contrast, the specific reduction of miR-26a in neoplastic cells and their sensitivity to its restored expression underscores the contribution of loss-of-function of this miRNA to tumorigenesis in this setting. It is noteworthy that large scale cloning efforts have documented expression of miR-26a in most mouse and human tissues (Landgraf et al., 2007), while in situ hybridization data from zebrafish has documented ubiquitous expression with especially high levels in the head, spinal cord, and gut (Wienholds et al., 2005). The widespread expression of this miRNA is consistent with our observation that systemic AAV-mediated delivery of miR-26a is well-tolerated by many tissues.

We have previously documented that miR-26 family members suppress tumorigenesis in c-Myc-driven B lymphoma cells (Chang et al., 2008) and now extend these findings to the tet-o-MYC; LAP-tTA HCC model. Our demonstration that a genetically complex human HCC cell line is also susceptible to miR-26a-mediated anti-proliferative effects suggests that the tumor suppressive activities of this miRNA are not limited to Myc-initiated malignancies. Several additional lines of evidence further support this notion. Work from our group and others has revealed a role for miR-26a in the p53 tumor suppressor network as this miRNA is upregulated in a p53-dependent manner following DNA damage (Chang et al., 2007; Xi et al., 2006). Additionally, a profiling study of human anaplastic thyroid cancers (ATC) identified miR-26a as consistently downregulated and demonstrated that transient transfection of this miRNA significantly impairs proliferation of ATC cells in vitro (Visone et al., 2007). Moreover, the miR-26a-1-encoding locus at 3p21.3 is contained within a sub-megabase interval that is frequently deleted in small cell lung carcinomas, renal cell carcinomas, and breast carcinomas (Kashuba et al., 2004). These observations suggest broad anti-tumorigenic properties of miR-26 family members in diverse settings. Nevertheless, if future work reveals that the effectiveness of miR-26 delivery is restricted to settings of Myc dysregulation, therapeutic delivery of this miRNA may still be beneficial for a large number of cancer subtypes since hyperactivity of Myc is one of the most common attributes of human cancer cells.

Modified Nucleic Acid Molecules

A desirable nucleic acid molecule for administration as a therapeutic agent includes one or more chemical modifications to improve pharmacokinetic and pharmacodynamic properties for example by increasing nuclease resistance or altering protein binding in serum. Therapeutic nucleic acids for delivery in the methods of the invention include double stranded nucleic acids that may be composed of two independent strands, or of a single nucleic acid folded over to create a hairpin having at least one double stranded portion. A hairpin nucleic acid can be understood to have a first annealed portion which can be considered as a first strand and a second annealed portion which can be considered a second strand even though the annealed portions are covalently joined. Similarly, two nucleic acid portions can be covalently or non-covalently linked by a non-nucleic acid linker and be understood to have a first strand and a second strand. It is understood that the two strands of a nucleic acid molecule can be asymmetrically modified. For example, it is understood that asymmetric modification of dsRNA compounds can promote loading into Drosha and Dicer improving processing (see, e.g., US2008146788).

Specific motifs have been identified that promote cleavage by Drosha (see, e.g., US Patent Publication 20060073505 which is incorporated herein by reference). The publication teaches the preparation of oligomeric compound including: a first region having at least one nucleobase that forms a first 5' helical region with a target mRNA; a second region having one or two mismatched nucleobases that forms a 5' destabilizing region with the target mRNA; a third region having seven or eight nucleobases that forms a second 5' helical region with the target mRNA; a fourth region having two mismatched nucleobases that forms a cleavage signal region with the target mRNA; a fifth region having four nucleobases that forms a cleavage site region with the target mRNA; a sixth region having one or two mismatched nucleobases that form a 3' destabilizing region with the target mRNA; and a seventh region having at least three nucleobases that forms a 3' helical region with the target mRNA. In some embodiments, the first region includes at least two nucleobases. In some embodiments, the second region includes one nucleobases such as one that forms a pyrimidine/pyrimidine, A/C, or A/A mismatched base pair with the target mRNA. In some embodiments, the third region includes seven nucleobases. In some embodiments, the third region does not include a G/U base pair with the target mRNA. In some embodiments, the fourth region includes a UU/UC, GG/AG, AG/AG, CA/CC, UG/CU, CU/CC, UA/GC, UC/UU, or UU/G-mismatched base pair with the target mRNA. In some embodiments, the sixth region includes two nucleobases. In some embodiments, the sixth region includes a GA/GG mismatched base pair with the target mRNA. In other embodiments, the sixth region includes one nucleobases, such as a C/C mismatched base pair with the target mRNA. In some embodiments, the fifth region includes at least one G/U base pair with the target mRNA. In some embodiments, the oligomeric compound includes from about 13 to about 80 nucleobases, from about 13 to about 50 nucleobases, from about 18 to about 30 nucleobases, from about 19 to about 25 nucleobases, or from about 19 to about 22 nucleobases. In some embodiments, the oligomeric compound includes at least one nucleobase that comprises a 2'-O—CH$_2$CH$_2$OCH$_3$ modification. In some embodiments, the oligomeric compound is a gapmer including three nucleobases phosphorothioate wings and a phosphodiester gap, wherein each nucleobase within the wings comprises a 2'-O—CH$_2$CH$_2$OCH$_3$ modification.

MicroRNAs are processed by Dicer as well as Drosha. Dicer substrates, including chemically modified Dicer substrates are taught, for example, in US Patent Publications 20050277610 and 20050244858, both of which are incorporated herein by reference. The Dicer substrates include dsRNA has a length sufficient such that it is processed by Dicer to produce a double stranded RNA having at least one of the following properties: (a) the dsRNA is asymmetric, e.g., has a 3' overhang on the antisense strand and (b) the dsRNA has a modified 3' end on the sense strand to direct orientation of Dicer binding and processing of the dsRNA to an active siRNA. According to this embodiment, the sense strand comprises 22-28 nucleotides and the antisense strand comprises 24-30 nucleotides. In one embodiment, the dsRNA has an overhang on the 3' end of the antisense strand. In another embodiment, the sense strand is modified for Dicer binding and processing by suitable modifiers located at the 3' end of the sense strand. Suitable modifiers include nucleotides such as deoxyribonucleotides, acyclonucleotides and the like and sterically hindered molecules, such as fluorescent molecules and the like. When nucleotide modifiers are used, they replace ribonucleotides in the dsRNA such that the length of the dsRNA does not change. In another embodiment, the dsRNA has an overhang on the 3' end of the antisense strand and the sense strand is modified for Dicer processing. In another embodiment, the 5' end of the sense strand has a phosphate. The sense and antisense strands anneal under biological conditions, such as the conditions found in the cytoplasm of a cell. In addition, a region of one of the sequences, particularly of the antisense strand, of the dsRNA has a sequence length of at least 19 nucleotides, wherein these nucleotides are in the 21-nucleotide region adjacent to the 3' end of the antisense strand and are sufficiently complementary to a nucleotide sequence of the RNA produced from the target gene. Further, the Dicer substrate may also have one or more of the following additional properties: (a) the antisense strand has a right shift from the typical 21mer (i.e., the antisense strand includes nucleotides on the right side of the molecule when compared to the typical 21mer), (b) the strands may not be completely complementary, i.e., the strands may contain simple mismatch pairings and (c) base modifications such as locked nucleic acid(s) may be included in the 5' end of the sense strand. The Dicer substrates can also include one or more chemical base, sugar, and/or backbone modification such as those described herein, wherein the chemical modification does not disrupt processing of the precursor by Dicer.

Nucleic acid molecules of the invention can include other modifications such as modified backbones or non-natural internucleoside linkages. Oligomers having modified backbones include those that retain a phosphorus atom in the backbone and those that do not have a phosphorus atom in the backbone, or that have a mixed backbone. For the purposes of this specification, modified oligonucleotides that do not have a phosphorus atom in their internucleoside backbone are also considered to be nucleobase oligomers. Nucleobase oligomers that have modified oligonucleotide backbones include, for example, phosphorothioates, chiral phosphorothioates, phosphorodithioates, phosphotriesters, aminoalkyl-phosphotriesters, methyl and other alkyl phosphonates including 3'-alkylene phosphonates and chiral phosphonates, phosphinates, phosphoramidates, thionophosphoramidates, thionoalkylphosphonates, thionoalkylphosphotriesters, and boranophosphates. Various salts, mixed salts and free acid forms are also included. Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

Nucleobase oligomers having modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, 0, S and CH$_2$ component parts. Representative United States patents that teach the preparation of the above oligonucleotides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

Nucleobase oligomers may also contain one or more substituted sugar moieties. Such modifications include 2'-O-methyl and 2'-methoxyethoxy modifications. Another desirable modification is 2'-dimethylaminooxyethoxy, 2'-aminopropoxy, and 2'-fluoro. Similar modifications may also be made at other positions on an oligonucleotide or other nucleobase oligomer, particularly the 3' position of the sugar on the 3' terminal nucleotide. Nucleobase oligomers may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

In other nucleobase oligomers, both the sugar and the internucleoside linkage, i.e., the backbone, are replaced with novel groups. The nucleobase units are maintained for hybridization with a nucleic acid molecule of a microRNA described herein. Methods for making and using these nucleobase oligomers are described, for example, in "Peptide Nucleic Acids (PNA): Protocols and Applications" Ed. P. E. Nielsen, Horizon Press, Norfolk, United Kingdom, 1999. Representative United States patents that teach the preparation of PNAs include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

It is understood that the strands of the double stranded portion of the oligomer to be delivered can be modified asymmetrically. For example, modification of a single strand can promote specific orientation of the double stranded oligonucleotide into processing enzymes such as Drosha or Dicer.

Polynucleotides of the Invention

In general, the invention includes any nucleic acid sequence encoding a miR-26 microRNA provided herein, that is a miR-26a-1, a miR-26a-2, or a miR26b microRNA, or any combination thereof. The synthetic nucleic acid molecules of the invention can be between 13 and 80 nucleotides in length, or even longer. In some embodiments, the inhibitory nucleic acid molecules of the invention comprises 13, 15, 16, 17, 18, 19, 20, 21, 22, 23, 24, 25, 26, 27, 28, 29, 30, 31, 32, 33, 34, 35, 45, 50, 55, 60, 65, 70, 75, or 80 or range of lengths bracketed by any of the values provided. An isolated nucleic acid molecule can be manipulated using recombinant DNA techniques well known in the art. Thus, a nucleotide sequence contained in a vector in which 5' and 3' restriction sites are known, or for which polymerase chain reaction (PCR) primer sequences have been disclosed, is considered isolated, but a nucleic acid sequence existing in its native state in its natural host is not. An isolated nucleic acid may be substantially purified, but need not be. For example, a nucleic acid molecule that is isolated within a cloning or expression vector may comprise only a tiny percentage of the material in the cell in which it resides. Such a nucleic acid is isolated, however, as the term is used herein, because it can be manipulated using standard techniques known to those of ordinary skill in the art.

Delivery of Nucleobase Oligomers

Naked oligonucleotides, such as a synthetic miR-26, that is a miR-26a-1, a miR-26a-2, or a miR26b microRNA, or any combination thereof, are capable of entering tumor cells (see, e.g., U.S. Pat. No. 6,784,290, incorporated herein by reference). Nonetheless, it may be desirable to utilize a formulation that aids in the delivery of nucleobase oligomers to cells (see, e.g., U.S. Pat. Nos. 5,656,611, 5,753,613, 5,785,992, 6,120,798, 6,221,959, 6,346,613, 6,353,055, and 7,470,781 each of which is hereby incorporated by reference). Further, covalent modification of oligomers has been demonstrated to be useful for delivery of nucleic acids to cells (see, e.g., U.S. Pat. Nos. 6,153,737, 6,753,423, 6,576,752, and 6,878,805).

Polynucleotide Therapy

The invention provides polynucleotide therapy useful for increasing the expression of microRNA miR-26, that is a miR-26a-1, a miR-26a-2, or a miR26b microRNA, or any combination thereof for the treatment of hepatic cancers. Expression vectors encoding a desired sequence (e.g. encoding a microRNA) can be delivered to cells of a subject having a hepatic neoplasia. The nucleic acid molecules must be delivered to the cells of a subject in a form in which they can be taken up and are advantageously expressed so that therapeutically effective levels can be achieved.

Methods for delivery of the polynucleotides to the cell according to the invention include using a delivery system such as liposomes, polymers, microspheres, gene therapy vectors, and naked DNA vectors.

Transducing viral (e.g., retroviral, adenoviral, lentiviral and adeno-associated viral) vectors can be used for somatic cell gene therapy, especially because of their high efficiency of infection and stable integration and expression (see, e.g., Cayouette et al., Human Gene Therapy 8:423-430, 1997; Kido et al., Current Eye Research 15:833-844, 1996; Bloomer et al., Journal of Virology 71:6641-6649, 1997; Naldini et al., Science 272:263-267, 1996; and Miyoshi et al., Proc. Natl. Acad. Sci. U.S.A. 94:10319, 1997). For example, a polynucleotide encoding an nucleic acid molecule can be cloned into a retroviral vector and expression can be driven from its endogenous promoter, from the retroviral long terminal repeat, or from a promoter specific for a target cell type of interest. Other viral vectors that can be used include, for example, a vaccinia virus, a bovine papilloma virus, or a herpes virus, such as Epstein-Ban Virus (also see, for example, the vectors of Miller, Human Gene Therapy 15-14, 1990; Friedman, Science 244:1275-1281, 1989; Eglitis et al., BioTechniques 6:608-614, 1988; Tolstoshev et al., Current Opinion in Biotechnology 1:55-61, 1990; Sharp, The Lancet 337:1277-1278, 1991; Cornetta et al., Nucleic Acid Research and Molecular Biology 36:311-322, 1987; Anderson, Science 226:401-409, 1984; Moen, Blood Cells 17:407-416, 1991; Miller et al., Biotechnology 7:980-990, 1989; Le Gal La Salle et al., Science 259:988-990, 1993; and Johnson, Chest 107:77S-83S, 1995). Retroviral vectors are particularly well developed and have been used in clinical settings (Rosenberg et al., N. Engl. J. Med 323:370, 1990; Anderson et al., U.S. Pat. No. 5,399,346). Viral vectors are preferably replication incompetent in the cells to which they are delivered for therapeutic applications. However, replication competent viral vectors are known.

Preferred viral vectors for use in the invention include AAV vectors, e.g. AAV serotypes 1, 2, 3, 4, 5, 6, 7, 8, and/or 9, including chimeric AAV vectors. The availability of multiple AAV serotypes allows efficient targeting of many tissues of interest (Gao et al., 2002; McCarty, 2008; US Patent Publications 2008075737, 20080050343, 20070036760, 20050014262, 20040052764, 20030228282, 20030013189, 20030032613, and 20020019050 each incorporated herein by reference). In preferred embodiments, the invention includes the use of self-complementary (sc) AAV vectors which are described, for example, in US Patent Publications 20070110724 and 20040029106, and U.S. Pat. Nos. 7,465,583 and 7,186,699 (all of which are incorporated by reference). Further, the general safety of AAV has been well documented, with clinical trials using AAV platforms are already underway (Carter, 2005; Maguire et al., 2008; Park et al., 2008; all of which are incorporated by reference).

Non-viral approaches can also be employed for the introduction of a therapeutic nucleic acid molecule to a cell of a patient diagnosed as having a hepatic neoplasia. For example, an expression vector that encodes a miR-26a microRNA can be introduced into a cell by administering the nucleic acid in the presence of lipofection (Feigner et al., Proc. Natl. Acad. Sci. U.S.A. 84:7413, 1987; Ono et al., Neuroscience Letters 17:259, 1990; Brigham et al., Am. J. Med. Sci. 298:278, 1989; Staubinger et al., Methods in Enzymology 101:512, 1983), asialoorosomucoid-polylysine conjugation (Wu et al., Journal of Biological Chemistry 263:14621, 1988; Wu et al., Journal of Biological Chemistry 264:16985, 1989), or by micro-injection under surgical conditions (Wolff et al., Science 247:1465, 1990). Preferably the nucleic acid molecules are administered in combination with a liposome and protamine.

Gene transfer can also be achieved using non-viral means involving transfection in vitro. Such methods include the use of calcium phosphate, DEAE dextran, electroporation, and protoplast fusion. Liposomes can also be potentially beneficial for delivery of DNA into a cell.

Nucleic acid molecule expression for use in polynucleotide therapy methods can be directed from any suitable promoter (e.g., the human cytomegalovirus (CMV), simian virus 40 (SV40), metallothionein, U1a1 snRNA, U1b2 snRNA, histone H2, and histone H3 promoters), and regulated by any appropriate mammalian regulatory element. Hepatic cancer may be treated, for example, by expressing miR-26a using a tissue-specific or ubiquitously expressed promoter. Tissue specific promoters useful for the treatment of hepatic cancer include, but are not limited to, the hepatocyte-specific promoter element (HP1) promoter (Kugler et al., NAR, 16: 3165-3174, 1988, incorporated herein by reference), human alpha 1-antitrypsin (hAAT) promoter, the 810-bp mouse albumin (mAlb) promoter (Hafenrichter et al., Blood, 84: 3394-3404. 1994, incorporated herein by reference). Other promoters expressed in hepatic cancer cells include Terminal minimal enhancer/promoter, antitrypsin promoter, human factor IX pr/liver transcription factor-responsive oligomers, LSP, and basic albumin promoter (Wu et al, Mol. Ther. 16:280-289, 2008). Cancer-specific promoters are described, for example, in U.S. Patent Publication No. 20080286860, which is incorporated herein by reference in its entirety. For example, if desired, enhancers known to preferentially direct gene expression in specific cell types can be used to direct the expression of a nucleic acid. The enhancers used can include, without limitation, those that are characterized as tissue- or cell-specific enhancers.

For any particular subject, the specific dosage regimes should be adjusted over time according to the individual need and the professional judgment of the person administering or supervising the administration of the compositions.

Pharmaceutical Compositions

As reported herein, agents that increase miR-26 levels, that is levels of a miR-26a-1, a miR-26a-2, or a miR26b microRNA, or any combination thereof, by delivery of a miR-26 to a cell or increasing the level of a miR-26 from an endogenous promoter, or increasing the activity of a miR-26 present in the cell, are useful alone for the treatment of cancer. If desired, such agents are administered in combination with a chemotherapeutic agent. Agents of the invention may be administered as part of a pharmaceutical composition. The compositions should be sterile and contain a therapeutically effective amount of the agents in a unit of weight or volume suitable for administration to a subject.

Polynucleotides of the invention may be administered within a pharmaceutically-acceptable diluent, carrier, or excipient, in unit dosage form. Conventional pharmaceutical practice may be employed to provide suitable formulations or compositions to administer the compounds to patients suffering from a hepatic neoplasia (i.e., liver cancer). Administration may begin before the patient is symptomatic. Any appropriate route of administration may be employed, for example, administration may be parenteral, intravenous, intraarterial, subcutaneous, intratumoral, intramuscular, intracranial, intraorbital, ophthalmic, intraventricular, intrahepatic, intracapsular, intrathecal, intracisternal, intraperitoneal, intranasal, aerosol, suppository, or oral administration. For example, therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found, for example, in "Remington: The Science and Practice of Pharmacy" Ed. A. R. Gennaro, Lippincourt Williams & Wilkins, Philadelphia, Pa., 2000. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for inhibitory nucleic acid molecules include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

The formulations can be administered to human patients in therapeutically effective amounts (e.g., amounts which prevent, eliminate, or reduce a pathological condition) to provide therapy for a neoplastic disease or condition. The preferred dosage of a therapeutic agent of the invention is likely to depend on such variables as the type and extent of the disorder, the overall health status of the particular patient, the formulation of the compound excipients, and its route of administration.

With respect to a subject having a neoplastic disease or disorder, an effective amount is sufficient to stabilize, slow, or reduce the proliferation or metastasis of the neoplasm. Generally, doses of active polynucleotide compositions of the present invention would be from about 0.01 mg/kg per day to about 1000 mg/kg per day. It is expected that doses ranging from about 50 to about 2000 mg/kg will be suitable. Lower doses will result from certain forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of a therapeutic polynucleotide.

It is anticipated that AAV DNase resistant particle vector doses could vary between $10^9$ DRP/kg–$2\times10^{13}$ DRP/kg per patient (approximately $10^{11}$–$10^{15}$ total DRP per patient) depending on disease indication and route of delivery. Frequency could vary widely from monthly intervals to once in every few years (1-5). Administration of viral vectors may occur in the presence of immuosupressive drugs like MMF, Cyclosporin etc. Such considerations are well understood by those of skill in the art.

A variety of administration routes are available. The methods of the invention, generally speaking, may be practiced using any mode of administration that is medically acceptable, meaning any mode that produces effective levels of the active compounds without causing clinically unacceptable adverse effects. Other modes of administration include intravenous, oral, rectal, topical, intraocular, buccal, intravaginal, intracisternal, intracerebroventricular, intratracheal, intraheptaic (i.e., via portal vein), intranasal, transdermal, within/on implants, e.g., fibers such as collagen, osmotic pumps, or grafts comprising appropriately transformed cells, etc., or parenteral routes. Injectable drugs can be delivered as a bolus or by infusion at any desired rate.

Therapy

Therapy may be provided wherever cancer therapy is performed: at home, the doctor's office, a clinic, a hospital's outpatient department, or a hospital. Treatment generally begins at a hospital so that the doctor can observe the therapy's effects closely and make any adjustments that are needed. The duration of the therapy depends on the kind of cancer being treated, the age and condition of the patient, the stage and type of the patient's disease, and how the patient's body responds to the treatment. Drug administration may be performed at different intervals (e.g., daily, weekly, monthly, or yearly). Therapy may be given in on-and-off cycles that include rest periods so that the patient's body has a chance to build healthy new cells and regain its strength.

Depending on the type of cancer and its stage of development, the therapy can be used to slow the spreading of the cancer, to slow the cancer's growth, to kill or arrest cancer cells that may have spread to other parts of the body from the original tumor, to relieve symptoms caused by the cancer, or to prevent cancer in the first place. As described above, if desired, treatment with a therapeutic polynucleotide or an inhibitory nucleic acid molecule of the invention may be combined with therapies for the treatment of proliferative disease (e.g., radiotherapy, surgery, or chemotherapy). For any of the methods of application described above, an inhibitory nucleic acid molecule of the invention is desirably administered intravenously or is applied to the site of neoplasia (e.g., by injection).

Diagnostics

As described in more detail below, the present invention has identified decreased levels of miR-26, that is a miR-26a-1, a miR-26a-2, or a miR26b microRNA, or any combination thereof, being associated with hepatic neoplasia.

In one embodiment, a subject is diagnosed as having or having a propensity to develop a hepatic neoplasia, the method comprising measuring miR-26 in a biological sample from a patient, that is a miR-26a-1, a miR-26a-2, or a miR26b microRNA, or any combination thereof, and detecting a decrease in the expression of test marker molecules relative to the sequence or expression of a reference molecule being indicative of hepatic neoplasia, that is a miR-26a-1, a miR-26a-2, or a miR26b microRNA, or any combination thereof.

In one approach, diagnostic methods of the invention are used to assay the expression of a miR-26, that is a miR-26a-1, a miR-26a-2, or a miR26b microRNA, or any combination thereof, in a biological sample relative to a reference (e.g., the level of microRNA present in a corresponding control tissue). In one embodiment, the level of a miR-26, that is a miR-26a-1, a miR-26a-2, or a miR26b microRNA, or any combination thereof, is detected using a nucleic acid probe that specifically binds the microRNA. By "nucleic acid probe" is meant any nucleic acid molecule, or fragment thereof, that binds a microRNA. Such nucleic acid probes are useful for the diagnosis of a hepatic neoplasia. The specificity of the probe determines whether the probe hybridizes to a naturally occurring sequence, allelic variants, or other related sequences. Hybridization techniques may be used to identify mutations indicative of a neoplasia or may be used to monitor expression levels of this miR (for example, by Northern analysis (Ausubel et al., supra).

In another approach, quantitative PCR methods are used to identify an alteration in the expression of miR-26, that is a miR-26a-1, a miR-26a-2, or a miR26b microRNA, or any combination thereof. In another approach, PCR methods are used to identify an alteration in the sequence of miR-26, that is a miR-26a-1, a miR-26a-2, or a miR26b microRNA, or any combination thereof.

In general, the measurement of a nucleic acid molecule in a subject sample is compared with a diagnostic amount present in a reference. A diagnostic amount distinguishes between a neoplastic tissue and a control tissue. The skilled artisan appreciates that the particular diagnostic amount used can be adjusted to increase sensitivity or specificity of the diagnostic assay depending on the preference of the diagnostician. In general, any significant increase or decrease (e.g., at least about 5%, 10%, 15%, 30%, 50%, 60%, 75%, 80%, or 90%) in the level of test nucleic acid molecule or polypeptide in the subject sample relative to a reference may be used to diagnose a neoplasia. Test molecules include miR-26, that is a miR-26a-1, a miR-26a-2, or a miR26b microRNA, or any combination thereof. In one embodiment, the reference is the level of test polypeptide or nucleic acid molecule present in a control sample obtained from a patient that does not have a hepatic neoplasia. In another embodiment, the reference is a baseline level of test molecule present in a biologic sample derived from a patient prior to, during, or after treatment for a hepatic neoplasia. In yet another embodiment, the reference can be a standardized curve.

Types of Biological Samples

The level of markers in a biological sample from a patient having or at risk for developing a hepatic neoplasia can be measured, and an alteration in the expression of test marker molecule such as miR-26, that is a miR-26a-1, a miR-26a-2, or a miR26b microRNA, or any combination thereof, relative to the sequence or expression of a reference molecule, can be determined in different types of biologic samples. The biological samples are generally derived from a patient, preferably as a bodily fluid (such as blood, cerebrospinal fluid, phlegm, saliva, or urine) or tissue sample (e.g. a tissue sample obtained by biopsy particularly a hepatic biopsy).

Therapy Selection

After a subject is diagnosed as having a hepatic neoplasia, a method of treatment is selected. In hepatic cancer, for example, a number of standard treatment regimens are available. As described herein, identification of alterations in the expression of particular microRNAs is used in selecting a treatment method. MicroRNA expression profiles that correlate with poor clinical outcomes include downregulation of miR-26, that is a miR-26a-1, a miR-26a-2, or a miR26b microRNA, or any combination thereof, and are identified as aggressive neoplasias. An aggressive neoplasia is typically associated with a poorer prognosis (i.e., a higher probability of metastasis and/or death). MicroRNA expression profiles that correlate with good clinical outcomes are identified as less aggressive neoplasias.

Less aggressive neoplasias are likely to be susceptible to conservative treatment methods. More aggressive neoplasias are less susceptible to conservative treatment methods. Conservative treatment methods include, for example, chemotherapy using agents at dosages that are unlikely to cause adverse side effects, surgery that minimizes damage to tissues adjoining a tumor, or radiotherapy at a dosage that is likely to slow tumor growth without causing adverse side effects. Alternatively, a conservative treatment method might include cancer surveillance, which involves periodic patient monitoring using diagnostic assays. More aggressive neoplasias are treated with higher doses of chemotherapeutic or radiotherapeutic agents, with chemotherapeutic agents having increased toxicity, or with more radical surgery.

Kits

The invention provides kits for the diagnosis or monitoring of a neoplasia, such as hepatic neoplasia. In one embodiment, the kit detects an alteration in the expression of miR-26, that is a miR-26a-1, a miR-26a-2, or a miR26b microRNA, or any combination thereof, relative to a reference level of expression. In another embodiment, the kit detects an alteration in the sequence of a miR-26a derived from a subject relative to a reference sequence. In related embodiments, the kit includes reagents for monitoring the expression of a miR-26a nucleic acid molecule, such as primers or probes that hybridize to a miR-26a nucleic acid molecule.

Optionally, the kit includes directions for monitoring the nucleic acid molecule levels of a miR-26, that is a miR-26a-1, a miR-26a-2, or a miR26b microRNA, or any combination thereof, in a biological sample derived from a subject. In other embodiments, the kit comprises a sterile container which contains the primer, probe, antibody, or other detection regents; such containers can be boxes, ampules, bottles, vials, tubes, bags, pouches, blister-packs, or other suitable container form known in the art. Such containers can be made of plastic, glass, laminated paper, metal foil, or other materials suitable for holding nucleic acids. The instructions will generally include information about the use of the primers or probes described herein and their use in diagnosing a neoplasia. Preferably, the kit further comprises any one or more of the reagents described in the diagnostic assays described herein. In other embodiments, the instructions include at least one of the following: description of the primer or probe; methods for using the enclosed materials for the diagnosis of a neoplasia; precautions; warnings; indications; clinical or research studies; and/or references. The instructions may be printed directly on the container (when present), or as a label applied to the container, or as a separate sheet, pamphlet, card, or folder supplied in or with the container.

Patient Monitoring

The disease state or treatment of a patient having a hepatic neoplasia can be monitored using the methods and compositions of the invention. In one embodiment, the disease state of a patient can be monitored using the methods and compositions of the invention. Such monitoring may be useful, for example, in assessing the efficacy of a particular drug in a patient. Therapeutics that alter the expression of miR-26a is taken as particularly useful in the invention.

Screening Assays

One embodiment of the invention encompasses a method of identifying an agent that inhibits or increases the expression or activity of a miR-26 microRNA, that is a miR-26a-1, a miR-26a-2, or a miR26b microRNA, or any combination thereof. Accordingly, compounds that increase the expression or activity of a miR-26 nucleic acid molecule, variant, or portion thereof are useful in the methods of the invention for the treatment or prevention of a neoplasm (e.g., liver cancer). The method of the invention may measure a decrease in transcription of one or more microRNAs of the invention. Any number of methods are available for carrying out screening assays to identify such compounds. In one approach, the method comprises contacting a cell that expresses a microRNA with an agent and comparing the level of microRNA expression in the cell contacted by the agent with the level of expression in a control cell, wherein an agent that increases the expression of a miR-26, thereby inhibits a hepatic neoplasia. In another approach, candidate compounds are identified that specifically bind to and alter the activity of a microRNA of the invention. Methods of assaying such biological activities are known in the art and are described herein. The efficacy of such a candidate compound is dependent upon its ability to interact with a miR-26 microRNA. Such an interaction can be readily assayed using any number of standard binding techniques and functional assays (e.g., those described in Ausubel et al., supra).

Potential agonists of a miR-26 microRNA, that is a miR-26a-1, a miR-26a-2, or a miR26b microRNA, or any combination thereof, include any agent that enhances the expression or biological activity of the miR-26 microRNA, particularly in a liver cell. Such agents include organic molecules, peptides, peptide mimetics, polypeptides, nucleic acid molecules such as double-stranded RNAs, and antibodies. Also included are small molecules that bind to the microRNA thereby altering binding to cellular molecules with which the microRNA normally interacts, such that the normal biological activity or stability of the miR-26 microRNA is increased. Small molecules of the invention preferably have a molecular weight below 2,000 daltons, more preferably between 300 and 1,000 daltons, and still more preferably between 400 and 700 daltons. It is preferred that these small molecules are organic molecules.

Compounds that are identified as binding to a miR-26 microRNA, that is a miR-26a-1, a miR-26a-2, or a miR26b microRNA, or any combination thereof, with an affinity constant less than or equal to 10 mM are considered particularly useful in the invention. Alternatively, any in vivo protein interaction detection system, for example, any two-hybrid assay may be utilized to identify compounds that interact with such microRNAs. Interacting compounds isolated by this method (or any other appropriate method) may, if desired, be further purified (e.g., by high performance liquid chromatography). Compounds isolated by any approach described herein may be used as therapeutics to treat a neoplasia in a human patient.

In addition, compounds that normalize the expression of miR-26, that is a miR-26a-1, a miR-26a-2, or a miR26b microRNA, or any combination thereof, whose expression is altered in a subject having a hepatic neoplasia are also useful in the methods of the invention. Any number of methods are available for carrying out screening assays to identify new candidate compounds that increase the expression of a miR-26 microRNA.

The invention also includes novel compounds identified by the above-described screening assays. Optionally, such compounds are characterized in one or more appropriate animal models to determine the efficacy of the compound for the treatment of a hepatic neoplasia. Desirably, characterization in an animal model can also be used to determine the toxicity, side effects, or mechanism of action of treatment with such a compound. Furthermore, novel compounds identified in any of the above-described screening assays may be used for the treatment of a hepatic neoplasia in a subject. Such compounds are useful alone or in combination with other conventional therapies known in the art.

Test Compounds and Extracts

In general, compounds capable of inhibiting the growth or proliferation of a neoplasia by altering the expression or biological activity of miR-26, that is a miR-26a-1, a miR-26a-2, or a miR26b microRNA, or any combination thereof, are identified from large libraries of either natural product or synthetic (or semi-synthetic) extracts or chemical libraries according to methods known in the art. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.).

In one embodiment, test compounds of the invention are present in any combinatorial library known in the art, including: biological libraries; peptide libraries (libraries of molecules having the functionalities of peptides, but with a novel, non-peptide backbone which are resistant to enzymatic degradation but which nevertheless remain bioactive; see, e.g., Zuckermann, R. N. et al., *J. Med. Chem.* 37:2678-85, 1994); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, *Anticancer Drug Des.* 12:145, 1997).

Examples of methods for the synthesis of molecular libraries can be found in the art, for example in: DeWitt et al., *Proc. Natl. Acad. Sci. U.S.A.* 90:6909, 1993; Erb et al., *Proc. Natl. Acad. Sci. USA* 91:11422, 1994; Zuckermann et al., *J. Med. Chem.* 37:2678, 1994; Cho et al., *Science* 261:1303, 1993; Carrell et al., *Angew. Chem. Int. Ed. Engl.* 33:2059, 1994; Carell et al., *Angew. Chem. Int. Ed. Engl.* 33:2061, 1994; and Gallop et al., *J. Med. Chem.* 37:1233, 1994.

Libraries of compounds may be presented in solution (e.g., Houghten, *Biotechniques* 13:412-421, 1992), or on beads (Lam, *Nature* 354:82-84, 1991), chips (Fodor, *Nature* 364:555-556, 1993), bacteria (Ladner, U.S. Pat. No. 5,223,409), spores (Ladner U.S. Pat. No. 5,223,409), plasmids (Cull et al., *Proc Natl Acad Sci USA* 89:1865-1869, 1992) or on phage (Scott and Smith, *Science* 249:386-390, 1990; Devlin, *Science* 249:404-406, 1990; Cwirla et al. *Proc. Natl. Acad. Sci.* 87:6378-6382, 1990; Felici, *J. Mol. Biol.* 222:301-310, 1991; Ladner supra.).

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their anti-neoplastic activity should be employed whenever possible.

In an embodiment of the invention, a high throughput approach can be used to screen different chemicals for their potency to increase the activity of miR-26a microRNA. For example, a cell based sensor approach can be used to identify agents that increase expression of miR-26a. In one embodiment, the invention provides a method for identifying an agent that inhibits a neoplasia, the method comprising contacting a cell containing a sensor construct with an agent (polynucleotide, polypeptide, or small molecule), where the sensor construct contains a reporter gene linked to a site complementary to a microRNA of the invention; and measuring an alteration in the expression of the reporter gene relative to the expression of the reporter gene present in a control vector (e.g., a control vector not having a site complementary to the microRNA), wherein an alteration in the level of reporter expression identifies the agent as treating a neoplasia.

Those skilled in the field of drug discovery and development will understand that the precise source of a compound or test extract is not critical to the screening procedure(s) of the invention. Accordingly, virtually any number of chemical extracts or compounds can be screened using the methods described herein. Examples of such extracts or compounds include, but are not limited to, plant-, fungal-, prokaryotic- or animal-based extracts, fermentation broths, and synthetic compounds, as well as modification of existing compounds.

When a crude extract is found to alter the biological activity of a microRNA (e.g., miR-26a) variant, or fragment thereof, further fractionation of the positive lead extract can be performed to isolate chemical constituents responsible for the observed effect. Thus, the goal of the extraction, fractionation, and purification process is the careful characterization and identification of a chemical entity within the crude extract having anti-neoplastic activity. Methods of fractionation and purification of such heterogeneous extracts are known in the art. If desired, compounds shown to be useful agents for the treatment of a neoplasm are chemically modified according to methods known in the art.

Accordingly, the present invention provides methods of treating disease and/or disorders or symptoms thereof which comprise administering a therapeutically effective amount of a pharmaceutical composition comprising an agent of the formulae herein to a subject (e.g., a mammal such as a human). Thus, one embodiment is a method of treating a subject suffering from or susceptible to a neoplastic disease or disorder or symptom thereof. The method includes the step of administering to the mammal a therapeutic amount of an amount of a compound herein sufficient to treat the disease or disorder or symptom thereof, under conditions such that the disease or disorder is treated.

The methods herein include administering to the subject (including a subject identified as in need of such treatment) an effective amount of an agent described herein, or a composition described herein to produce such effect. Identifying a subject in need of such treatment can be in the judgment of a subject or a health care professional and can be subjective (e.g., opinion) or objective (e.g., measurable by a test or diagnostic method).

The therapeutic methods of the invention (which include prophylactic treatment) in general comprise administration of a therapeutically effective amount of the agents herein, such as an agent of the formulae herein to a subject (e.g., animal, human) in need thereof, including a mammal, particularly a human. Such treatment will be suitably administered to subjects, particularly humans, suffering from, having, susceptible to, or at risk for a disease, disorder, or symptom thereof, particularly a hepatic neoplasia. Determination of those subjects "at risk" can be made by any objective or subjective determination by a diagnostic test or opinion of a subject or health care provider (e.g., genetic test, enzyme or protein marker, miR-26a, family history, imaging test, and the like).

In one embodiment, the invention provides a method of monitoring treatment progress. The method includes the step of determining a level of miR-26, that is a miR-26a-1, a miR-26a-2, or a miR26b microRNA, or any combination thereof, or diagnostic measurement (e.g., screen, assay) in a subject suffering from or susceptible to a disorder or symptoms thereof associated with hepatic neoplasia, in which the subject has been administered a therapeutic amount of an agent herein sufficient to treat the disease or symptoms thereof. The level of miR-26 determined in the method can be compared to known levels of miR-26 in either healthy normal controls or in other afflicted patients to establish the subject's disease status. In preferred embodiments, a second level of miR-26 in the subject is determined at a time point later than the determination of the first level, and the two levels are compared to monitor the course of disease or the efficacy of the therapy. In certain preferred embodiments, a pre-treatment level of miR-26 in the subject is determined prior to beginning treatment according to this invention; this pre-treatment level of miR-26 can then be compared to the level of miR-26 in the subject after the treatment commences, to determine the efficacy of the treatment.

Combination Therapies

Optionally, any therapeutic delineated herein may be administered in combination with a standard anti-hepatic neoplasia therapy; such methods are known to the skilled artisan and described in Remington's Pharmaceutical Sciences by E. W. Martin. Exemplary anti-neoplastic therapies include, for example, chemotherapy, cryotherapy, hormone therapy, radiotherapy, and surgery. Combinations of the invention provide for the administration of a therapeutic polynucleotide or inhibitory nucleic acid described herein (e.g., a nucleotide encoding miR-26a) alone or in any combination. Specifically, any method known in the art that increases the expression of mir-26, that is a miR-26a-1, a miR-26a-2, or a miR26b microRNA, or any combination thereof, is expected to be therapeutic. If desired the combination includes one, two, three, four, five or even six therapeutics that increase the levels of miR-26, either directly or indirectly.

A therapeutic regimen of the invention may, if desired, include one or more chemotherapeutics typically used in the treatment of a neoplasm, such as abiraterone acetate, altretamine, anhydrovinblastine, auristatin, bexarotene, bicalutamide, BMS184476, 2,3,4,5,6-pentafluoro-N-(3-fluoro-4-methoxyphenyl)benzene sulfonamide, bleomycin, N,N-dimethyl-L-valyl-L-valyl-N-methyl-L-valyl-L-proly-I-Lproline-t-butylamide (SEQ ID NO: 44), cachectin, cemadotin, chlorambucil, cyclophosphamide, 3',4'-didehydro-4'-deoxy-8'-norvin-caleukoblastine, docetaxol, doxetaxel, cyclophosphamide, carboplatin, carmustine (BCNU), cisplatin, cryptophycin, cyclophosphamide, cytarabine, dacarbazine (DTIC), dactinomycin, daunorubicin, dolastatin, doxorubicin (adriamycin), etoposide, 5-fluorouracil, finasteride, flutamide, hydroxyurea and hydroxyureataxanes, ifosfamide, liarozole, lonidamine, lomustine (CCNU), mechlorethamine (nitrogen mustard), melphalan, mivobulin isethionate, rhizoxin, sertenef, streptozocin, mitomycin, methotrexate, 5-fluorouracil, nilutamide, onapristone, paclitaxel, prednimustine, procarbazine, RPR109881, stramustine phosphate, tamoxifen, tasonermin, taxol, tretinoin, vinblastine, vincristine, vindesine sulfate, and vinflunine. Other examples of chemotherapeutic agents can be found in Cancer Principles and Practice of Oncology by V. T. Devita and S. Hellman (editors), 6th edition (Feb. 15, 2001), Lippincott Williams & Wilkins Publishers.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1

Materials and Methods

Cell Culture

HEK293, HEK293T, and HeLa cells were cultured in high glucose (4.5 g/L) DMEM supplemented with 10% fetal bovine serum (FBS), penicillin, and streptomycin. HepG2 cells were cultured in EMEM supplemented with 10% FBS, penicillin, and streptomycin.

RNA Isolation and Northern Blotting

Total RNA was isolated from cultured cells or tissue using Trizol (Invitrogen) according to the manufacturer's protocol. Northern blotting was performed as previously described (Hwang et al., 2007) using Ultrahyb-oligo buffer (Ambion) and oligonucleotide probes perfectly complementary to the mature miRNA sequences. All membranes were stripped and re-probed for tRNALys as a loading control.

Plasmid Construction

MSCV.PIG retroviral vectors expressing miR-18a, miR-26a, and miR-34a were previously described (Chang et al., 2008). For luciferase reporter constructs, the predicted miR-26a binding site and approximately 225 bp of flanking 3'UTR sequence was amplified from human genomic DNA and cloned into the XbaI site of pGL3-control (Promega). Mutagenesis was performed with the QuickChange XL site-directed mutagenesis kit (Stratagene). Primer sequences are provided in Table 1.

The self-complementary vector plasmid scAAV.eGFP includes a deletion in the terminal resolution site in a single inverted terminal repeat. As a result, this construct produces only dimeric inverted repeat genomes during replication and encapsidation (McCarty et al., 2003). The vector consists of the human EF1α promoter [EF1α promoter core domain (592 bp), Exon 1 (33 bp), Intron 1, (593 bp) and Exon 2 leader sequence (9 bp)], an enhanced green fluorescent protein (GFP) open reading frame, and a SV40 polyadenylation signal. To construct scAAV.miR26a, eGFP sequences were removed by NheI/NotI digestion and replaced with miR-26a-2 and approximately 200 bp of flanking genomic sequence amplified from human genomic DNA. To produce scAAV.miR26a.eGFP, miR-26a-2 was amplified and cloned into the FseI site within the EF1α intron in scAAV.eGFP. pcDNA-miR-122a was constructed by amplifying miR-122a from human genomic DNA and cloning into the XhoI site of pcDNA3.1(+) (Invitrogen). Primer sequences are provided in Table 2.

Retroviral Infection of HepG2 Cells $8 \times 10^6$ HEK293T cells were co-transfected with MSCV.PIG constructs, gag-pol, and VSV-G helper plasmids using the FuGene6 reagent (Roche). Following transfection, the retroviral supernatant was collected, filtered, and supplemented with 12 µg/mL polybrene. $1 \times 10^6$ HepG2 cells were infected twice for 8 hours each and, 48 hours after the second infection, plated into medium containing 1.25 n/mL puromycin and selected for 48 hours. Cells were then plated for cell-cycle profiling and RNA/protein collection.

Cell-Cycle Profiling $5 \times 10^5$ retrovirally-infected HepG2 cells were plated after selection. 24 hours later, cells were harvested for analysis by propidium iodide (PI) staining and flow cytometry as described previously (Hwang et al., 2007). For M-phase trapping experiments, 100 ng/mL nocodazole was added for 24 hours prior to harvesting floating and adherent cells for PI staining.

Western Blotting

Antibodies for immunoblotting were as follows: anti-c-Myc mouse monoclonal (clone 9E10; Zymed), anti-cyclin E1 rabbit polyclonal (Abcam), anti-cyclin E2 rabbit polyclonal (Cell Signaling), anti-cyclin D2 rabbit polyclonal (Cell Signaling), anti-CDK6 mouse monoclonal (clone DCS83; Cell Signaling), and anti-α-tubulin mouse monoclonal (clone DM1A; Calbiochem).

Luciferase Reporter Assays $2.5 \times 10^5$ HepG2 cells were plated in triplicate wells of a 24-well plate and transfected 16 hours later with 100 ng of the indicated pGL3 3' UTR reporter construct and 5 ng of phRL-SV40 (Promega) using Lipofectamine 2000 (Invitrogen) according to the manufacturer's instructions. Where indicated, miR-18a or miR-26a mimics (Dharmacon) were co-transfected at 25 nM final concentration. 24 hours after transfection, cells were lysed and assayed for firefly and renilla luciferase activity using the Dual-Luciferase Reporter Assay System (Promega). Firefly luciferase activity was normalized to renilla luciferase activity for each transfected well. Data depicted is representative of three independent experiments performed on different days.

Transient Transfection of HeLa Cells $1.5 \times 10^6$ HeLa cells were plated and transfected 16 hours later using the TransIT-HeLaMONSTER reagent (Minis) with 4 µg each of the indicated scAAV construct and pcDNA-miR-122a. 24 hours after transfection, cells were imaged by fluorescence microscopy and harvested for RNA isolation.

AAV Vector Production

Recombinant AAV vectors were produced by a standard triple transfection calcium phosphate precipitation method using HEK293 cells. The production plasmids were: (i) scAAV.eGFP or scAAV.miR26a.eGFP, (ii) rep2-cap8 modified AAV helper plasmid encoding the cap serotype 8-like isolate rh.74, and (iii) an adenovirus type 5 helper plasmid (pAdhelper) expressing adenovirus E2A, E4 ORF6, and VA I/II RNA genes. Purification was accomplished from clarified 293 cell lysates by sequential iodixanol gradient purification and ion exchange column chromatography using a linear NaCl salt gradient for particle elution. Vector genome (vg) titers were determined by quantitative polymerase chain reaction (qPCR) as described (Clark et al., 1999). Primer and probe sequences are provided in Table 3. The miR-26a with flanking sequence that delivered was (partial pri-miR-26a-2; mature miRNA sequence underlined)

```
                                        (SEQ ID NO: 10)
5'-CCCTGGTGCAATTCATTACCTAATCATGACCTGGACAGACTGTCCTG

TCGGAGCCAAGGACAGAAAGCTCCCATAGAGGCTGTGGCTGGATTCAAGT

AATCCAGGATAGGCTGTTTCCATCTGTGAGGCCTATTCTTGATTACTTGT

TTCTGGAGGCAGCTGATGGTCCGCCGCCGGAAACAGAGATGGCTCCTGGG

ACATGGTGTGTGCGCTTCTTCCTGAGCCAGGTTGAGGTTGGGACCACTGA

T-3'
```

Figure 4A:
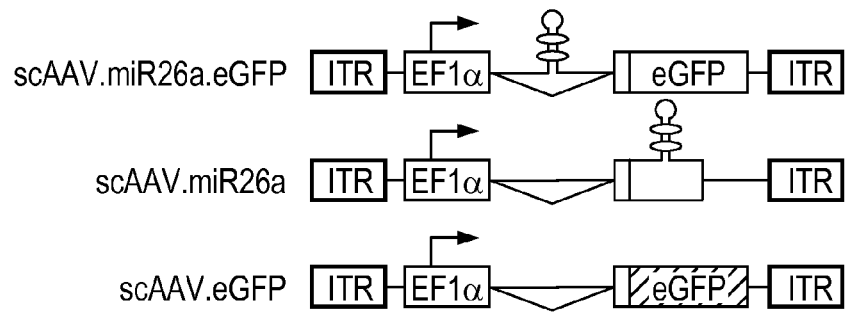
FIG. 4. Development of an AAV vector system to simultaneously express a miRNA and eGFP (A) Schematic representation of scAAV vectors used in this study depicting locations of inverted terminal repeats (ITRs), elongation factor 1 α promoter (EF1α), miRNA (shown in hairpin form), and enhanced green fluorescent protein (eGFP) open reading frame. (B) Northern blot of transiently-transfected HeLa cells demonstrating equivalent levels of miR-26a when expressed from an intronic (scAAV.miR26a.eGFP) or exonic (scAAV.miR26a) context. Co-transfection with a miR-122a expression plasmid (pcDNA-miR-122a) provided a control for transfection efficiency while tRNALys levels documented equal loading. (C) Fluorescent microscopy showing eGFP expression in HeLa cells transiently-transfected with the indicated AAV vectors. (D) Northern blots showing expression of miRNAs in livers 21 days following administration of the indicated AAV vectors. (E) Fluorescent microscopy showing efficient transduction of hepatocytes, as indicated by eGFP expression, 21 days following AAV administration. (F) Representative H&E-stained sections of liver 21 days following administration of the indicated AAV vectors to show that infection with scAAV8 vectors does not produce overt liver toxicity.
Figure 4B:
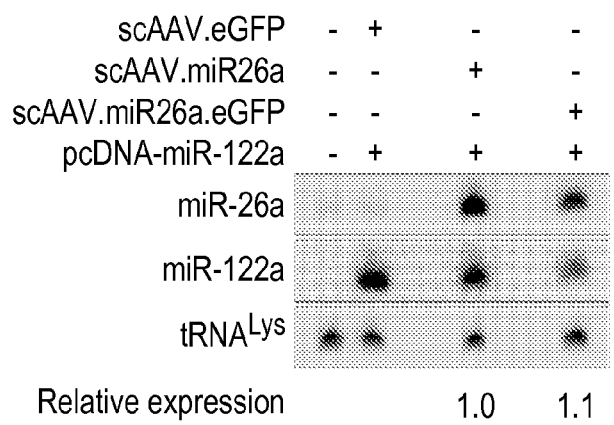
Figure 4C:
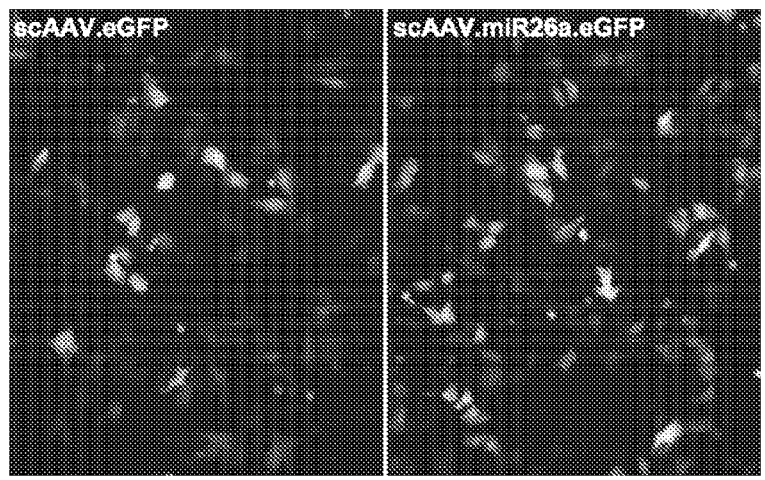

Sequence of entire AAV vector genome (corresponds to FIG. 4A)

```
                                        (SEQ ID NO: 11)
5'CAGCAGCTGCGCGCTCGCTCGCTCACTGAGGCCGCCCGGGCAAAGCCC

GGGCGTCGGGCGACCTTTGGTCGCCCGGCCTCAGTGAGCGAGCGAGCGCG

CAGAGAGGGAGTGGGGTTATCGGCGCGCCACTAGTGAGGCTCCGGTGCCC

GTCAGTGGGCAGAGCGCACATCGCCCACAGTCCCCGAGAAGTTGGGGGGA

GGGGTCGGCAATTGAACCGGTGCCTAGAGAAGGTGGCGCGGGGTAAACTG

GGAAAGTGATGTCGTGTACTGGCTCCGCCTTTTTCCCGAGGGTGGGGGAG

AACCGTATATAAGTGCAGTAGTCGCCGTGAACGTTCTTTTTCGCAACGGG

TTTGCCGCCAGAACACAGGTAAGTGCCGTGTGTGGTTCCCGCGGGCGGCG

ACGGGGCCCGTGCGTCCCAGCGCACATGTTCGGCGAGGCGGGCCTGCGA

GCGCGGCCACCGAGAATCGGACGGGGGTAGTCTCAAGCTGGCCGGCCCCC

TGGTGCAATTCATTACCTAATCATGACCTGGACAGACTGTCCTGTCGGAG

CCAAGGACAGAAAGCTCCCATAGAGGCTGTGGCTGGATTCAAGTAATCCA

GGATAGGCTGTTTCCATCTGTGAGGCCTATTCTTGATTACTTGTTTCTGG

AGGCAGCTGATGGTCCGCCGCCGGAAACAGAGATGGCTCCTGGGACATGG

TGTGTGCGCTTCTTCCTGAGCCAGGTTGAGGTTGGGACCACTGATGGCCG

GCCTGCTCTGGTGCCTGGCCTCGCGCCGCCGTGTATCGCCCCGCCCTGGG

CGGCAAGGCTGGCCCGGTCGGCACCAGTTGCGTGAGCGGAAAGATGGCCG

CTTCCCGGCCCTGCTGCAGGGAGCTCAAAATGGAGGACGCGGCGCTCGGG

AGAGCGGGCGGGTGAGTCACCCACACAAAGGAAAAGGGCCTTTCCGTCCT

CAGCCGTCGCTTCATGTGACTCCACGGAGTACCGGGCGCCGTCCAGGCAC

CTCGATTAGTTCTCGAGCTTTTGGAGTACGTCGTCTTTAGGTTGGGGGGA

GGGGTTTTATGCGATGGAGTTTCCCCACACTGAGTGGGTGGAGACTGAAG

TTAGGCCAGCTTGGCACTTGATGTAATTCTCCTTGGAATTTGCCCTTTTT

GAGTTTGGATCTTGGTTCATTCTCAAGCCTCAGACAGTGGTTCAAAGTTT

TTTTCTTCCATTTCAGGTGTCGTGAAAAGCTAGCGCTACCGGACTCAGAT

CTCGAGCTCAAGCTTCGAATTCTGCAGTCGACGGTACCGCGGGCCCGGGA

TCCACCGGTCGCCACCATGGTGAGCAAGGGCGAGGAGCTGTTCACCGGGG

TGGTGCCCATCCTGGTCGAGCTGGACGGCGACGTAAACGGCCACAAGTTC

AGCGTGTCCGGCGAGGGCGAGGGCGATGCCACCTACGGCAAGCTGACCCT

GAAGTTCATCTGCACCACCGGCAAGCTGCCCGTGCCCTGGCCCACCCTCG

TGACCACCCTGACCTACGGCGTGCAGTGCTTCAGCCGCTACCCCGACCAC

ATGAAGCAGCACGACTTCTTCAAGTCCGCCATGCCCGAAGGCTACGTCCA

GGAGCGCACCATCTTCTTCAAGGACGACGGCAACTACAAGACCCGCGCCG

AGGTGAAGTTCGAGGGCGACACCCTGGTGAACCGCATCGAGCTGAAGGGC

ATCGACTTCAAGGAGGACGGCAACATCCTGGGGCACAAGCTGGAGTACAA

CTACAACAGCCACAACGTCTATATCATGGCCGACAAGCAGAAGAACGGCA

TCAAGGTGAACTTCAAGATCCGCCACAACATCGAGGACGGCAGCGTGCAG

CTCGCCGACCACTACCAGCAGAACACCCCCATCGGCGACGGCCCCGTGCT

GCTGCCCGACAACCACTACCTGAGCACCCAGTCCGCCCTGAGCAAAGACC

CCAACGAGAAGCGCGATCACATGGTCCTGCTGGAGTTCGTGACCGCCGCC

GGGATCACTCTCGGCATGGACGAGCTGTACAAGTAAAGCGGCCGCGGGGA

TCCAGACATGATAAGATACATTGATGAGTTTGGACAAACCACAACTAGAA

TGCAGTGAAAAAAATGCTTTATTTGTGAAATTTGTGATGCTATTGCTTTA

TTTGTAACCATTATAAGCTGCAATAAACAAGTTAACAACAACAATTGCAT

TCATTTTATGTTTCAGGTTCAGGGGGAGGTGTGGGAGGTTTTTTTCTAGA

GCATGGCTACGTAGATAAGTAGCATGGCGGGTTAATCATTAACTACAAGG

AACCCCTAGTGATGGAGTTGGCCACTCCCTCTCTGCGCGCTCGCTCGCTC

ACTGAGGCCGGGCGACCAAAGGTCGCCCGACGCCCGGGCTTTGCCCGGGC

GGCCTCAGTGAGCGAGCGAGCGCGCCAGC-3'
```

Vector Delivery

Tet-o-MYC; LAP-tTA mice were maintained on dox-containing food (100 mg/kg) until 4 weeks of age. At 11 weeks of age, AAV was administered at a dose of 1012 vg per animal by tail vein injection (200 uL total volume) using a 30 gauge ultra-fine insulin syringe. The Research Institute at Nationwide Children's Hospital Animal Care and Use Committee approved all housing and surgical procedures.

Immunohistochemistry

Tissues were collected in 10% buffered formalin, embedded in paraffin, and stained in hematoxylin and eosin following standard procedures. For Ki67 detection, slides were microwaved for 15 min in 10 mM sodium citrate (pH 6.0), cooled for 20 min at 25° C., and washed three times (5 minutes each) with PBST (PBS, 0.1% Tween® 20). The tissue was permeabilized by incubating the slides in 1% Triton X-100 in PBS at 4° C. for 30 min and then washed again three times in PBST. After blocking for 1 hour at 25° C. in blocking buffer (PBS containing 10% goat serum and 0.2% Triton® X-100), slides were incubated overnight in a humidity chamber with a mouse anti-human Ki67 monoclonal antibody (BD Biosciences) diluted 1:100 in blocking buffer. Following another three PBST washes, slides were incubated with Alexa® 594-conjugated goat anti-mouse secondary antibody at a 1:200 dilution (Molecular Probes). Slides were washed and nuclei counter-stained with DAPI. The intensity of the Ki67 signal was quantified using the Olympus® Slidebook 4.2 software. TUNEL staining was performed with the TMR Red In situ cell death detection kit (Roche) according to manufacturer's instructions. Quantification of TUNEL positive area was performed using ImageJ software. For GFP visualization, tissues were fixed in 4% paraformaldehyde followed by an overnight incubation in 30% sucrose incubation and then embedded in OCT compound.

AAV Transduction Efficiency

Transduction efficiency was determined by counting the number of GFP positive and negative hepatocytes using four random 20× GFP and DAPI overlap images. To further quantify transduction, eGFP transgene qPCR was performed on total DNA isolated from liver tissue. Total tissue DNA was isolated using the Gentra Puregene kit (Qiagen) according to the manufacturer's instructions. 60 ng of DNA (10,000 cell equivalents) was used as PCR template in triplicate reactions and vg number was extrapolated from a linearized plasmid standard. Vector genome/cell calculations assume 6 pg of total DNA per cell. Primer and probe sequences are provided in Table 3.

Tumor Tissue Procurement

After obtaining appropriate Institutional Review Board approval, fresh tissues from hepatitis C-positive patients were collected at the time of surgery from primary liver neoplasms and adjacent non-neoplastic liver tissues, snap frozen in liquid nitrogen, and stored at −80 C. The tissue diagnoses were confirmed in all cases by routine light microscopy.

Plasmid Construction

MSCV.PIG retroviral vectors expressing miR-18a, miR-26a, and miR-34a were previously described (Chang et al., 2008). For luciferase reporter constructs, the predicted miR-26a binding site and approximately 225 by of flanking 3′ UTR sequence was amplified from human genomic DNA and cloned into the XbaI site of pGL3-control (Promega). Mutagenesis was performed with the QuickChange XL site-directed mutagenesis kit (Stratagene). Primer sequences are provided in Table 2.

The self-complementary vector plasmid scAAV.eGFP includes a deletion in the terminal resolution site in a single inverted terminal repeat. As a result, this construct produces only dimeric inverted repeat genomes during replication and encapsidation (McCarty et al., 2003). The vector consists of the human EF1a promoter [EF1a promoter core domain (592 bp), Exon 1 (33 bp), Intron 1, (593 bp) and Exon 2 leader sequence (9 bp)], an enhanced green fluorescent protein (GFP) open reading frame, and a SV40 polyadenylation signal. To construct scAAV.miR26a, eGFP sequences were removed by NheI/NotI digestion and replaced with miR¬26a-2 and approximately 200 by of flanking genomic sequence amplified from human genomic DNA. To produce scAAV.miR26a.eGFP, miR-26a-2 was amplified and cloned into the FseI site within the EF1a intron in scAAV.eGFP. pcDNA-miR-122a was constructed by amplifying miR¬122a from human genomic DNA and cloning into the XhoI site of pcDNA3.1(+) (Invitrogen). Primer sequences are provided in Table 3.

Retroviral Infection of HepG2 Cells $8 \times 10^6$ HEK293T cells were co-transfected with MSCV.PIG constructs, gag-pol, and VSV-G helper plasmids using the FuGene6 reagent (Roche). Following transfection, the retroviral supernatant was collected, filtered, and supplemented with 12 pg/mL polybrene. $1 \times 10^6$ HepG2 cells were infected twice for 8 hours each and, 48 hours after the second infection, plated into medium containing 1.25 pg/mL puromycin and selected for 48 hours. Cells were then plated for cell-cycle profiling and RNA/protein collection.

Transient Transfection of HeLa Cells $1.5 \times 10^6$ HeLa cells were plated and transfected 16 hours later using the TransIT-HeLaMONSTER reagent (Minis) with 4 pg each of the indicated scAAV construct and pcDNA-miR-122a. 24 hours after transfection, cells were imaged by fluorescence microscopy and harvested for RNA isolation.

AAV Vector Production

Recombinant AAV vectors were produced by a standard triple transfection calcium phosphate precipitation method using HEK293 cells. The production plasmids were: (i) scAAV.eGFP or scAAV.miR26a.eGFP, (ii) rep2-cap8 modified AAV helper plasmid encoding the cap serotype 8-like isolate rh.74, and (iii) an adenovirus type 5 helper plasmid (pAdhelper) expressing adenovirus E2A, E4 ORF6, and VA I/II RNA genes. Purification was accomplished from clarified 293 cell lysates by sequential iodixanol gradient purification and ion exchange column chromatography using a linear NaCl salt gradient for particle elution. Vector genome (vg) titers were determined by quantitative polymerase chain reaction (qPCR) as described (Clark et al., 1999). Primer and probe sequences are provided in Table 2.

AAV Transduction Efficiency

Transduction efficiency was determined by counting the number of GFP positive and negative hepatocytes using four random 20× GFP and DAPI overlap images. To further quantify transduction, eGFP transgene qPCR was performed on total DNA isolated from liver tissue. Total tissue DNA was isolated using the Gentra Puregene kit (Qiagen) according to the manufacturer's instructions. 60 ng of DNA (10,000 cell equivalents) was used as PCR template in triplicate reactions and vg number was extrapolated from a linearized plasmid standard. Vector genome/cell calculations assume 6 pg of total DNA per cell. Primer and probe sequences are provided in Table 4.

Example 2

Downregulation of Putative Anti-Tumorigenic miRNAs in Myc-Induced Liver Tumors

We previously demonstrated that Myc activation in B cell lymphoma models results in downregulation of a large cohort of miRNAs including miR-15a/16, miR-26a, miR-34a, miR-150, and miR-195 (Chang et al., 2008). Enforced expression of these specific miRNAs dramatically inhibits B cell lymphomagenesis. In order to extend these findings to a solid tumor model and to investigate the potential use of these miRNAs as anti-cancer therapeutics, we studied their expression in a previously described model of liver cancer in which mice harboring a tetracycline (tet)-repressible MYC transgene (tet-o-MYC) are crossed with mice expressing the tet-transactivator protein (tTA) driven by the liver activator promoter (LAP) (Beer et al., 2004; Felsher and Bishop, 1999; Shachaf et al., 2004). Upon removal of doxycycline (dox), bi-transgenic animals express MYC specifically in the liver and subsequently develop liver tumors resembling HCC with complete penetrance.

Figure 1C:
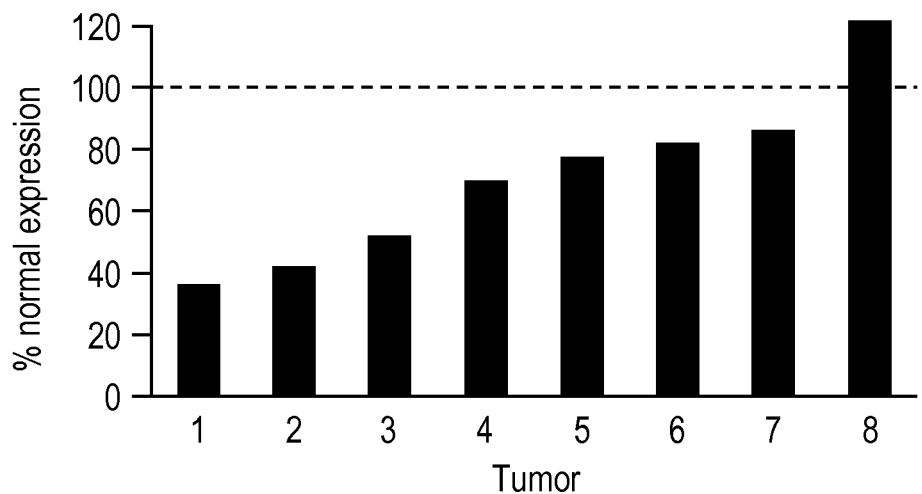

We sought miRNAs that are highly expressed and therefore tolerated in normal tissues but are expressed at reduced levels in tumors. Such miRNAs might exhibit anti-proliferative and pro-apoptotic effects that are restricted to cancer cells. Northern blotting revealed that miR-26a, and to a lesser extent miR-15a and miR-16, fulfilled these criteria, exhibiting high expression in normal liver from adult mice lacking the LAP-tTA transgene (harboring an inactive tet-o-MYC transgene) but low expression in liver tumors from tet-o-MYC; LAP-tTA bi-transgenic animals (FIG. 1). Notably, these miRNAs did not exhibit reduced expression in normal-appearing liver from bi-transgenic animals, consistent with the previous demonstration that Myc levels are only minimally increased in non-tumor tissue in these mice (Shachaf et al., 2004). Additional miRNAs with anti-tumorigenic activity in B lymphoma cells were expressed at approximately equivalent levels in normal liver and tumors (miR-195, FIG. 1) or were not detectable in these tissues (miR-150, data not shown). miR-34a was strongly upregulated in liver tumors (FIG. 1), perhaps reflecting its regulation by p53 which is retained and active in some tumors in these animals (Beer et al., 2004; He et al., 2007b). As expected, miR-17 was expressed at high levels in liver tumors, consistent with our previous demonstration that the miR-17-92 cluster is directly transactivated by Myc (O'Donnell et al., 2005). Based on these results, we selected miR-26a for functional studies to evaluate its anti-tumorigenic properties and potential therapeutic utility for liver cancer in vitro and in vivo.

Example 3 miR-26a Expression Induces a G1 Arrest in Human Hepatocellular Carcinoma Cells

As an initial test of the anti-proliferative properties of miR-26a in liver cancer cells, we utilized a murine stem cell virus (MSCV)-derived retroviral construct to enforce expression of this miRNA in the human HCC cell line HepG2. As controls for this experiment, we used viruses that express miR-18a, a component of the pro-tumorigenic miR-17-92 cluster, and miR-34a, which is known to have potent anti-proliferative and pro-apoptotic activity in other cell lines (Bommer et al., 2007; Chang et al., 2007; He et al., 2007a; Raver-Shapira et al., 2007; Tarasov et al., 2007). Northern blotting demonstrated that miR-26a expression levels in HepG2 cells closely minor expression levels in tumors from tet-o-MYC; LAP-tTA animals (FIG. 2A). Infection with MSCV-miR-26a results in enforced expression of this miRNA at a level comparable to that observed in normal liver tissue. Flow cytometric analysis of retrovirally-infected cell populations revealed fewer cells in S phase and increased numbers of cells in G1 following infection with MSCV-miR-26a and MSCV-miR-34a compared to cells infected with MSCV-empty or MSCV-miR-18a, suggesting that miR-26a and miR-34a induce a G1 arrest (FIG. 2B). To more accurately quantify the numbers of cells arrested in G1, we treated cells with the microtubule-destabilizing agent nocodazole which traps cycling cells in M phase. Cell populations with enforced miR-26a and miR-34a expression were characterized by significantly increased numbers of cells remaining in G1 (FIG. 2C), confirming that these miRNAs arrest the cell-cycle at this stage.

Example 4 miR-26a Directly Represses Expression of Cyclin D2 and Cyclin E2

To investigate the mechanisms through which miR-26a induces a G1 cell-cycle arrest, we examined predicted targets of this miRNA using the Targetscan algorithm (Grimson et al., 2007). This analysis predicts that miR-26a regulates cyclin E1 (CCNE1), cyclin E2 (CCNE2), cyclin D2 (CCND2), and cyclin-dependent kinase 6 (CDK6), all of which play a critical role in transition through the G1-S checkpoint (Vermeulen et al., 2003). Western blotting was used to determine if miR-26a represses any of these putative targets in retrovirally-infected cell populations.

Although infection with MSCV-miR-26a did not affect the abundance of cyclin E1 and CDK6 (data not shown), significantly reduced levels of cyclin D2 and cyclin E2 were observed in cells with enforced miR-26a expression (FIG. 3A,B).

Figure 3E:
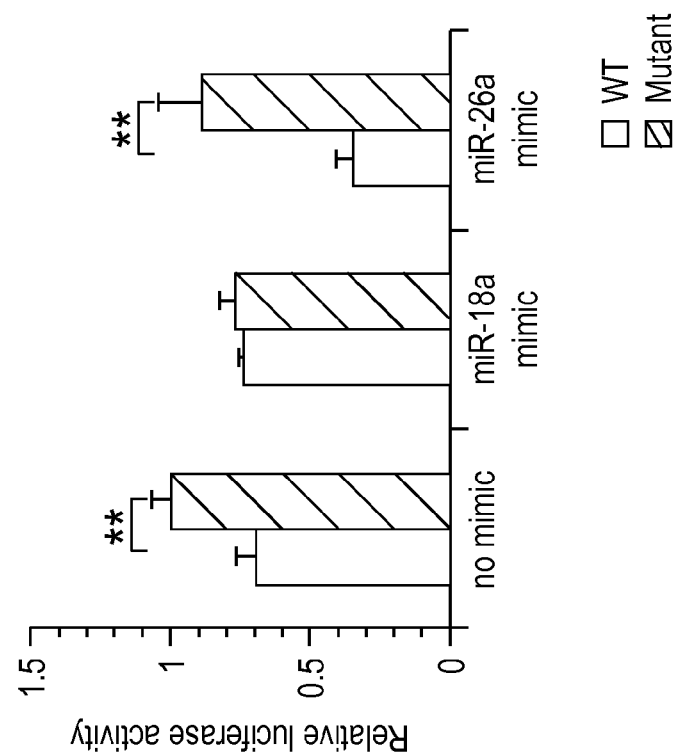
FIG. 3. miR-26a negatively regulates cyclins D2 and E2 (A-B) Western blots documenting abundance of cyclins D2 and E2 in retrovirally-infected HepG2 cells. Relative quantification of band intensities, normalized to tubulin levels, are shown below blots. (C-D) Sequence and evolutionary conservation of the miR-26a binding sites in the 3' UTRs of transcripts encoding cyclin D2 (CCND2) and cyclin E2 (CCNE2). Mutations introduced into luciferase reporter constructs are shown in red.
FIG. 3C discloses SEQ ID NOS 32-38, respectively, in order of appearance, and FIG. 3D discloses SEQ ID NOS 32 and 39-43, respectively, in order of appearance. (E-F) Relative firefly luciferase activity derived from CCND2 (E) and CCNE2 (F) 3' UTR reporter constructs following transfection into HepG2 cells alone or in combination with miR-18a or miR-26a synthetic miRNA mimics. All values were normalized to renilla luciferase activity produced from a co-transfected control plasmid. Error bars represent standard deviations from 3 independent transfections. *, $p<0.05$; **, $p<0.01$ (two-tailed t test). (G) Western blot showing that miR-26a does not target Myc in retrovirally-infected HepG2 cells.

Both CCND2 and CCNE2 have a single predicted miR-26a binding site in their 3' UTRs which are highly conserved in mammals and, in the case of CCND2, present in chicken (FIG. 3C,D). To verify that these transcripts are directly regulated by miR-26a, reporter plasmids were constructed in which portions of the 3' UTRs encompassing the predicted binding sites, with or without mutations that would disrupt miRNA interaction, were cloned downstream of a luciferase open reading frame. When introduced into HepG2 cells, constructs with intact miR-26a binding sites were expressed at significantly lower levels than the mutant constructs, consistent with direct functional interaction of endogenously-expressed miR-26a with these sites (FIG. 3E,F). Co-transfection of reporter plasmids with a synthetic miR-26a mimic further repressed luciferase activity produced from wild-type, but not mutant, reporter constructs. Demonstrating the specificity of these effects, co-transfection with a miR-18a mimic actually diminished downregulation of the wild-type reporters, possibly by competing for limiting miRNA pathway components and thereby relieving the transcript from repression. These data document that miR-26a directly represses expression of cyclin D2 and cyclin E2, providing one mechanism through which this miRNA arrests cell-cycle progression.

Example 5

MYC is Not a Target of miR-26a

Having demonstrated that miR-26a potently arrests proliferation of hepatocellular carcinoma cells in vitro, we next initiated a series of experiments to assess whether systemic delivery of this miRNA could be used as a therapeutic strategy for this tumor type in vivo. The tet-o-MYC; LAP-tTA liver cancer model represents an ideal setting for these studies. Because these mice were constructed with a human MYC transgene that includes its 3' UTR (Felsher and Bishop, 1999), we first confirmed that miR-26a does not regulate MYC itself. MYC is not a predicted target of miR-26a according to several commonly used algorithms including Targetscan, miRanda, and PicTar (Betel et al., 2008; Grimson et al., 2007; Krek et al., 2005). Manual inspection of the human MYC 3' UTR further documents the absence of even a minimal hexamer complementary to the miR-26a seed sequence.

Figure 3F:
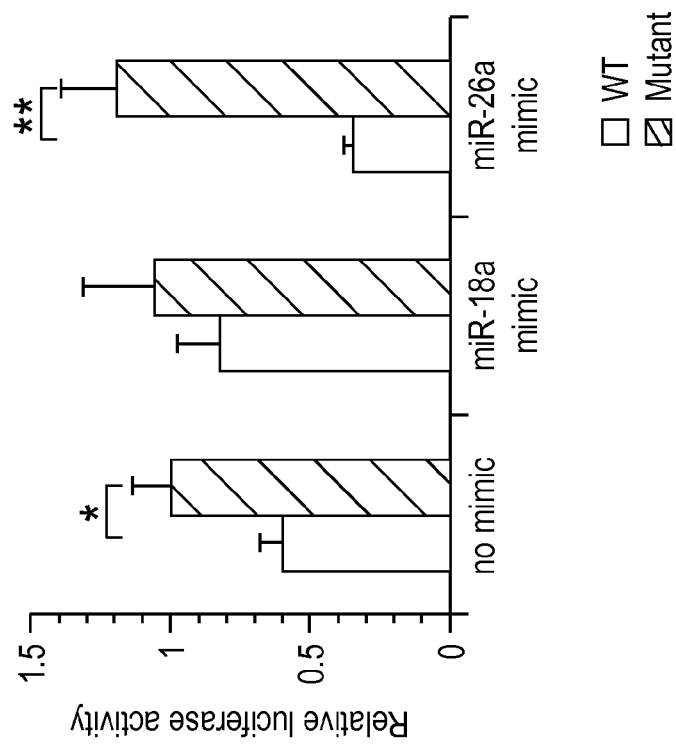
Figure 3G:
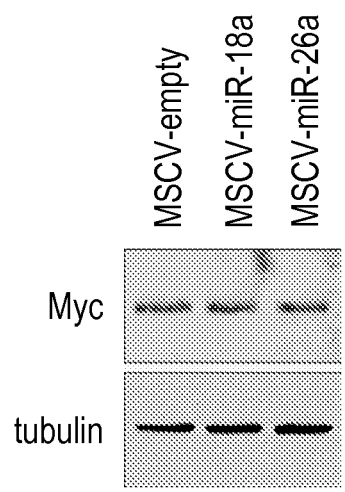

Western blotting confirms that retroviral expression of miR-26a in HepG2 cells does not affect Myc protein abundance (FIG. 3G). Thus, miR-26a does not target the initiating oncogene in tet-o-MYC; LAP-tTA mice, supporting the use of this model for assessing the general tumor suppressing properties of miR-26a in vivo.

Example 6

Development of an AAV Vector System to Simultaneously Express a miRNA and eGFP

Figure 4D:
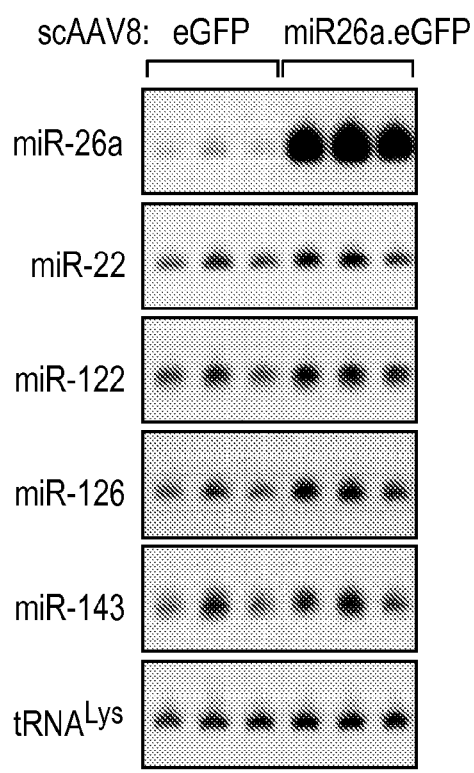
Figure 4E:
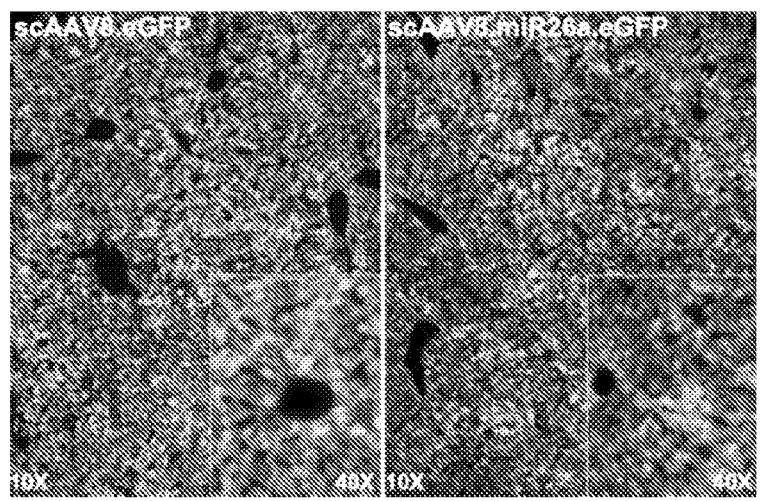

The development of self-complementary AAV (scAAV) vectors and the availability of AAV serotypes for improved transduction of specific target tissues has expanded the usefulness of this virus for therapeutic gene delivery (Gao et al., 2002; McCarty, 2008; McCarty et al., 2003; Nakai et al., 2005; Wang et al., 2003). In particular, these advances allow highly efficient transduction of hepatocytes following systemic administration of scAAV8 vectors. We therefore constructed a scAAV vector system to evaluate the therapeutic potential of miR-26a in tet-o-MYC; LAP-tTA mice. To allow facile assessment of target tissue transduction, the vector included enhanced green fluorescent protein (eGFP) driven by the ubiquitously expressed elongation factor 1 alpha (EF1α) promoter. Moreover, since miRNAs are frequently embedded within introns of both protein-coding and noncoding primary transcripts, we cloned miR-26a into the short intron which is part of the EF1α promoter unit (Wakabayashi-Ito and Nagata, 1994), thus allowing simultaneous production of eGFP and miR-26a from a single transcript (scAAV.miR26a.eGFP; FIG. 4A). We confirmed that this vector efficiently expresses both miR-26a and eGFP by transient transfection of HeLa cells. Northern blotting demonstrated that the scAAV.miR26a.eGFP vector produced an equivalent amount of mature miRNA as a control vector in which the miRNA was in an exonic context (scAAV.miR26a; FIG. 4A,B). Fluorescent microscopy of transfected cells similarly documented equivalent eGFP expression from scAAV.miR26a.eGFP and a control vector lacking intronic miR-26a sequences (scAAV.eGFP; FIG. 4A,C).

scAAV.eGFP and scAAV.miR26a.eGFP were then packaged with the AAV8 serotype for in vivo delivery. $1 \times 10^{12}$ vector genomes (vg) per animal were administered with a single tail-vein injection and liver tissue was harvested three weeks later for analysis of miRNA and eGFP expression. As expected, mice transduced with scAAV8.miR26a.eGFP exhibited high-level expression of miR-26a in the liver (FIG. 4D). Fluorescent microscopy documented over 90% transduction of hepatocytes with both vectors (FIG. 4E). Importantly, it has previously been demonstrated that AAV8-mediated delivery of some short-hairpin RNA (shRNA) constructs induces acute liver toxicity due to competitive inhibition of the miRNA pathway (Grimm et al., 2006). scAAV8.miR26a.eGFP administration does not cause these effects, as demonstrated by normal levels of endogenously-expressed miRNAs in transduced livers (FIG. 4D) and an absence of any acute inflammation, fibrosis, or overt histologic evidence of toxicity (FIG. 4F). These data demonstrate that scAAV8 provides an effective, non-toxic means to deliver miRNAs to the liver.

Example 7

Figure 5A:
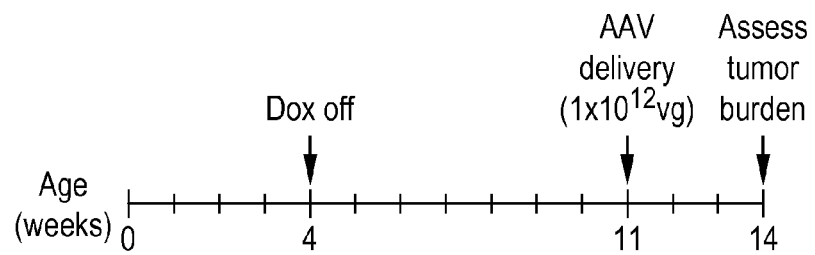
FIG. 5. AAV-mediated miR-26a delivery suppresses tumorigenesis in tet-o-MYC; LAP-tTA mice (A) Time-line of miR-26a therapeutic delivery experiment. (B) Gross tumor burden of livers from miR-26a-treated and control animals, as determined by quantification of tumor area using the ImageJ software package. The mean tumor burden in each treatment group is indicated by horizontal lines. Data points highlighted by asterisks represent animals that exhibited low AAV transduction efficiency. p value calculated by two-tailed t-test. (C) Representative images of livers from miR-26a-treated and control animals. (D) Liver:body weight ratios of miR-26a-treated and control animals. A chi-square statistic was used to compare the fraction of animals in each treatment group with a liver:body weight ratio above 0.1 (indicated by horizontal line). Data points highlighted by asterisks represent animals that exhibited low AAV transduction efficiency. (E) Representative livers 7 weeks following dox removal (dox off at 4 weeks of age, livers harvested at 11 weeks of age) to show baseline tumor burden in tet-o-MYC; LAP-tTA mice at time of AAV administration. (F) Low-power H&E-stained sections of liver lobes from treated and control animals to show lobular distribution of tumors in miR-26a-treated and control animals 21 days after AAV administration. (G) Percentage of GFP-positive hepatocytes in treated animals, as determined by fluorescent microscopy to show AAV transduction efficiency in miR-26a-treated and control animals. Asterisks in this panel and in (H) indicate animals which did not demonstrate a therapeutic response to miR-26a delivery. (H) Quantification of transduced vector genomes per cell as determined by qPCR.
Figure 5B:
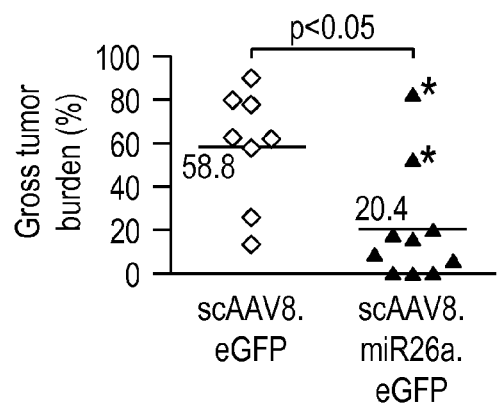
Figure 5D:
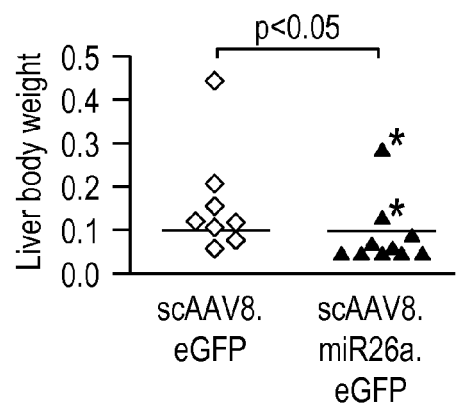
Figure 5C:
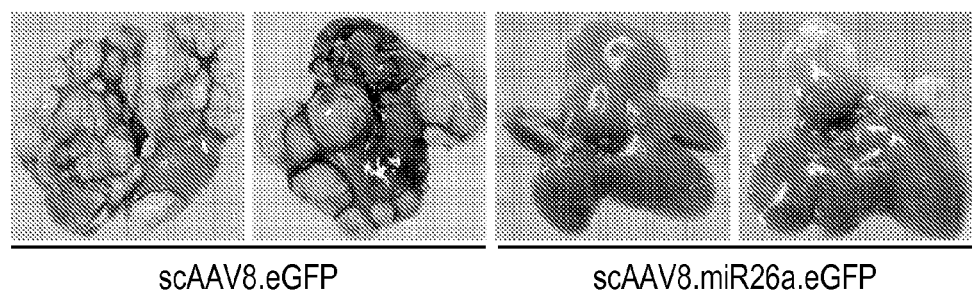
Figure 5E:
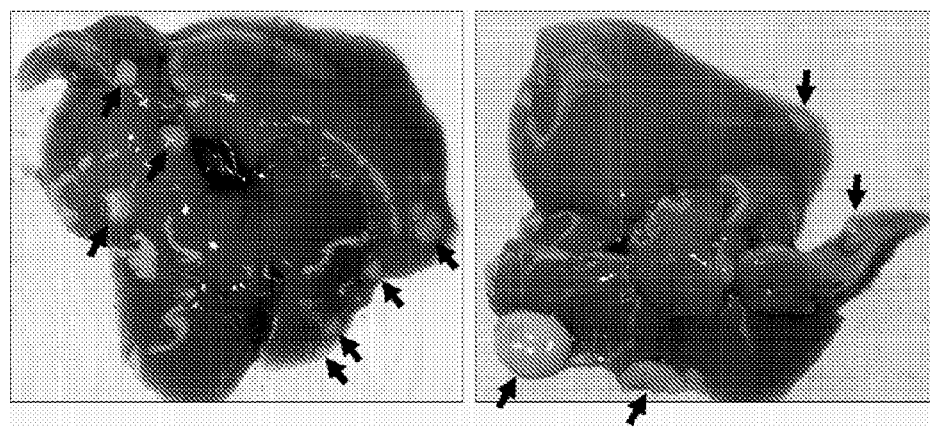
Figure 5F:
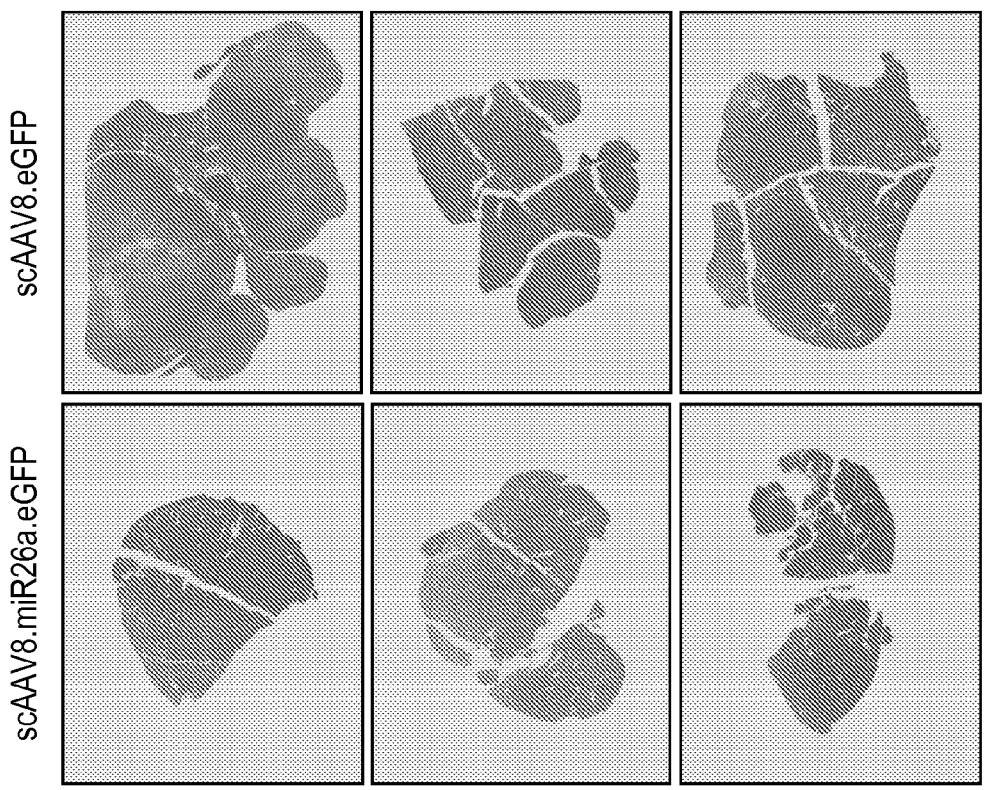

Therapeutic Delivery of miR-26a Suppresses Tumorigenesis in tet-o-MYC; LAP-tTA Mice To assess the therapeutic efficacy of miR-26a delivery for liver cancer, we administered scAAV8.miR26a.eGFP, or scAAV8.eGFP as a negative control, to tumor-bearing tet-o-MYC; LAP-tTA mice. Animals were taken off Dox at 4 weeks of age and virus was administered at 11 weeks of age, a time-point at which animals typically have multiple small to medium size tumors (FIG. 5A, FIG. 5E). Three weeks later, animals were sacrificed and tumor burden was assessed. 6 out of 8 mice treated with control virus developed fulminant disease in which the majority of liver tissue was replaced with tumor tissue (FIG. 5B, C, F). In contrast, 8 of 10 scAAV8.miR26a.eGFP-treated animals were dramatically protected, exhibiting only small tumors or a complete absence of tumors upon gross inspection (FIG. 5B, p<0.05). Liver:body weight ratios were significantly lower as well in scAAV8.miR26a.eGFP-treated versus scAAV8.eGFP-treated animals (p<0.05), further documenting tumor suppression (FIG. 5D).

Figure 5G:
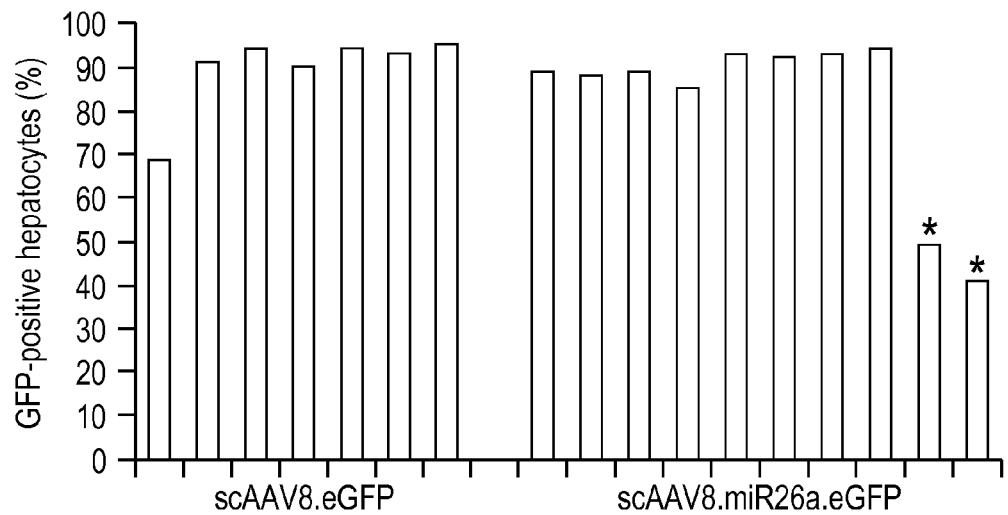
Figure 5H:
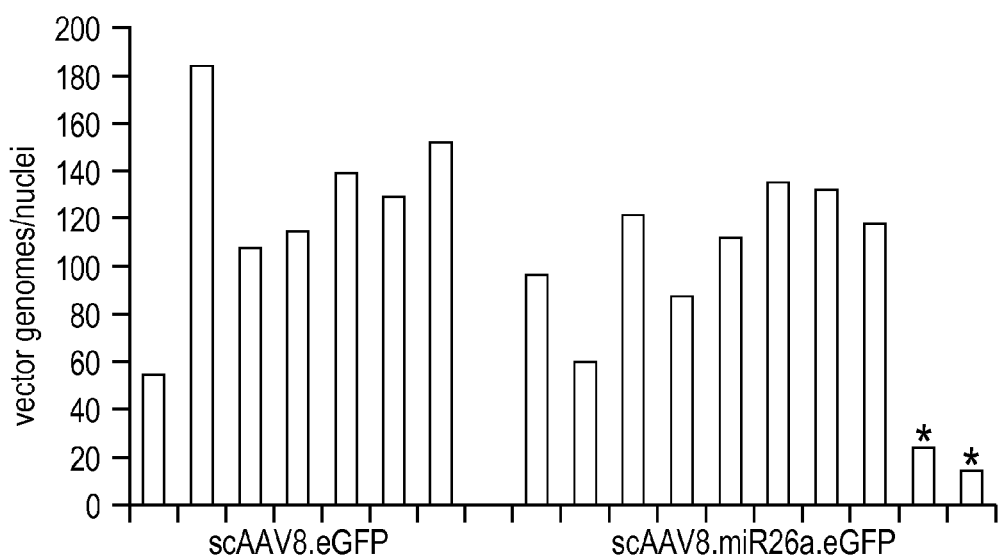

Aggressive liver tumors arose in 2 of 10 scAAV8.miR26a.eGFP-treated mice. To investigate the cause of these treatment failures, we assessed AAV transduction efficiency by scoring GFP positive hepatocytes and by quantifying transduced vector genomes by qPCR. Interestingly, these mice exhibited significantly lower transduction efficiency than the successfully treated animals (FIGS. 5G, H). This strongly suggests that the development of disease in these animals was a result of technical failure rather than biologic resistance to miR-26a-mediated tumor suppression. We conclude that efficient transduction of hepatocytes with scAAV8.miR26a.eGFP uniformly diminished disease progression in this model.

Example 8

Figure 6A:
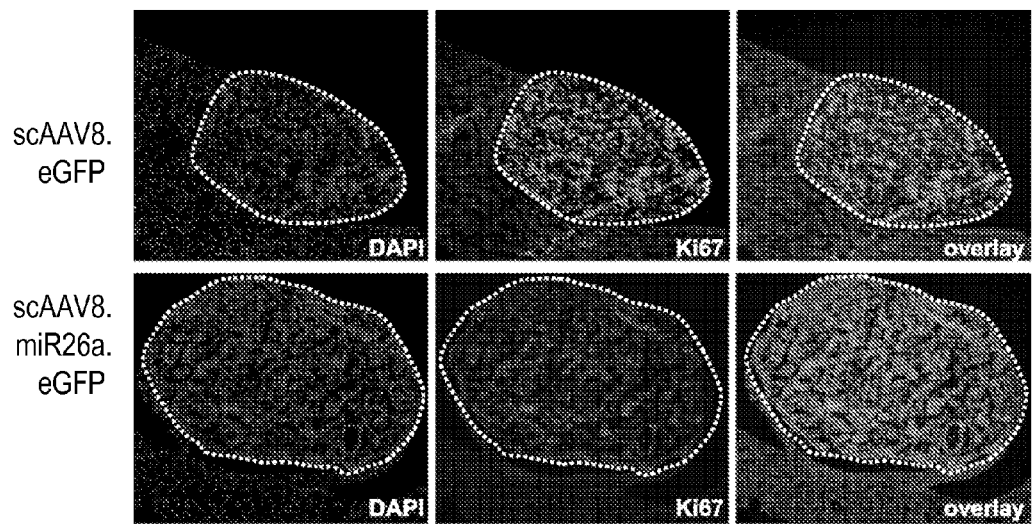
Figure 6B:
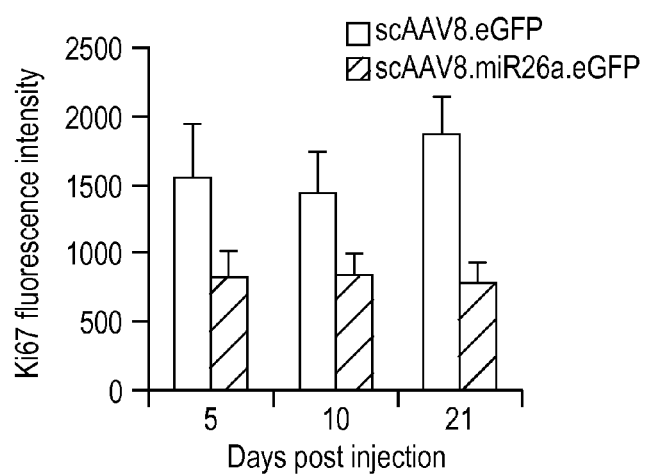
Figure 6C:
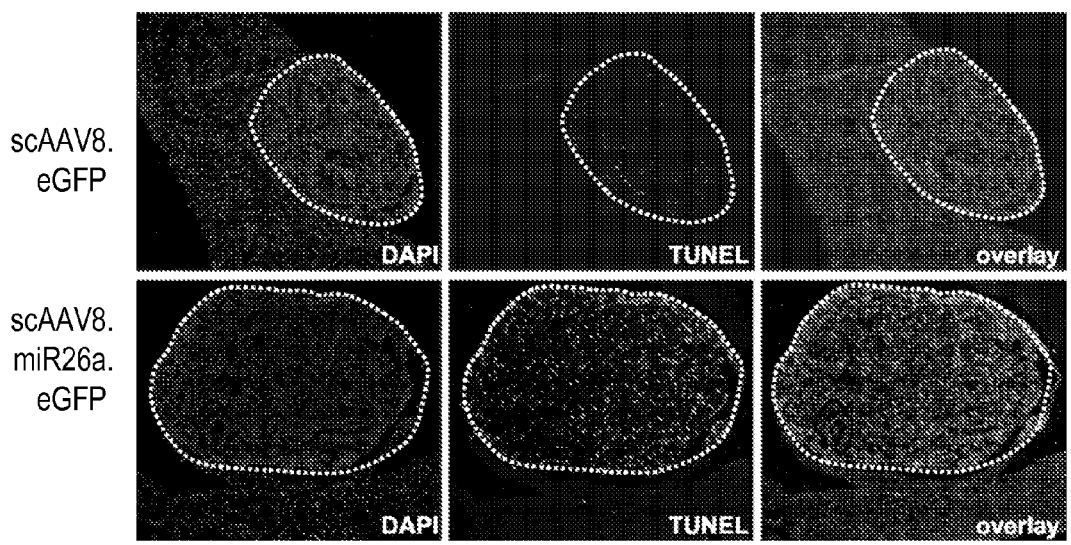
Figure 6D:
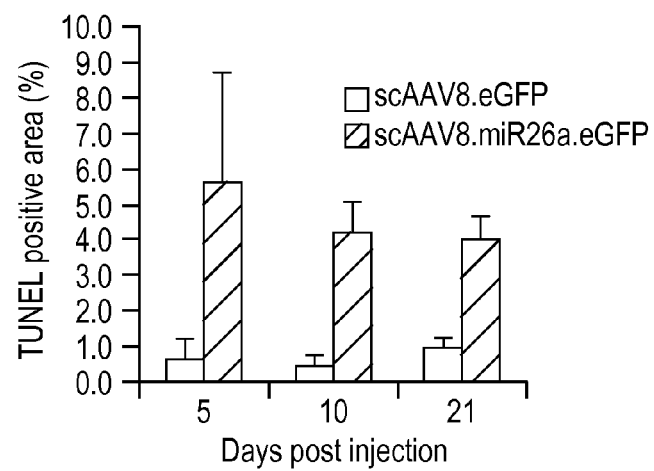
Figure 6E:
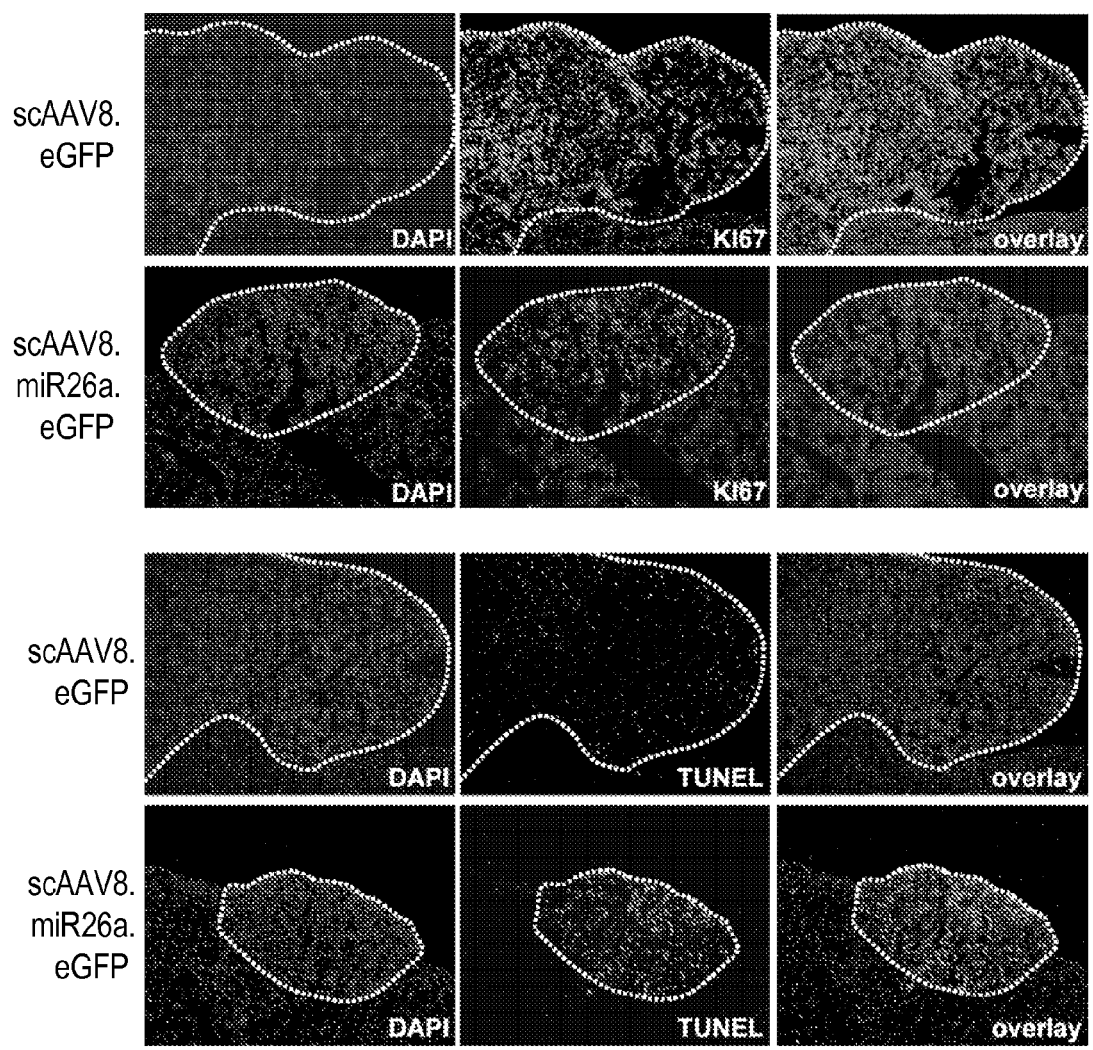
Figure 6F:
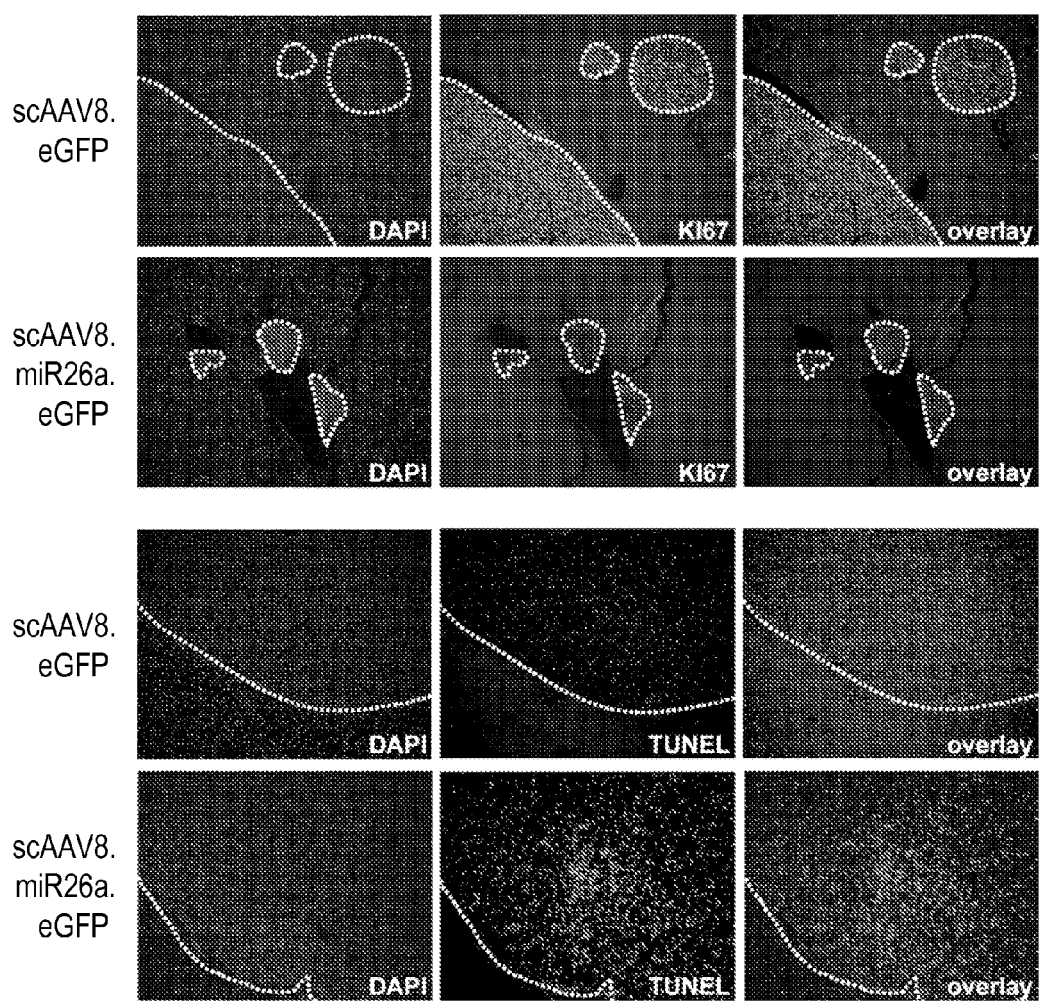

Delivery of miR-26a Reduces Cancer Cell Proliferation and Induces Tumor-Specific Apoptosis To ascertain the cellular mechanisms underlying miR-26a-mediated tumor suppression, we examined liver tissue in tumor-bearing mice 5, 10, and 21 days following vector administration (dox off at 4 weeks, virus administered at 11 weeks). Ki67 staining revealed rapid proliferation of tumor cells at all time-points in scAAV8.eGFP-treated animals (FIG. 6A, B, E. F). Consistent with our earlier demonstration that expression of miR-26a arrests the cell-cycle in HepG2 cells, we observed markedly reduced Ki67 staining in tumors following administration of scAAV8.miR26a.eGFP. No difference in Ki67 staining of non-tumor tissue was apparent between the treatment groups, although baseline Ki67 signal was low in normal liver reflecting the slow proliferative rate of adult hepatocytes.

Figure 6G:
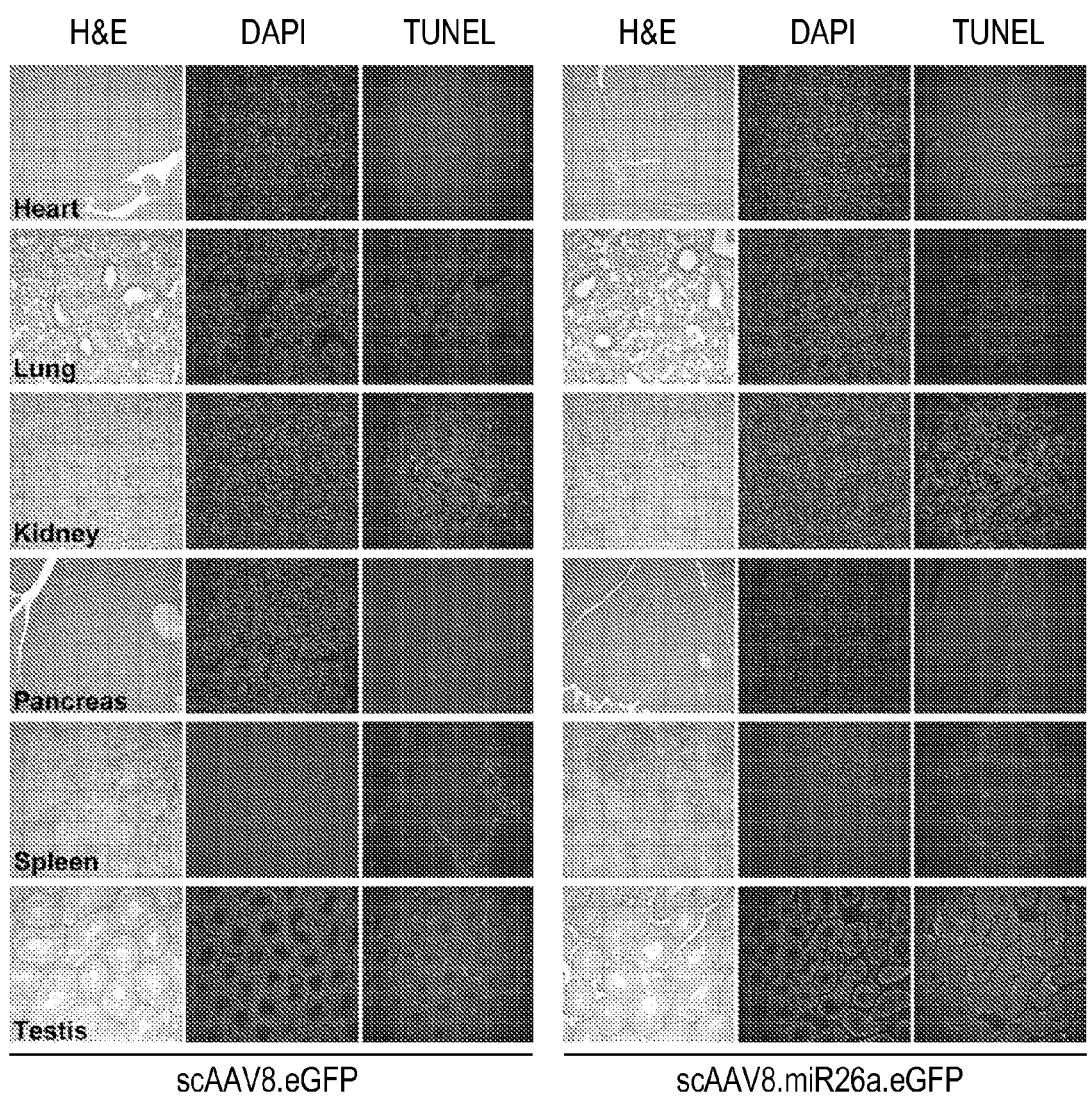

Treatment-induced apoptosis was also assessed by TUNEL staining. Apoptotic cells were rare in normal liver tissue and present at low levels in tumors from scAAV8.eGFP-treated animals at all time points (FIG. 6C-F). Remarkably, AAV-mediated delivery of miR-26a potently induced apoptosis specifically in tumor cells without measurably causing death of normal hepatocytes. To further investigate the specificity of miR-26a-induced apoptosis, we performed TUNEL staining on a broader panel of tissues including those with high proliferative indices (testis, spleen) and low proliferative indices (heart, lung, kidney, pancreas) (FIG. 6G). scAAV8.miR26a.eGFP administration did not cause a measurable increase in the frequency of apoptotic cells in any of these tissues. Together with the Ki67 data, these results document that miR-26a-mediated tumor suppression is associated with rapid and sustained inhibition of cancer cell proliferation and highly-specific induction of tumor cell death.

REFERENCES

Alexander, I. E., Cunningham, S. C., Logan, G. J., and Christodoulou, J. (2008). Potential of AAV vectors in the treatment of metabolic disease. Gene Ther 15, 831-839.

Ambros, V. (2004). The functions of animal microRNAs. Nature 431, 350-355.

Baek, D., Villen, J., Shin, C., Camargo, F. D., Gygi, S. P., and Bartel, D. P. (2008). The impact of microRNAs on protein output. Nature 455, 64-71.

Beer, S., Zetterberg, A., Ihrie, R. A., McTaggart, R. A., Yang, Q., Bradon, N., Arvanitis, C., Attardi, L. D., Feng, S., Ruebner, B., et al. (2004). Developmental context determines latency of MYC-induced tumorigenesis. PLoS Biol 2, e332.

Betel, D., Wilson, M., Gabow, A., Marks, D. S., and Sander, C. (2008). The microRNA.org resource: targets and expression. Nucleic Acids Res 36, D149-153.

Bommer, G. T., Gerin, I., Feng, Y., Kaczorowski, A. J., Kuick, R., Love, R. E., Zhai, Y., Giordano, T. J., Qin, Z. S., Moore, B. B., et al. (2007). p53-Mediated Activation of miRNA34 Candidate Tumor-Suppressor Genes. Curr Biol 17, 1298-1307.

Calin, G. A., Cimmino, A., Fabbri, M., Ferracin, M., Wojcik, S. E., Shimizu, M., Taccioli, C., Zanesi, N., Garzon, R., Aqeilan, R. I., et al. (2008). MiR-15a and miR-16-1 cluster functions in human leukemia. Proc Natl Acad Sci USA 105, 5166-5171.

Calin, G. A., and Croce, C. M. (2006). MicroRNA signatures in human cancers. Nat Rev Cancer 6, 857-866.

Calin, G. A., Dumitru, C. D., Shimizu, M., Bichi, R., Zupo, S., Noch, E., Aldler, H., Rattan, S., Keating, M., Rai, K., et al. (2002). Frequent deletions and down-regulation of micro-RNA genes miR15 and miR16 at 13q14 in chronic lymphocytic leukemia. Proc Natl Acad Sci USA 99, 15524-15529.

Calin, G. A., Sevignani, C., Dumitru, C. D., Hyslop, T., Noch, E., Yendamuri, S., Shimizu, M., Rattan, S., Bullrich, F., Negrini, M., and Croce, C. M. (2004). Human microRNA genes are frequently located at fragile sites and genomic regions involved in cancers. Proc Natl Acad Sci USA 101, 2999-3004.

Carter, B. J. (2005). Adeno-associated virus vectors in clinical trials. Hum Gene Ther 16, 541-550.

Chang, T. C., and Mendell, J. T. (2007). microRNAs in vertebrate physiology and human disease. Annu Rev Genomics Hum Genet 8, 215-239.

Chang, T. C., Wentzel, E. A., Kent, O. A., Ramachandran, K., Mullendore, M., Lee, K. H., Feldmann, G., Yamakuchi, M., Ferlito, M., Lowenstein, C. J., et al. (2007). Transactivation of miR-34a by p53 Broadly Influences Gene Expression and Promotes Apoptosis. Mol Cell 26, 745-752.

Chang, T. C., Yu, D., Lee, Y. S., Wentzel, E. A., Arking, D. E., West, K. M., Dang, C. V., Thomas-Tikhonenko, A., and Mendell, J. T. (2008). Widespread microRNA repression by Myc contributes to tumorigenesis. Nat Genet 40, 43-50.

Clark, K. R., Liu, X., McGrath, J. P., and Johnson, P. R. (1999). Highly purified recombinant adeno-associated virus vectors are biologically active and free of detectable helper and wild-type viruses. Hum Gene Ther 10, 1031-1039.

de Fougerolles, A., Vornlocher, H. P., Maraganore, J., and Lieberman, J. (2007). Interfering with disease: a progress report on siRNA-based therapeutics. Nat Rev Drug Discov 6, 443-453.

Dews, M., Homayouni, A., Yu, D., Murphy, D., Sevignani, C., Wentzel, E., Furth, E. E., Lee, W. M., Enders, G. H., Mendell, J. T., and Thomas-Tikhonenko, A. (2006). Augmentation of tumor angiogenesis by a Myc-activated microRNA cluster. Nat Genet 38, 1060-1065.

Elmen, J., Lindow, M., Schutz, S., Lawrence, M., Petri, A., Obad, S., Lindholm, M., Hedtjarn, M., Hansen, H. F., Berger, U., et al. (2008). LNA-mediated microRNA silencing in non-human primates. Nature 452, 896-899.

Esau, C., Davis, S., Murray, S. F., Yu, X. X., Pandey, S. K., Pear, M., Watts, L., Booten, S. L., Graham, M., McKay, R., et al. (2006). miR-122 regulation of lipid metabolism revealed by in vivo antisense targeting. Cell Metab 3, 87-98.

Esquela-Kerscher, A., Trang, P., Wiggins, J. F., Patrawala, L., Cheng, A., Ford, L., Weidhaas, J. B., Brown, D., Bader, A. G., and Slack, F. J. (2008). The let-7 microRNA reduces tumor growth in mouse models of lung cancer. Cell Cycle 7, 759-764.

Felsher, D. W., and Bishop, J. M. (1999). Reversible tumorigenesis by MYC in hematopoietic lineages. Mol Cell 4, 199-207.

Franich, N. R., Fitzsimons, H. L., Fong, D. M., Klugmann, M., During, M. J., and Young, D. (2008). AAV vector-mediated RNAi of mutant huntingtin expression is neuroprotective in a novel genetic rat model of Huntington's disease. Mol Ther 16, 947-956.

Gao, G. P., Alvira, M. R., Wang, L., Calcedo, R., Johnston, J., and Wilson, J. M. (2002). Novel adeno-associated viruses from rhesus monkeys as vectors for human gene therapy. Proc Natl Acad Sci USA 99, 11854-11859.

Gaur, A., Jewell, D. A., Liang, Y., Ridzon, D., Moore, J. H., Chen, C., Ambros, V. R., and Israel, M. A. (2007). Characterization of microRNA expression levels and their biological correlates in human cancer cell lines. Cancer Res 67, 2456-2468.

Giering, J. C., Grimm, D., Storm, T. A., and Kay, M. A. (2008). Expression of shRNA from a tissue-specific pol II promoter is an effective and safe RNAi therapeutic. Mol Ther 16, 1630-1636.

Grimm, D., and Kay, M. A. (2007). RNAi and Gene Therapy: A Mutual Attraction. Hematology Am Soc Hematol Educ Program 2007, 473-481.

Grimm, D., Streetz, K. L., Jopling, C. L., Storm, T. A., Pandey, K., Davis, C. R., Marion, P., Salazar, F., and Kay, M. A. (2006). Fatality in mice due to oversaturation of cellular microRNA/short hairpin RNA pathways. Nature 441, 537-541.

Grimson, A., Farh, K. K., Johnston, W. K., Garrett-Engele, P., Lim, L. P., and Bartel, D. P. (2007). MicroRNA targeting specificity in mammals: determinants beyond seed pairing. Mol Cell 27, 91-105.

He, L., He, X., Lim, L. P., de Stanchina, E., Xuan, Z., Liang, Y., Xue, W., Zender, L., Magnus, J., Ridzon, D., et al. (2007a). A microRNA component of the p53 tumour suppressor network. Nature 447, 1130-1134.

He, L., He, X., Lowe, S. W., and Hannon, G. J. (2007b). microRNAs join the p53 network—another piece in the tumour-suppression puzzle. Nat Rev Cancer 7, 819-822.

He, L., Thomson, J. M., Hemann, M. T., Hernando-Monge, E., Mu, D., Goodson, S., Powers, S., Cordon-Cardo, C., Lowe, S. W., Hannon, G. J., and Hammond, S. M. (2005). A microRNA polycistron as a potential human oncogene. Nature 435, 828-833.

Hwang, H. W., Wentzel, E. A., and Mendell, J. T. (2007). A hexanucleotide element directs microRNA nuclear import. Science 315, 97-100.

Johnson, S. M., Grosshans, H., Shingara, J., Byrom, M., Jarvis, R., Cheng, A., Labourier, E., Reinert, K. L., Brown, D., and Slack, F. J. (2005). RAS is regulated by the let-7 microRNA family. Cell 120, 635-647.

Kashuba, V. I., Li, J., Wang, F., Senchenko, V. N., Protopopov, A., Malyukova, A., Kutsenko, A. S., Kadyrova, E., Zabarovska, V. I., Muravenko, O. V., et al. (2004). RBSP3 (HYA22) is a tumor suppressor gene implicated in major epithelial malignancies. Proc Natl Acad Sci USA 101, 4906-4911.

Kato, M., and Slack, F. J. (2008). microRNAs: small molecules with big roles—C. elegans to human cancer. Biol Cell 100, 71-81.

Kim, V. N. (2005). MicroRNA biogenesis: coordinated cropping and dicing. Nat Rev Mol Cell Biol 6, 376-385.

Kloosterman, W. P., and Plasterk, R. H. (2006). The diverse functions of microRNAs in animal development and disease. Dev Cell 11, 441-450.

Krek, A., Grun, D., Poy, M. N., Wolf, R., Rosenberg, L., Epstein, E. J., MacMenamin, P., da Piedade, I., Gunsalus, K. C., Stoffel, M., and Rajewsky, N. (2005). Combinatorial microRNA target predictions. Nat Genet 37, 495-500.

Krutzfeldt, J., Rajewsky, N., Braich, R., Rajeev, K. G., Tuschl, T., Manoharan, M., and Stoffel, M. (2005). Silencing of microRNAs in vivo with 'antagomirs'. Nature 438, 685-689.

Kumar, M. S., Erkeland, S. J., Pester, R. E., Chen, C. Y., Ebert, M. S., Sharp, P. A., and Jacks, T. (2008). Suppression of non-small cell lung tumor development by the let-7 microRNA family. Proc Natl Acad Sci USA 105, 3903-3908.

Kumar, M. S., Lu, J., Mercer, K. L., Golub, T. R., and Jacks, T. (2007). Impaired microRNA processing enhances cellular transformation and tumorigenesis. Nat Genet 39, 673-677.

Landgraf, P., Rusu, M., Sheridan, R., Sewer, A., Iovino, N., Aravin, A., Pfeffer, S., Rice, A., Kamphorst, A. O., Landthaler, M., et al. (2007). A mammalian microRNA expression atlas based on small RNA library sequencing. Cell 129, 1401-1414.

Linsley, P. S., Schelter, J., Burchard, J., Kibukawa, M., Martin, M. M., Bartz, S. R., Johnson, J. M., Cummins, J. M., Raymond, C. K., Dai, H., et al. (2007). Transcripts targeted by the microRNA-16 family cooperatively regulate cell cycle progression. Mol Cell Biol 27, 2240-2252.

Love, T. M., Moffett, H. F., and Novina, C. D. (2008). Not miR-ly small RNAs: big potential for microRNAs in therapy. J Allergy Clin Immunol 121, 309-319.

Lu, J., Getz, G., Miska, E. A., Alvarez-Saavedra, E., Lamb, J., Peck, D., Sweet-Cordero, A., Ebert, B. L., Mak, R. H., Ferrando, A. A., et al. (2005). MicroRNA expression profiles classify human cancers. Nature 435, 834-838.

Lujambio, A., and Esteller, M. (2007). CpG island hypermethylation of tumor suppressor microRNAs in human cancer. Cell Cycle 6, 1455-1459.

Maguire, A. M., Simonelli, F., Pierce, E. A., Pugh, E. N., Jr., Mingozzi, F., Bennicelli, J., Banfi, S., Marshall, K. A., Testa, F., Surace, E. M., et al. (2008). Safety and efficacy of gene transfer for Leber's congenital amaurosis. N Engl J Med 358, 2240-2248.

McBride, J. L., Boudreau, R. L., Harper, S. Q., Staber, P. D., Monteys, A. M., Martins, I., Gilmore, B. L., Burstein, H., Peluso, R. W., Polisky, B., et al. (2008). Artificial miRNAs mitigate shRNA-mediated toxicity in the brain: implications for the therapeutic development of RNAi. Proc Natl Acad Sci USA 105, 5868-5873.

McCarty, D. M. (2008). Self-complementary AAV vectors; advances and applications. Mol Ther 16, 1648-1656.

McCarty, D. M., Fu, H., Monahan, P. E., Toulson, C. E., Naik, P., and Samulski, R. J. (2003). Adeno-associated virus terminal repeat (TR) mutant generates self-complementary vectors to overcome the rate-limiting step to transduction in vivo. Gene Ther 10, 2112-2118.

Mendell, J. T. (2008). miRiad roles for the miR-17-92 cluster in development and disease. Cell 133, 217-222.

Nakai, H., Fuess, S., Storm, T. A., Muramatsu, S., Nara, Y., and Kay, M. A. (2005). Unrestricted hepatocyte transduction with adeno-associated virus serotype 8 vectors in mice. J Virol 79, 214-224.

O'Donnell, K. A., Wentzel, E. A., Zeller, K. I., Dang, C. V., and Mendell, J. T. (2005). c-Myc-regulated microRNAs modulate E2F1 expression. Nature 435, 839-843.

Ota, A., Tagawa, H., Kaman, S., Tsuzuki, S., Karpas, A., Kira, S., Yoshida, Y., and Seto, M. (2004). Identification and characterization of a novel gene, C13orf25, as a target for 13q31-q32 amplification in malignant lymphoma. Cancer Res 64, 3087-3095.

Park, K., Kim, W. J., Cho, Y. H., Lee, Y. I., Lee, H., Jeong, S., Cho, E. S., Chang, S. I., Moon, S. K., Kang, B. S., et al. (2008). Cancer gene therapy using adeno-associated virus vectors. Front Biosci 13, 2653-2659.

Pathak, A., Vyas, S. P., and Gupta, K. C. (2008). Nano-vectors for efficient liver specific gene transfer. Int J Nanomedicine 3, 31-49.

Raver-Shapira, N., Marciano, E., Meiri, E., Spector, Y., Rosenfeld, N., Moskovits, N., Bentwich, Z., and Oren, M. (2007). Transcriptional activation of miR-34a contributes to p53-mediated apoptosis. Mol Cell 26, 731-743.

Roberts, L. R. (2008). Sorafenib in liver cancer—just the beginning. N Engl J Med 359, 420-422.

Rodino-Klapac, L. R., Janssen, P. M., Montgomery, C. L., Coley, B. D., Chicoine, L. G., Clark, K. R., and Mendell, J. R. (2007). A translational approach for limb vascular delivery of the micro-dystrophin gene without high volume or high pressure for treatment of Duchenne muscular dystrophy. J Transl Med 5, 45.

Schnepp, B. C., Clark, K. R., Klemanski, D. L., Pacak, C. A., and Johnson, P. R. (2003). Genetic fate of recombinant adeno-associated virus vector genomes in muscle. J Virol 77, 3495-3504.

Selbach, M., Schwanhausser, B., Thierfelder, N., Fang, Z., Khanin, R., and Rajewsky, N. (2008). Widespread changes in protein synthesis induced by microRNAs. Nature 455, 58-63.

Shachaf, C. M., Kopelman, A. M., Arvanitis, C., Karlsson, A., Beer, S., Mandl, S., Bachmann, M. H., Borowsky, A. D., Ruebner, B., Cardiff, R. D., et al. (2004). MYC inactivation uncovers pluripotent differentiation and tumour dormancy in hepatocellular cancer. Nature 431, 1112-1117.

Stenvang, J., Silahtaroglu, A. N., Lindow, M., Elmen, J., and Kauppinen, S. (2008). The utility of LNA in microRNA-based cancer diagnostics and therapeutics. Semin Cancer Biol 18, 89-102.

Tarasov, V., Jung, P., Verdoodt, B., Lodygin, D., Epanchintsev, A., Menssen, A., Meister, G., and Hermeking, H. (2007). Differential regulation of microRNAs by p53 revealed by massively parallel sequencing: miR-34a is a p53 target that induces apoptosis and G1-arrest. Cell Cycle 6, 1586-1593.

Thorgeirsson, S. S., and Grisham, J. W. (2002). Molecular pathogenesis of human hepatocellular carcinoma. Nat Genet 31, 339-346.

Valencia-Sanchez, M. A., Liu, J., Hannon, G. J., and Parker, R. (2006). Control of translation and mRNA degradation by miRNAs and siRNAs. Genes Dev 20, 515-524.

Ventura, A., Young, A. G., Winslow, M. M., Linault, L., Meissner, A., Erkeland, S. J., Newman, J., Bronson, R. T., Crowley, D., Stone, J. R., et al. (2008). Targeted deletion reveals essential and overlapping functions of the miR-17~92 family of miRNA clusters. Cell 132, 875-886.

Vermeulen, K., Van Bockstaele, D. R., and Berneman, Z. N. (2003). The cell cycle: a review of regulation, deregulation and therapeutic targets in cancer. Cell Prolif 36, 131-149.

Visone, R., Pallante, P., Vecchione, A., Cirombella, R., Ferracin, M., Ferraro, A., Volinia, S., Coluzzi, S., Leone, V., Borbone, E., et al. (2007). Specific microRNAs are down-regulated in human thyroid anaplastic carcinomas. Oncogene 26, 7590-7595.

Wakabayashi-Ito, N., and Nagata, S. (1994). Characterization of the regulatory elements in the promoter of the human elongation factor-1 alpha gene. J Biol Chem 269, 29831-29837.

Wang, Z., Ma, H. I., Li, J., Sun, L., Zhang, J., and Xiao, X. (2003). Rapid and highly efficient transduction by double-stranded adeno-associated virus vectors in vitro and in vivo. Gene Ther 10, 2105-2111.

Wienholds, E., Kloosterman, W. P., Miska, E., Alvarez-Saavedra, E., Berezikov, E., de Bruijn, E., Horvitz, H. R., Kauppinen, S., and Plasterk, R. H. (2005). MicroRNA expression in zebrafish embryonic development. Science 309, 310-311.

Xi, Y., Shalgi, R., Fodstad, O., Pilpel, Y., and Ju, J. (2006). Differentially regulated micro-RNAs and actively translated messenger RNA transcripts by tumor suppressor p53 in colon cancer. Clin Cancer Res 12, 2014-2024.

Xiao, C., Srinivasan, L., Calado, D. P., Patterson, H. C., Zhang, B., Wang, J., Henderson, J. M., Kutok, J. L., and Rajewsky, K. (2008). Lymphoproliferative disease and autoimmunity in mice with increased miR-17-92 expression in lymphocytes. Nat Immunol 9, 405-414.

Zhang, L., Huang, J., Yang, N., Greshock, J., Megraw, M. S., Giannakakis, A., Liang, S., Naylor, T. L., Barchetti, A., Ward, M. R., et al. (2006). microRNAs exhibit high frequency genomic alterations in human cancer. Proc Natl Acad Sci USA 103, 9136-9141.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

TABLE 1

Primers used in luciferase reporter assays (FIG. 3)

| | Forward primer sequence (5'-3') | Reverse primer sequence (5'-3') |
|---|---|---|
| CCND2.XbaI amplification | ATCGATTCTAGAGGTGCAAAGATAGA TGGCTGA (SEQ ID NO: 12) | ATCGATTCTAGAAACAAATAGCTTCATT ACCTGTCAA (SEQ. ID NO: 16) |
| CCNDE2.XbaI amplification | ATCGATTCTAGATGACTAGTGCAATTT GGTTCTTG (SEQ ID NO: 13) | ATCGATTCTAGAAGAGCACAGGTTGAAC ACCA (SEQ ID NO: 17) |
| CCND2 mutagenesis | GCAAAGTTGTATTCAGCGAAGTAGTAT TTTTCTTCCTCTCCACTTCTTAGAGGC (SEQ ID NO: 14) | GCCTCTAAGAAGTGGAGAGGAAGAAAA ATACTACTTCGCTGAATACAACTTTGC (SEQ ID NO: 18) |
| CCNE2 mutagenesis | CTAATTTATCTATAGCTGCTATAGCAA GCTATTATAAAAGTAGTATTTCTACAA ATGGTGAAATTTAATGTTT (SEQ ID NO: 15) | AAACATTAAATTTCACCATTTGTAGAAA TACTACTTTTATAATAGCTTGCTATAGCA GCTATAGATAAATTAG (SEQ ID NO: 19) |

TABLE 2

Primers used in constructing scAAV.miR-26a, scAAV.miR-26a.eGFP, and pcDNA-miR-122a (FIG. 4)

| | Forward primer sequence (5'-3') | Reverse primer sequence (5'-3') |
|---|---|---|
| miR-26a-2.NbeI/NotI amplification | CCGCCGGCTAGCCGGCAGGGTGTCTGT CTAGT (SEQ ID NO: 20) | AAGGAAAAAAGCGGCCGCCAGGCTTC CAATGGATCAGT (SEQ ID NO: 23) |
| miR-26a-2.FseI amplification | ATCGATCGGGCCGGCCCCCTGGTGCAA TTCATTACC (SEQ ID NO: 21) | ATCGATCGGGCCGGCCATCAGTGGTCC CAACCTCAA (SEQ ID NO: 24) |

TABLE 2-continued

Primers used in constructing scAAV.miR-26a, scAAV.miR-26a.eGFP, and pcDNA-miR-122a (FIG. 4)

| | Forward primer sequence (5'-3') | Reverse primer sequence (5'-3') |
|---|---|---|
| miR-112a.XhoI amplification | ATACCGCTCGAGTTGCAAACAGAGTTCCTGTCCA (SEQ ID NO: 22) | ATACCGCTCGAGAGCATGTGAGAGGCAGGGTTC (SEQ ID NO: 25) |

TABLE 3

Primers and probes used in Taqman assays for viral genome quantitation (FIG. 5G)

| | Forward primer sequence (5'-3') | Reverse primer sequence (5'-3') | Taqman probe sequence (5'-3') |
|---|---|---|---|
| EF1α Taqman amplicon | GGTGAGTCACCCACACAAAGG (SEQ ID NO: 26) | GGTACTCCGTGGAGTCACATGAA (SEQ ID NO: 28) | AAAGGGCCTTTCCGTCCTCAGCC (SEQ ID NO: 30) |
| eGFP Taqman amplicon | CACTACCTGAGCACCCAGTC (SEQ ID NO: 27) | TCCAGCAGGACCATGTGATC (SEQ ID NO: 29) | TGAGCAAAGACCCCAACGAGAAGCG (SEQ ID NO: 31) |

What is claimed is:

1. A method of reducing hepatic tumorigenesis in a subject, the method comprising administering to the subject an expression vector including a polynucleotide encoding miR-26a, thereby reducing hepatic tumor formation, wherein the polynucleotide encoding miR-26a is SEQ ID NO:10.

2. A method of treating a hepatic neoplasia in a subject, the method comprising administering to the subject an expression vector including a polynucleotide encoding miR-26a, thereby treating or preventing the neoplasia, wherein the polynucleotide encoding miR-26a is SEQ ID NO:10.

3. A method of treating a hepatic neoplasia, the method comprising contacting a hepatic neoplastic cell with an expression vector including a polynucleotide encoding miR-26a, thereby treating or preventing the neoplasia, wherein the polynucleotide encoding miR-26a is SEQ ID NO:10.

4. The method of claim 1, wherein the vector is a viral expression vector.

5. The method of claim 1, wherein the vector is an adenoviral vector, an adeno-associated viral vector, or a lentiviral vector.

6. The method of claim 5, wherein the viral vector is a self-complementary adeno-associated viral vector.

7. The method of claim 6, wherein the adeno-associated viral vector is selected from the group consisting of AAV1, AAV2, AAV3, AAV4, AAV5, AAV6, AAV7, AAV8, and AAV9.

8. The method of claim 5, wherein the adeno-associated viral vector is a chimeric adeno-associated viral vector.

9. The method of claim 1, wherein the expression vector comprises inverted terminal repeats (ITRs) flanking the polynucleotide encoding miR-26a.

10. The method of claim 1, wherein the polynucleotide encoding miR-26a is positioned for expression adjacent to an elongation factor-1α (EF1α) promoter sequence.

* * * * *

SEQUENCE LISTING

<160> NUMBER OF SEQ ID NOS: 44

<210> SEQ ID NO 1
<211> LENGTH: 74
<212> TYPE: RNA
<213> ORGANISM: Homo sapiens

<400> SEQUENCE: 1
guggccucgu ucaaguaauc caggauaggc ugugcagguc ccaaugggcc uauucggua        60 cugcacgggg acgc                                                        74

<210> SEQ ID NO 2
<211> LENGTH: 22
<212> TYPE: RNA
<213> ORGANISM: Homo sapiens

<400> SEQUENCE: 2
uucaaguaau ccaggauagg cu                                               22

<210> SEQ ID NO 3
<211> LENGTH: 77
<212> TYPE: RNA
<213> ORGANISM: Homo sapiens

<400> SEQUENCE: 3
guggccucgu ucaaguaauc caggauaggc ugugcagguc ccaaugggcc uauucuuggu        60
uacuugcacg gggacgc                                                     77

<210> SEQ ID NO 4
<211> LENGTH: 84
<212> TYPE: RNA
<213> ORGANISM: Homo sapiens

<400> SEQUENCE: 4
ggcuguggcu ggauucaagu aauccaggau aggcuguuuc caucugugag gccuauucuu        60
gauuacuugu uucuggaggc agcu                                             84

```
<210> SEQ ID NO 5
<211> LENGTH: 22
<212> TYPE: RNA
<213> ORGANISM: Homo sapiens

<400> SEQUENCE: 5
uucaaguaau ccaggauagg cu                                              22

<210> SEQ ID NO 6
<211> LENGTH: 84
<212> TYPE: RNA
<213> ORGANISM: Homo sapiens

<400> SEQUENCE: 6
ggcuguggcu ggauucaagu aauccaggau aggcuguuuc caucugugag gccuauucuu     60
gauuacuugu uucuggaggc agcu                                            84

<210> SEQ ID NO 7
<211> LENGTH: 77
<212> TYPE: RNA
<213> ORGANISM: Homo sapiens

<400> SEQUENCE: 7
ccgggaccca guucaaguaa uucaggauag guugugugcu guccagccug uucuccauua     60
cuuggcucgg ggaccgg                                                    77

<210> SEQ ID NO 8
<211> LENGTH: 20
<212> TYPE: RNA
<213> ORGANISM: Homo sapiens

<400> SEQUENCE: 8
uucaaguaau ucaggauggu                                                 20

<210> SEQ ID NO 9
<211> LENGTH: 57
<212> TYPE: RNA
<213> ORGANISM: Homo sapiens

<400> SEQUENCE: 9
uucaaguaau ucaggauagg uugugugcug uccagccugu ucuccauuac uuggcuc        57

<210> SEQ ID NO 10
<211> LENGTH: 248
<212> TYPE: DNA
<213> ORGANISM: Homo sapiens

<400> SEQUENCE: 10
ccctggtgca attcattacc taatcatgac ctggacagac tgtcctgtcg gagccaagga     60
cagaaagctc ccatagaggc tgtggctgga ttcaagtaat ccaggatagg ctgtttccat    120
ctgtgaggcc tattcttgat tacttgtttc tggaggcagc tgatggtccg ccgccggaaa    180
cagagatggc tcctgggaca tggtgtgtgc gcttcttcct gagccaggtt gaggttggga    240
ccactgat                                                             248

<210> SEQ ID NO 11
<211> LENGTH: 2427
<212> TYPE: DNA
<213> ORGANISM: Artificial Sequence
<220> FEATURE:
<223> OTHER INFORMATION: Description of Artificial Sequence: Synthetic
``` polynucleotide

<400> SEQUENCE: 11

| | | | | | |
|---|---|---|---|---|---|
| cagcagctgc | gcgctcgctc | gctcactgag | gccgcccggg | caaagcccgg | gcgtcgggcg | 60 |
| acctttggtc | gcccggcctc | agtgagcgag | cgagcgcgca | gagagggagt | gggggttatcg | 120 |
| gcgcgccact | agtgaggctc | cggtgcccgt | cagtgggcag | agcgcacatc | gcccacagtc | 180 |
| cccgagaagt | tggggggagg | ggtcggcaat | tgaaccggtg | cctagagaag | gtggcgcggg | 240 |
| gtaaactggg | aaagtgatgt | cgtgtactgg | ctccgccttt | ttcccgaggg | tgggggagaa | 300 |
| ccgtatataa | gtgcagtagt | cgccgtgaac | gttctttttc | gcaacgggtt | tgccgccaga | 360 |
| acacaggtaa | gtgccgtgtg | tggttcccgc | gggcggcgac | ggggcccgtg | cgtcccagcg | 420 |
| cacatgttcg | gcgaggcggg | gcctgcgagc | gcggccaccg | agaatcggac | gggggtagtc | 480 |
| tcaagctggc | cggccccctg | gtgcaattca | ttacctaatc | atgacctgga | cagactgtcc | 540 |
| tgtcggagcc | aaggacagaa | agctcccata | gaggctgtgg | ctggattcaa | gtaatccagg | 600 |
| ataggctgtt | tccatctgtg | aggcctattc | ttgattactt | gtttctggag | gcagctgatg | 660 |
| gtccgccgcc | ggaaacagag | atggctcctg | ggacatggtg | tgtgcgcttc | ttcctgagcc | 720 |
| aggttgaggt | tgggaccact | gatggccggc | ctgctctggt | gcctggcctc | gcgccgccgt | 780 |
| gtatcgcccc | gccctgggcg | gcaaggctgg | cccggtcggc | accagttgcg | tgagcggaaa | 840 |
| gatggccgct | tcccggccct | gctgcaggga | gctcaaaatg | gaggacgcgg | cgctcgggag | 900 |
| agcgggcggg | tgagtcaccc | acacaaagga | aaagggcctt | tccgtcctca | gccgtcgctt | 960 |
| catgtgactc | cacggagtac | cgggcgccgt | ccaggcacct | cgattagttc | tcgagctttt | 1020 |
| ggagtacgtc | gtctttaggt | tgggggggagg | ggttttatgc | gatggagttt | ccccacactg | 1080 |
| agtgggtgga | gactgaagtt | aggccagctt | ggcacttgat | gtaattctcc | ttggaatttg | 1140 |
| cccttttga | gtttggatct | tggttcattc | tcaagcctca | gacagtggtt | caaagttttt | 1200 |
| ttcttccatt | tcaggtgtcg | tgaaaagcta | gcgctaccgg | actcagatct | cgagctcaag | 1260 |
| cttcgaattc | tgcagtcgac | ggtaccgcgg | gcccgggatc | caccggtcgc | caccatggtg | 1320 |
| agcaagggcg | aggagctgtt | caccggggtg | gtgcccatcc | tggtcgagct | ggacggcgac | 1380 |
| gtaaacggcc | acaagttcag | cgtgtccggc | gagggcgagg | gcgatgccac | ctacggcaag | 1440 |
| ctgaccctga | agttcatctg | caccaccggc | aagctgcccg | tgccctggcc | caccctcgtg | 1500 |
| accaccctga | cctacggcgt | gcagtgcttc | agccgctacc | ccgaccacat | gaagcagcac | 1560 |
| gacttcttca | agtccgccat | gcccgaaggc | tacgtccagg | agcgcaccat | cttcttcaag | 1620 |
| gacgacggca | actacaagac | ccgcgccgag | gtgaagttcg | agggcgacac | cctggtgaac | 1680 |
| cgcatcgagc | tgaagggcat | cgacttcaag | gaggacggca | acatcctggg | gcacaagctg | 1740 |
| gagtacaact | acaacagcca | caacgtctat | atcatggccg | acaagcagaa | gaacggcatc | 1800 |
| aaggtgaact | tcaagatccg | ccacaacatc | gaggacggca | gcgtgcagct | cgccgaccac | 1860 |
| taccagcaga | acacccccat | cggcgacggc | cccgtgctgc | tgcccgacaa | ccactacctg | 1920 |
| agcacccagt | ccgccctgag | caaagacccc | aacgagaagc | gcgatcacat | ggtcctgctg | 1980 |
| gagttcgtga | ccgccgccgg | gatcactctc | ggcatggacg | agctgtacaa | gtaaagcggc | 2040 |
| cgcgggatc | cagacatgat | aagatacatt | gatgagtttg | gacaaaccac | aactagaatg | 2100 |
| cagtgaaaaa | aatgctttat | ttgtgaaatt | tgtgatgcta | ttgctttatt | tgtaaccatt | 2160 |
| ataagctgca | ataaacaagt | taacaacaac | aattgcattc | attttatgtt | tcaggttcag | 2220 |
| ggggaggtgt | gggaggtttt | tttctagagc | atggctacgt | agataagtag | catggcgggt | 2280 |

```
taatcattaa ctacaaggaa cccctagtga tggagttggc cactccctct ctgcgcgctc    2340
gctcgctcac tgaggccggg cgaccaaagg tcgcccgacg cccgggcttt gcccgggcgg    2400
cctcagtgag cgagcgagcg cgccagc                                        2427
```

```
<210> SEQ ID NO 12
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
atcgattcta gaggtgcaaa gatagatggc tga                                   33

<210> SEQ ID NO 13
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
atcgattcta gatgactagt gcaatttggt tcttg                                 35

<210> SEQ ID NO 14
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gcaaagttgt attcagcgaa gtagtatttt tcttcctctc cacttcttag aggc            54

<210> SEQ ID NO 15
<211> LENGTH: 73
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ctaatttatc tatagctgct atagcaagct attataaaag tagtatttct acaaatggtg      60
aaatttaatg ttt                                                        73

<210> SEQ ID NO 16
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
atcgattcta gaaacaaata gcttcattac ctgtcaa                               37

<210> SEQ ID NO 17
<211> LENGTH: 32
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 17
atcgattcta gaagagcaca ggttgaacac ca                                     32

<210> SEQ ID NO 18
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gcctctaaga agtggagagg aagaaaaata ctacttcgct gaatacaact ttgc             54

<210> SEQ ID NO 19
<211> LENGTH: 73
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
aaacattaaa tttcaccatt tgtagaaata ctacttttat aatagcttgc tatagcagct       60
atagataaat tag                                                          73

<210> SEQ ID NO 20
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ccgccggcta gccggcaggg tgtctgtcta gt                                     32

<210> SEQ ID NO 21
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
atcgatcggg ccggcccect ggtgcaattc attacc                                 36

<210> SEQ ID NO 22
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ataccgctcg agttgcaaac agagttcctg tcca                                   34

<210> SEQ ID NO 23
<211> LENGTH: 38
<212> TYPE: DNA
<213> ORGANISM: Artificial Sequence
<220> FEATURE:
<223> OTHER INFORMATION: Description of Artificial Sequence: Synthetic -continued

```
primer

<400> SEQUENCE: 23
aaggaaaaaa gcggccgcca ggcttccaat ggatcagt                              38

<210> SEQ ID NO 24
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
atcgatcggg ccggccatca gtggtcccaa cctcaa                                36

<210> SEQ ID NO 25
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ataccgctcg agagcatgtg agaggcaggg ttc                                   33

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ggtgagtcac ccacacaaag g                                                21

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
cactacctga gcacccagtc                                                  20

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ggtactccgt ggagtcacat gaa                                              23

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

-continued

```
<400> SEQUENCE: 29
tccagcagga ccatgtgatc                                            20

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 30
aaagggcctt tccgtcctca gcc                                        23

<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 31
tgagcaaaga ccccaacgag aagcg                                      25

<210> SEQ ID NO 32
<211> LENGTH: 21
<212> TYPE: RNA
<213> ORGANISM: Homo sapiens

<400> SEQUENCE: 32
uucaaguaau ccaggauagg c                                          21

<210> SEQ ID NO 33
<211> LENGTH: 17
<212> TYPE: RNA
<213> ORGANISM: Homo sapiens

<400> SEQUENCE: 33
cagcguacuu gaauuuu                                               17

<210> SEQ ID NO 34
<211> LENGTH: 16
<212> TYPE: RNA
<213> ORGANISM: Mus sp.

<400> SEQUENCE: 34
cauuguacuu gaagac                                                16

<210> SEQ ID NO 35
<211> LENGTH: 15
<212> TYPE: RNA
<213> ORGANISM: Rattus sp.

<400> SEQUENCE: 35
cauuguacuu gaaga                                                 15

<210> SEQ ID NO 36
<211> LENGTH: 16
<212> TYPE: RNA
<213> ORGANISM: Canis lupus

<400> SEQUENCE: 36
cagcguacuu gaauuu                                                16
```

```
<210> SEQ ID NO 37
<211> LENGTH: 17
<212> TYPE: RNA
<213> ORGANISM: Gallus gallus

<400> SEQUENCE: 37
caguguacuu gaauuua                                                    17

<210> SEQ ID NO 38
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
cagcgaagua guauuuu                                                    17

<210> SEQ ID NO 39
<211> LENGTH: 16
<212> TYPE: RNA
<213> ORGANISM: Homo sapiens

<400> SEQUENCE: 39
auaaaacuug aauuuc                                                     16

<210> SEQ ID NO 40
<211> LENGTH: 16
<212> TYPE: RNA
<213> ORGANISM: Mus sp.

<400> SEQUENCE: 40
auaaaacuug aauuuu                                                     16

<210> SEQ ID NO 41
<211> LENGTH: 16
<212> TYPE: RNA
<213> ORGANISM: Rattus sp.

<400> SEQUENCE: 41
auaaaacuug aauuuu                                                     16

<210> SEQ ID NO 42
<211> LENGTH: 16
<212> TYPE: RNA
<213> ORGANISM: Canis lupus

<400> SEQUENCE: 42
auaaaacuug aauuuu                                                     16

<210> SEQ ID NO 43
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
auaaaaguag uauuuc                                                     16

<210> SEQ ID NO 44
<211> LENGTH: 5
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 44

Val Val Val Pro Pro
1               5
```